(12) United States Patent
Meade et al.

(10) Patent No.: US 7,550,263 B2
(45) Date of Patent: Jun. 23, 2009

(54) METHOD FOR THE PRODUCTION OF FUSION PROTEINS IN TRANSGENIC MAMMAL MILK

(75) Inventors: Harry Meade, Newton, MA (US); Geoffrey F. Cox, Boston, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 451 days.

(21) Appl. No.: 10/933,854

(22) Filed: Sep. 3, 2004

(65) Prior Publication Data

US 2006/0105347 A1 May 18, 2006

Related U.S. Application Data

(60) Provisional application No. 60/500,910, filed on Sep. 5, 2003.

(51) Int. Cl.
*A61K 38/00* (2006.01)
*C07H 21/04* (2006.01)
*C07K 14/00* (2006.01)
*C12N 15/00* (2006.01)
*C12Q 1/68* (2006.01)

(52) U.S. Cl. .................. 435/6; 435/69.1; 435/320.1; 514/12; 530/350; 536/23.5

(58) Field of Classification Search .................. 514/12, 514/15

See application file for complete search history.

(56) References Cited

U.S. PATENT DOCUMENTS

| | | | |
|---|---|---|---|
| 4,399,216 A | 8/1983 | Axel et al. | |
| 4,873,316 A | 10/1989 | Meade et al. | |
| 5,322,775 A | 6/1994 | Clark et al. | |
| 5,589,604 A | 12/1996 | Drohan et al. | |
| 5,633,076 A | 5/1997 | Deboer et al. | |
| 5,639,940 A | 6/1997 | Garner et al. | |
| 5,648,243 A | 7/1997 | Hurwitz | |
| 5,750,172 A | 5/1998 | Meade et al. | |
| 5,780,009 A | 7/1998 | Karatzas et al. | |
| 5,827,690 A | 10/1998 | Meade et al. | |
| 5,831,141 A | 11/1998 | Lubon et al. | |
| 5,843,705 A | 12/1998 | Ditullio et al. | |
| 5,945,577 A | 8/1999 | Stice et al. | |
| 6,201,167 B1 | 3/2001 | Pothier | |
| 6,534,479 B1 * | 3/2003 | Murgita | 514/12 |
| 7,122,522 B2 * | 10/2006 | Andersen et al. | 514/15 |

FOREIGN PATENT DOCUMENTS

| WO | WO 00/23472 | 4/2000 |
|---|---|---|
| WO | WO 01/00855 | 1/2001 |

OTHER PUBLICATIONS

Alexander et al., Eur. J. Biochem. 178, 395-401 (1988).
Alexander et al., Nucleic Acids Res. 17, 6739 (1989).
Ausubel et al., Current Protocols in Molecular Biology, John Wiley & Sons, New York, NY, Chapters 9, 10, 12, 16, 1998.
Baguisi A,(1999) et al., Production of Goats by Somatic Cell Nuclear Transfer, Nature Biotech; 17: 456-461.
Benoist et al., The trp, recA, heat shock, and lacZ promoters of *E. coli* and the SV40 early promote, Nature, 290:304-310, (1981).
Brignon et al., Febs Lett. 188, 48-55 (1977).
Campbell et al. Biol. Reprod. 49:933-942 (1993).
Campbell et al., Nucleic Acids Res. 12, 8685-8697 (1984).
Campbell et al., Nature 385:810-813 (1996).
Cibelli JB, (1998) et al., Cloned Transgenic Calves Produced From Nonquiescent Fetal Fibroblasts. Science; 280: 1256-1258.
Clark et al., Biotechnology 7: 487-492 (1989).
Cosman et al., Letters to Nature, 312: 768, (1984).
Cosman et al., Mol. Immunol., 23:935, (1986).
DiTullio, Biotechnology 10:74-77 (1992).
Eipper BA, et al., Peptidylglycine alpha-Amidating Monooxygenase: A Multifunctional Protein with Catalytic, Processing and Routing Domains, (1993) Protein Science 2, 489-49.
Eppstein et al., Biochemical and Biophysical Research Communications, 120:66-73 (1984).
Fisher, Laboratory Techniques in Biochemistry and Molecular Biology, *DNA Sequencing*, eds. Work and Burdon, Elsevier, vol. 10, 1983.
Goeddel, Gene Expression Technology: Methods in Enzymology 185, (Academic Press, San Diego, Calif. (1990).
Gorodetsky et al., Gene 66, 87-96 (1988).
Gordon et al., Biotechnology 5: 1183-1187 (1987).
Hall, Biochem. J. 242, 735-742 (1987).
Hobbs et al., J. Biol. Chem. 257:3598-3605 (1982).
Huber et al., Adv. Drug Delivery Reviews 17:279-292, 1995.
Hwang, H.-Y, et al., (1996). Creation of Homozygous Mutants of Leishmania Donovani With Single Targeting Constructs. J. Biol. Chem. 271: 30840-30846.
Ivanov et al., Biol. Chem. Hoppe-Seyler 369, 425-429 (1988).

(Continued)

*Primary Examiner*—Maryam Monshipouri
*Assistant Examiner*—Marsha M Tsay
(74) *Attorney, Agent, or Firm*—Wolf, Greenfield & Sacks, P.C.

(57) ABSTRACT

Desirable fusion proteins can be produced in and purified from the milk of transgenic animals. The peptides are made as fusion proteins with a suitable fusion partner such as human alpha-fetoprotein. The fusion partner protein acts to promote and increase the half-life of the overall molecule as well as having therapeutic effects on its own. The fusion protein is typically produced through the use of transgenic animals and can be purified away from the now the milk or other bodily fluid of such an animal by an affinity purification method. A particular advantage of producing peptides via this route, in addition to the obvious advantages of high yield and biocompatibility, is that specific post-translational modifications, such as carboxy terminal amidation, can be performed in the mammary gland. Biologically active polypeptides comprising a therapeutically active polypeptide fused to human alpha-fetoprotein fragment or a variant thereof, methods for the preparation thereof, nucleotide sequences encoding such fusion polypeptides, expression cassettes comprising such nucleotide sequences, self-replicating plasmids containing such expression cassettes, and pharmaceutical compositions containing said fusion polypeptides.

23 Claims, 4 Drawing Sheets

OTHER PUBLICATIONS

Jain, M, et al., (2001). Targeted Inactivation of G•I Does Not Alter Cardiac Function or •-Adrenergic Sensitivity. Am. J. Physiol. 280: 569H-575.
Jamieson et al., Gene 61, 85-90 (1987).
Jones et al., J. Biol. Chem. 260, 7042-7050 (1985).
Jones et al., J. Biol. Chem. 265:14684-14690, 1990.
Kanehisa (1984) Nuc. Acids Res. 12:203-213.
Kasinathan P,(2001) et al., Effect of Fibroblast Donor Cell Age and Cell Cycle on Development of Bovine Nuclear Transfer Embryos In Vitro, Biol Reprod.; 64(5): 1487-1493.
Kasinathan P, (2001) et al., Production of Calves from G1 Fibroblasts, Nature Biotech; 19: 1176-1178.
Lambda II, (ed. R. Hendrix, J. Roberts, F. Stahl, and R. Wesiberg), pp. 145-173, 209-250, 395-466, (1983).
Lim, S, et al., (1997). A Shortened Life Span of EKLF-/- Adult Erythrocytes, Due to a Deficiency of Beta -Globin Chains, is Ameliorated by Human Gamma—Globin Chains. Blood 90.
McGrane et al., TIBS 17:40-44, 1992.
Meng L, et al., (1997) Rhesus Monkeys Produced by Nuclear Transfer, Biol Reprod. Aug. 57(2):454-9.
Mercier & Vilotte, J. Dairy Sci. 76, 3079-3098 (1993).
Morinaga et al. (Proc. Natl. Acad. Sci. USA 80:4604-4608, (1983).
Mortensen, R, et al., (1992) Production of Homozygous Mutant ES Cells with a Single Targeting Construct. Mol.Cell. Biol. 12, 2391-2395.
Nagy, A, et al., (1996) Targeted Mutagenesis: Analysis of Phenotype Without Germ-Line Transmission. J. Clin. Invest. 97: 1360-1365.
Okayama et al., Mol. Cell. Biol., 3:280, (1983).
Ongeri EM, et al., (2001) Development of Goat Embryos After In vitroFertilization and Parthenogenetic Activation by Different Methods, Theriogenology Jun. 1;55(9):1933-45.
Paris et al., Biotechnol. Appl. Biochem. 12:436-449 (1990).
Pearse and Takor, *Embryology of the diffuse neuroendocrine system and its relationship to the common peptides*, Fed. Proc., 38(9) 2288-94, 1979.
Remington's Pharmaceutical Sciences, 16$^{th}$ ed., Osol, A., editor; Mack, Easton Press., Chapter 89, 95-100, 1035-1038, 1411,-1712, 1980.
Richards et al., J. Biol. Chem. 256, 526-532 (1981).
Sakai, E, et al., (1999). Recombination And Transcription of The Endogenous Ig Heavy Chain Locus Is Effected by the Ig Heavy Chain Intronic Enhancer Core Region In the Absence of the Matrix Attachment Regions. Proc. Natl. Acad. Sci. U.S.A. 96: 1526-1531.
Sambrook et al., (1989). Molecular Cloning—A Laboratory Manual, 2nd Ed., ed. (Cold Spring Harbor Laboratory Press.
Shen et al., DNA 8:101-108, 1989.
Shimada et al., Febs Letters 279:198-200, 1991.
Soulier et al., Febs Letts. 297:13 (1992).
Stewart, Nucleic Acids Res. 12:3895-3907, 1984.
Tan et al., Dev. Biol. 146:24-37, 1991.
Vilotte et al., Biochimie 69, 609-620 (1987).
Watson et al. (1987) in The Molecular Biology of the Gene (4th ed.) Chapter 19, 595-617, (1987).
Wilmut I, et al., (2002) Somatic Cell Nuclear Transfer, Nature Oct. 10;419(6907):583-6.
Wilmut I, et al., (1997) Viable Offspring Derived From Fetal and Adult Mammalian Cells, Nature Feb. 27;385(6619):810-3.
Wold F., et al., In vivo Chemical Modification of Proteins, Ann. Rev. Biochem. 50 783-814 (1981).
Wright et al., High Level Expression of Active Human alpha-1-Antitrypsin in the Milk of Transgenic Sheep, (1991) Bio/Technology, 9 77-84.
Yong Z and L Yuqiang, (1998) Nuclear-Cytoplasmic Interaction and Development of Goat Embryos Reconstructed by Nuclear Transplantation: Production of Goats by Serially Cloning Embryos, Biol Reprod.; 58: 266-269.
Yu-Lee & Rosen, J. Biol. Chem. 258, 10794-10804 (1983).
Zbikowska, et al., Biochem. J. 365:7-11, 2002.
Zbikowski et al., Transgenic Res. 11:425-435, 2002.
Zou X, et al.,(2002) Generation of Cloned Goats (Capra Hircus) From Transfected Foetal Fibroblast Cells, The Effect of Donor Cell Cycle, Mol Reprod Dev.; 61: 164-172.
Chou et al., Expression of Chimeric monomer and Dimer Proteins on the Plasma Membrane of Mammalian Cells. iotechnology and Bioengineering. 1999, vol. 65, pp. 160-169.
Gluzman SV40-transformed simian cells support the replication of early SV40 mutants. Cell. Jan. 1981;23(1):175-82.
Kerr et al. The bladder as a bioreactor: urothelium production and secretion of growth hormone into urine. Nat. Biotechnology. 1998 16: 75-79.
Liao et al. Design of Transgene for Efficient Expression of Active Chimeric Proteins on Mammalian Cells. Biotechnology and Bioengineering 2001 . . . vol. 73, p. 313-323.
Mourey et al. Antithrombin III: structural and functional aspects. Biochimie 1990, 72 (8) 599-608.
Schnieke et al. Human Factor IX Transgenic Sheep Produced by Transfer of Nuclei from Transfected Fetal Fibroblasts. Science Dec. 1997, vol. 278, p. 2130-2133.
Wells et al. Production of Cloned Claves Following Nuclear Transfer with Cultured Adult Mural Granulosa Cells. Biol. of Reproduction 60, 996-1005 (1999).

* cited by examiner

FIG. 1

FLOWCHART OF AN EMBODIMENT OF THE CURRENT INVENTION

Initial transfection of mammalian cell line with transgene of interest for the bifunctional protein
↓
Selection of cell-lines
↓
Nuclear transfer/embryo transfer procedure
↓
Birth of hetorozygote animal(s)
↓
Characterization of heterozygote transgenic animal(s)
↓
Biopsy of transgenic animal to generate cell population
↓
Expansion of biopsied heterozygote cell-line in culture
↓
Selection of homozygous cells with increased concentration of selective agents
↓
Pick surviving cell colonies
↓
Characterizing surviving cells (FISH, Southern blot)
↓
Using homozygous cell lines in NT/ET
↓
Production of a homozygous animal for desired transgene
↓
Accelerated production of herd homozygous for desired transgene(s)
↓
Production of desired biopharmaceutical/Production of genetically desirable livestock or non-human mammals

FIG. 2

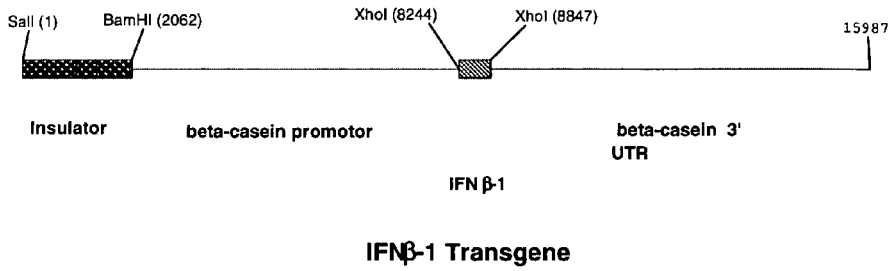

IFNβ-1 Transgene

```
 976 TCGAGGTCAACATGACCAACAAGTGTCTCCTCCAAATTGCTCTCCTGTTGTGCTTCTCCACTACAGCTCTTTCCATGAGCTACAACTTGCTTGGATTCCTACAA
   1▶  M  T  N  K  C  L  L  Q  I  A  L  L  L  C  F  S  T  T  A  L  S  M  S  Y  N     L  G  F  L  Q
1080 AGAAGCAGCAATTTTCAGTGTCAGAAGCTCCTGTGGCAATTGAATGGGAGGCTTGAATACTGCCTCAAGGACAGGATGAACTTTGACATCCCTGAGGAGATTAA
  32▶ R  S     N  F  Q  C  Q  K  L  L  W  Q  L  N  G  R  L  E  Y  C  L  K  D  R  M  N  F  D  I  P  E  E  I  K
         PstI (1187)
1184 GCAGCTGCAGCAGTTCCAGAAGGAGGACGCCGCATTGACCATCTATGAGATGCTCCAGAACATCTTTGCTATTTTCAGACAAGATTCATCTAGCACTGGCTGGA
  66▶ Q  L  Q  Q  F  Q  K  E  D  A  A  L  T  I  Y  E  M  L  Q  N  I  F  A  I  F  R  Q  D  S  S  S  T  G  W
1288 ATGAGACTATTGTTGAGAACCTCCTGGCTAATGTCTATCATCAGATAAACCATCTGAAGACAGTCCTGGAAGAAAAACTGGAGAAAGAAGATTTCACCAGGGGA
 101▶ N  E  T  I  V  E  N  L  L  A  N  V  Y  H  Q  I  N  H  L  K  T  V  L  E  E  K  L  E  K  E  D  F  T  R  G
1392 AAACTCATGAGCAGTCTGCACCTGAAAAGATATTATGGGAGGATTCTGCATTACCTGAAGGCCAAGGAGTACAGTCACTGTGCCTGGACCATAGTCAGAGTGGA
 136▶ K  L  M  S  S  L  H  L  K  R  Y  Y  G  R  I  L  H  Y  L  K  A  K  E  Y  S  H  C  A  W  T  I  V  R  V  E
1496 AATCCTAAGGAACTTTTACTTCATTAACAGACTTACAGGTTACCTCCGAAACTGAAGATCTCCTAGCCTGTGCCTCTGGGACC
 170▶ I  L  R  N  F  Y  F  I  N  R  L  T  G  Y  L  R  N  •
```

FIG. 3

Human Beta Interferon

Amino Acid Sequence

```
ORIGIN
        1 msynllgflq rssnfqcqkl lwqlngrley clkdrmnfdi peeikqlqqf qkedaaltiy
       61 emlqnifaif rqdssstgwn etivenllan vyhqinhlkt vleekleked ftrgklmssl
      121 hlkryygril hylkakeysh cawtivrvei lrnfyfinrl tgylrn
```

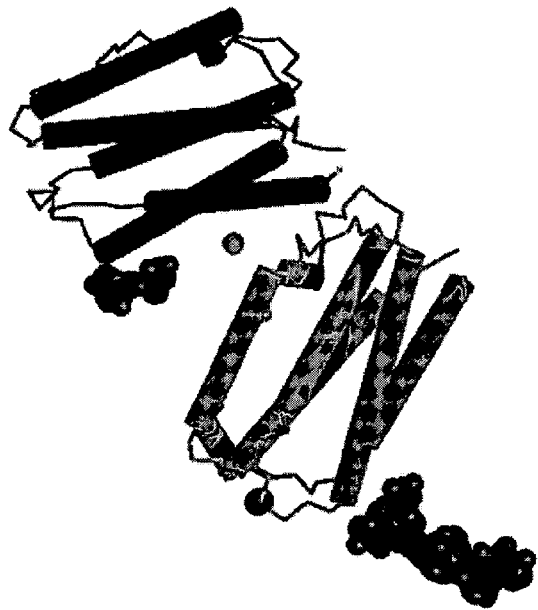

Derived from:
Karpusas, M., et al., *The crystal structure of human interferon beta at 2.2-A resolution*, PROC NATL ACAD SCI USA 94 pp. 11813 (1997).

FIG. 4

NCBI Reference No.#      AAR65430
590 aa    Homo Sapien
Recombinant human alpha-fetoprotein ORIGIN
```
      1 tlhrneygia sildsyqcta eisladlati ffaqfvqeat ykevskmvkd altaiekptg
     61 deqssgclen qlpafleelc hekeilekyg hsdccsqsee grhncflahk kptaawiplf
    121 qvpepvtsce ayeedretfm nkfiyeiarr hpflyaptil lsaagyekii pscckaenav
    181 ecfqtkaatv tkelressll nqhacpvmkn fgtrtfqait vtklsqkftk vnfteiqklv
    241 ldvahvhehc cradvldclq dgekimsyic sqqdtlsnki teccklttle rgqciihaen
    301 dekpeglspn lnrflgdrdf nqfssgekni flasfvheys rrhpqlavsv ilrvakgyqe
    361 llekcfqten plecqdkgee elqkyiqesq alakrscglf qklgeyylqn eflvaytkka
    421 pqltsselma itrkmaataa tccqlsedkl lacgegaadi iighlcirhe mtpvnpgvgq
    481 cctssyanrr pcfsslvvde tyvppafsdd kfifhkdlcq aqgvalqrmk qeflinlvkq
    541 kpqiteeqle aliadfsgll ekccqgqeqe vcfaeegqkl isktgaalgv…
``` joined to linker 1:

…aedgervlpgsg… linked to
NCBI Reference No.#      AAC41702
187 aa    Homo Sapien
Recombinant human Beta-Interferon ORIGIN
```
      1 …mtnkcllqia lllcfsttal smsynllgfl qrssncqcqk llwqlngrle yclkdrrnfd
     61 ipeeikqlqq fqkedaavti yemlqnifai frqdssstgw netivenlla nvyhqrnhlk
    121 tvleekleke dftrgkrmss lhlkryygri lhylkakeds hcawtivrve ilrnfyvinr
    181 ltgylrn
```

METHOD FOR THE PRODUCTION OF FUSION PROTEINS IN TRANSGENIC MAMMAL MILK

RELATED APPLICATIONS

This application claims priority under 35 §119 from U.S. provisional application Ser. No. 60/500,910, filed on Sep. 5, 2003, the entire contents of which are incorporated herein by reference.

FIELD OF THE INVENTION

The present invention relates to the production of bi-functional fusion proteins which are biologically active and can be used pharmaceutically. In particular the current invention provides for the production of a β-interferon and α-fetoprotein fusion protein sequences linked to a recombinant human Alpha-Fetoprotein sequence in the milk of transgenic mammals, particularly non-human placental mammals and provides for the use of such fusion proteins in therapeutic applications or disease conditions.

BACKGROUND OF THE INVENTION

As stated above, the present invention relates generally to the field of the transgenic production of fusion proteins in the milk of transgenic animals. More particularly, it concerns improved methods for generating transgenic non-human mammalian animals, of various species, capable of producing a variety of fusion proteins of interest.

Currently, there are numerous polypeptides, macromolecules and/or proteins ("proteins of interest") possessing one or more potential therapeutic activities cannot be exploited pharmaceutically. There may be various reasons for this inability, such as low stability in vivo, altered glycosylation patterns found in proteins from non-eukaryotic cells, improper translational processing, tertiary structure, fragile structure, immunogenicity, the difficulty of producing them on an industrially acceptable scale or the like. Moreover, some therapeutically interesting proteins do not give the expected results in vivo because of problems related to the method of their purification, administration or pharmacokinetics.

The present invention makes it possible to overcome these disadvantages. The instant invention provides new fusion molecules which permits the exploitation of the physiological properties or effects of the proteins of interest. The present invention results especially from the demonstration that it is possible to fuse a physiologically active sequence derived from a biologically active protein to another recombinant protein structure consisting of a protein sequence retaining the physiological activity of human alpha-fetoprotein to derive a bi-functional fusion protein, without impairing the biological properties of either the alpha-fetoprotein or the second protein moiety thereof. It also results from the demonstration by the Inventors that the recombinant human alpha-fetoprotein protein sequence of the invention ("AFP") can improve the half-life of the fusion proteins of the invention, and add synergistic therapeutic efficacy as well.

The physiological effects of AFP have been shown in the prior art to include both stimulative and inhibitory effects on various cell types. These effects in large part are determined by the target cell type, the relative concentration of AFP, and the presence of other cytokines and growth factors. For example, AFP can inhibit the growth of many types of tumor cells, and, in particular, inhibits estrogen-stimulated or estrogen-sensitive cell growth. Conversely, AFP stimulates the growth of normal embryonic fibroblasts. AFP has also been shown to have both immunosuppressive and immunoproliferative effects. Therefore the therapeutic effectiveness of an AFP fusion protein can be utilized in such a way as to maximize the pharmacologic effectiveness of treatments for various disease states, especially using bi-functional molecules.

The fusion proteins according to the current invention make it possible to maintain, in the body of an animal, a desirable biological activity for a prolonged period. The proteins of interest according to the current invention can also be expressed secreted by recombinant organisms, such as in cell culture production facilities, or transgenic mammals, at levels permitting their commercial exploitation. Along this line, transgenic mammals are a preferred manufacturing and expression vehicle for the fusion proteins of the invention.

Mammals having certain desired traits or characteristics, such as increased weight, milk content, milk production volume, length of lactation interval and disease resistance have long been desired. Traditional breeding processes are capable of producing animals with some specifically desired traits, but often these traits these are often accompanied by a number of undesired characteristics, and are often too time-consuming, costly and unreliable to develop. Moreover, these processes are completely incapable of allowing a specific animal line from producing gene products, such as desirable protein therapeutics that are otherwise entirely absent from the genetic complement of the species in question (i.e., human or humanized plasma protein or other molecules in ungulate milk). The development of technology capable of generating transgenic animals provides a means for exceptional precision in the production of animals that are engineered to carry specific traits or are designed to express certain proteins or other novel molecular compounds of therapeutic, scientific or commercial value. That is, transgenic animals are animals that carry the gene(s) of interest that has been deliberately introduced into existing somatic cells and/or germ line cells at an early stage of development. As the animals develop and grow the protein product or specific developmental change engineered into the animal is expressed, and at that point is present in the genetic complement of that animal and its offspring.

In a preferred embodiment the current invention provides for the bulk production of a bi-functional fusion protein of interest in the milk of transgenic mammals. The production of a fusion protein of interest in milk is ideal as a bulk process because very large volumes of milk that can be produced, collected and purified using known dairy technology. A second advantage of using a transgenic mammalian process is that some reactions which can be essential for biological activity in humans, for example carboxy-terminal amidation, are difficult to perform in good yield by currently available chemical means or in bacterial or other in vitro situations. For example, carboxy-terminal amidation is catalyzed by a specific enzyme which recognizes and modifies a fusion protein of interest or proteins with a glycine residue at the carboxy terminus. Therefore, suitably designed fusion proteins of the invention can be specifically amidated before secretion into the milk of transgenic animals. This is only one example of a range of post-translational modifications which can be carried out by the biosynthetic pathways in the mammary gland and which can potentially be harnessed for the synthesis of particular fusion proteins. Other examples of desirable post-translational modifications include di-sulfide bridge formation, γ-carboxylation of glutamic acid residues and the addition of O- and N- linked glycosylation.

With regard to a physiologically active fragment of AFP it should also be noted that the non-glycosylated form of recombinant AFP exhibits similar biological properties to the normally glycosylated form and provides a standardized consistent product due to the lack of glycosylation variability. It may also be more easily produced in in vitro or transgenic systems. Therefore, non-glycosylated AFP is a preferred form for commercial production.

According to the prior art, the generation of an animal capable of producing a recombinant protein of interest is known. However, what remained unknown prior to the current invention was the level of genetic manipulation required for the current invention, the modified sequences of the various fusion protein components available, the synergistic effect of the current bi-functional molecules, and the disease states or pathologies in which they are useful.

Accordingly, a need exists for improved methods of therapeutic composition generation. The methods of the invention are typically applied to primary somatic cells, in the context of nuclear transfer, for the generation of transgenic animals useful in the production of recombinant fusion bi-functional proteins of interest in their milk.

SUMMARY OF THE INVENTION

Briefly stated, the current invention provides a method for the production of bi-functional fusion proteins of interest, preferably through the use of transgenic animals. The method involves transfecting a non-human mammalian cell-line with a given transgene construct, the construct containing at least one recombinant DNA coding sequence encoding a desired first desired peptide fragment and a second desired peptide fragment each of which retain the biological activity of an individual protein of interest. The process involves developing the DNA construct; selecting a cell line(s) in which the desired recombinant sequence has been inserted into the genome of that cell or cell-line; performing a nuclear transfer procedure to generate a transgenic animal heterozygous for the desired fusion protein. Thereafter the fusion protein expressing the bi-functional fusion protein may be collected from the milk or other bodily fluid of the transgenic animal and purified for use as a therapeutic agent.

An additional step that may be performed according to the invention is to biopsy the heterozygous transgenic animal. Thereafter, according to the current invention the cell line can be expanded in vitro with the biopsied cell-line obtained from the heterozygous animal used to develop multiple transgenic animals in a shorter time period.

Alternatively or in addition to, a nuclear transfer procedure can be conducted to generate a mass of transgenic cells useful for research, serial cloning, or other in vitro use. In a preferred embodiment of the current invention surviving cells are characterized by one of several known molecular biology methods including without limitation FISH, Southern Blot, or PCR. The methods provided above will allow for the accelerated production of a transgenic herd of animals homozygous for desired transgene(s) and thereby the more efficient production of a desired biopharmaceutical. In this way the current invention allows for the production of genetically desirable livestock or non-human mammals themselves expressing a bi-functional fusion protein of interest.

In addition, the methods of the current invention will also allow the development of one or more homozygous animals that carry a particularly beneficial or valuable fusion protein, potentially increasing herd yield of a desired protein much more quickly than previous methods. Likewise the methods of the current invention will also provide for the replacement of specific transgenic animals lost through disease or their own mortality. They will also facilitate and accelerate the production of transgenic animals constructed with a variety of DNA constructs so as to optimize the production and lower the cost for the production of a desirable biopharmaceutical composition.

Therefore according to an embodiment of the current invention it may be useful to make transgenic animals homozygous for a fusion protein of interest. In this embodiment it is preferable that the transgene of interest and the genetic composition of the heterozygous transgenic animal are characterized. Thereafter cells homozygous for the desired transgene are selected through the use of marker agents; characterizing surviving cells using known molecular biology methods; picking surviving cells or cell colonies cells for use in a second round of nuclear transfer or embryo transfer; and producing an animal homozygous for a desired fusion protein.

One subject of the present invention therefore relates to bi-functional fusion proteins containing an active part derived from a peptide fragment having a therapeutic activity, coupled to a human alpha-fetoprotein or a variant of human alpha-fetoprotein having a separate and, in some cases, synergistic effect.

Another subject of the invention relates to a process for preparing the chimeric molecules described above. More specifically, this process consists in causing a eukaryotic or prokaryotic cellular host to express a nucleotide sequence encoding the desired fusion protein, and then in harvesting the fusion protein product.

Accordingly, it is an object of the invention to provide a medicament that is capable of treating myasthenia gravis.

It is yet another object of the invention to provide a medicament that inhibits the proliferation of a cancer cell and/or is anti-angiogenic to endothelial cells that may develop into blood vessels capable of feeding a tumor.

It is still another object of the invention to provide a method for treating a patient suffering from rheumatoid arthritis.

It is another object of the invention to provide a method of treating cancer by employing the medicaments described herein.

It is another object of the invention to provide a method of treating skin conditions or damaged skin by applying bi-functional proteins according to the invention.

These and other objects which will be more readily apparent upon reading the following disclosure may be achieved by the present invention.

BRIEF DESCRIPTION OF THE DRAWINGS

FIG. 1 Shows a flowchart of the methods involved in practicing the invention.

FIG. 2 Shows a Generalized Diagram of the Process of Creating Cloned Animals through Nuclear Transfer.

FIG. 3 Shows a diagram of the amino acid sequence of 0-interferon.

FIG. 4 Shows a fusion protein of interest

DETAILED DESCRIPTION

The following abbreviations have designated meanings in the specification:

Abbreviation Key:
  Somatic Cell Nuclear Transfer (SCNT)
  Cystic Fibrosis Transmembrane Conductance Regulator (CFTR)

Nuclear Transfer (NT)
Synthetic Oviductal Fluid (SOF)
Fetal Bovine Serum (FBS)
Polymerase Chain Reaction (PCR)
Bovine Serum Albumin (BSA)

Explanation of Terms:

AFP secretory signal or "AFP signal peptide" or "AFP leader" or "AFP signal sequence"—A peptide having substantially the same amino acid sequence as amino acids 1-18 set forth in Genbank Accession No. V01514 (encoded by nucleotides 45-98). The protein secretory signal is cleaved from AFP during processing or maturation processes;

Bovine—Of or relating to various species of cows.

Biological Activity/Physiological Activity—is intended to be interpreted broadly. In the case of the interferon-like proteins, it includes all known (or to be discovered) properties including properties specific to human IFN-α's or to human IFN-β, or common to both, such as their antiviral activity and their capability to modulate antigens of the major histocompatibility complex (MHC).

Biological Fluid—an aqueous solution produced by an organism, such as a mammal, bird, amphibian, or reptile, which contains proteins that are secreted by cells that are bathed in the aqueous solution. Examples include: milk, urine, saliva, seminal fluid, vaginal fluid, synovial fluid, lymph fluid, amniotic fluid, blood, sweat, and tears; as well as an aqueous solution produced by a plant, including, for example, exudates and guttation fluid, xylem, phloem, resin, and nectar.

Biological-fluid producing cell—A cell that is bathed by a biological fluid and that secretes a protein into the biological fluid.

Biopharmaceutical—shall mean any medicinal drug, therapeutic, vaccine or any medically useful composition whose origin, synthesis, or manufacture involves the use of microorganisms, recombinant animals (including, without limitation, chimeric or transgenic animals), nuclear transfer, microinjection, or cell culture techniques.

Caprine—Of or relating to various species of goats.

Encoding—refers generally to the sequence information being present in a translatable form, usually operably linked to a promoter (e.g., a beta-casein or beta-lacto globulin promoter). A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code.

Expression Vector—A genetically engineered plasmid or virus, derived from, for example, a bacteriophage, adenovirus, retrovirus, poxvirus, herpesvirus, or artificial chromosome, that is used to transfer an AFP fusion protein coding sequence, operably linked to a promoter, into a host cell, such that the encoded recombinant AFP fusion protein is expressed within the host cell.

Functional Proteins—Proteins which have a biological or other activity or use, similar to that seen when produced endogenously.

Fusion Slide—A glass slide for parallel electrodes that are placed a fixed distance apart. Cell couplets are placed between the electrodes to receive an electrical current for fusion and activation.

Homologous Sequences—refers to genetic sequences that, when compared, exhibit similarity. The standards for homology in nucleic acids are either measures for homology generally used in the art or hybridization conditions. Substantial homology in the nucleic acid context means either that the segments, or their complementary strands, when compared, are identical when optimally aligned, with appropriate nucleotide insertions or deletions, in at least about 60% of the residues, usually at least about 70%, more usually at least about 80%, preferably at least about 90%, and more preferably at least about 95 to 98% of the nucleotides. Alternatively, substantial homology exists when the segments will hybridize under selective hybridization conditions, to a strand, or its complement. Selectivity of hybridization exists when hybridization occurs which is more selective than total lack of specificity. Typically, selective hybridization will occur when there is at least about 55% homology over a stretch of at least about 14 nucleotides, preferably at least about 65%, more preferably at least about 75%, and most preferably at least about 90%.

Human alpha-fetoprotein or "AFP" or "rAFP"—a peptide having substantially the same amino acid sequence as the mature alpha-fetoprotein (amino acids 19-609) set forth in Genbank Accession No. V01514 (SEQ ID NO: 4) and encoded by nucleotides 99-1874 of the cDNA sequence set forth in Genbank Accession No. V01514 (SEQ ID NO: 3) and reported in Morinaga et al. (Proc. Natl. Acad. Sci. USA 80:4604-4608, (1983)).

Human alpha-fetoprotein precursor—a peptide having substantially the same amino acid sequence as amino acids 1-609 set forth in Genbank Accession No. V01514 (SEQ ID NO: 2) and encoded by nucleotides 45-1874 of the cDNA sequence set forth in Genbank Accession No. V01514 (SEQ ID NO: 1).

Leader sequence or a "signal sequence"—a nucleic acid sequence that encodes a protein secretory signal, and, when operably linked to a downstream nucleic acid molecule encoding an AFP fusion protein and directs AFP secretion. The leader sequence may be the native human AFP leader, an artificially-derived leader, or may obtained from the same gene as the promoter used to direct transcription of the AFP coding sequence, or from another protein that is normally secreted from a cell.

Milk-producing cell—A cell (e.g., a mammary epithelial cell) that secretes a protein into milk.

Milk-specific promoter—A promoter that naturally directs expression of a gene in a cell that secretes a protein into milk (e.g., a mammary epithelial cell) and includes, for example, the casein promoters, e.g., alpha casein promoter (e.g., alpha S-1 casein promoter and alpha S2-casein promoter), beta casein promoter (e.g., the goat beta casein gene promoter (DiTullio, BioTechnology 10:74-77, 1992), gamma casein promoter, and kappa casein promoter; the whey acidic protein (WAP) promoter (Gorton et al., BioTechnology 5: 1183-1187, 1987); the beta-lactoglobulin promoter (Clark et al., BioTechnology 7: 487-492, 1989); and the alpha-lactalbumin promoter (Soulier et al., FEBS Letts. 297:13, 1992). Also included are promoters that are specifically activated in mammary tissue and are thus useful in accordance with this invention, for example, the long terminal repeat (LTR) promoter of the mouse mammary tumor virus (MMTV).

Non-glycosylated human AFP—a peptide having substantially the same amino acid sequence as the mature human alpha-fetoprotein described above, except including a mutation at amino acid position 233 of SEQ ID NO: 4 from an asparagine residue to a glutamine residue (as set forth in SEQ ID NO: 6), thereby eliminating the single glycosylation site. The nucleic acid sequence of the precursor non-glycosylated human alpha-fetoprotein includes nucleotides 45 through 1874 of the sequence set forth in SEQ ID NO: 5.

Nuclear Transfer—refers to a method of cloning wherein the nucleus from a donor cell is transplanted into an enucleated oocyte.

Operably Linked—A gene and one or more regulatory sequences are connected in such a way as to permit gene expression when the appropriate molecules (e.g., transcriptional activator proteins) are bound to the regulatory sequences.

Ovine—of, relating to or resembling sheep.

Parthenogenic—The development of an embryo from an oocyte without the penetration of sperm.

Pharmaceutically Pure—Refers to fusion protein that is suitable for unequivocal biological testing as well as for appropriate administration to effect treatment of a human patient. Substantially pharmaceutically pure means at least about 90% pure.

Porcine—of or resembling pigs or swine.

Promoter—A minimal sequence sufficient to direct transcription. Also included in the invention are those promoter elements which are sufficient to render promoter-dependent gene expression controllable for cell type-specific, tissue-specific, temporal-specific, or inducible by external signals or agents; such elements may be located in the 5' or 3' or intron sequence regions of the native gene.

Protein—as used herein is intended to include glycoproteins, as well as proteins having other additions. This also includes fragmentary or truncated polypeptides that retain physiological function.

Recombinant—refers to a nucleic acid sequence which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functional polypeptide sequences to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., a bi-functional fusion protein according to the instant invention.

Therapeutically-effective amount—An amount of a therapeutic molecule or a fragment thereof that, when administered to a patient, inhibits or stimulates a biological activity modulated by that molecule.

Transformation, "Transfection," or "Transduction"—Any method for introducing foreign molecules into a cell. Lipofection, DEAE-dextran-mediated transfection, microinjection, nuclear transfer (see, e.g., Campbell et al. BIOL. REPROD. 49:933-942, 1993; Campbell et al., NATURE 385: 810-813, 1996), protoplast fusion, calcium phosphate precipitation, transduction (e.g., bacteriophage, adenoviral retroviral, or other viral delivery), electroporation, and biolistic transformation are just a few of the methods known to those skilled in the art which may be used.

Transformed cell or Transfected cell—A cell (or a descendent of a cell) into which a nucleic acid molecule encoding AFP has been introduced by means of recombinant DNA techniques. The nucleic acid molecule may be stably incorporated into the host chromosome, or may be maintained episomally.

Transgene—Any piece of a nucleic acid molecule that is inserted by artifice into a cell, or an ancestor thereof, and becomes part of the genome of the animal which develops from that cell. Such a transgene may include a gene which is partly or entirely exogenous (i.e., foreign) to the transgenic animal, or may represent a gene having identity to an endogenous gene of the animal.

Transgenic—Any cell that includes a nucleic acid molecule that has been inserted by artifice into a cell, or an ancestor thereof, and becomes part of the genome of the animal which develops from that cell.

Transgenic Organism—An organism into which genetic material from another organism has been experimentally transferred, so that the host acquires the genetic information of the transferred genes in its chromosomes in addition to that already in its genetic complement.

Ungulate—of or relating to a hoofed typically herbivorous quadruped mammal, including, without limitation, sheep, swine, goats, cattle and horses.

Vector—As used herein means a plasmid, a phage DNA, or other DNA sequence that (1) is able to replicate in a host cell, (2) is able to transform a host cell, and (3) contains a marker suitable for identifying transformed cells.

According to the present invention, there is provided a method for the production of a fusion protein of interest, the process comprising expressing in the milk of a transgenic non-human placental mammal a fusion protein comprising a first polypeptide of interest linked to a second polypeptide of interest both of which have independent physiological effects.

One protein family of interest for use in the bi-functional molecule of the current invention is the interferon family of proteins. Interferon's ("IFN's") constitute a group of naturally occurring proteins which are known to exhibit antiviral, anti-tumor and immunoregulatory behavior. This class of cytokines has immune stimulating/modulating activity. The interferon's are a family of small proteins and glycoprotein's with molecular weights of approximately 15,000 to 28,000 Daltons (15-28 kDa) produced and secreted in vivo by cells primarily in response to viral infection, and also in response to synthetic or biological inducers. The nomenclature conventions used to describe and name interferon's is complex. This is largely due to advancing knowledge and technology which has shown various interferons's to be produced by the same cell types, the discovery of different species and forms of interferon, and the discovery that some forms are identical to others previously reported. Because human native interferon has long been expensive to extract, techniques have been developed for preparing recombinant forms of human interferon.

Interferon's exert their cellular activities by binding to specific membrane receptors on the cell surface. Once bound to the cell membrane, interferon's initiate a complex sequence of intracellular events, including the up-regulation of certain other cytokines, induction of certain enzymes, suppression of cell proliferation, immunomodulating activities such as enhancement of the phagocytic activity of macrophages and augmentation of the specific cytotoxicity of lymphocytes (e.g., cellular immunity) for target cells, and inhibition of virus replication in virus-infected cells.

A range of biological activities are associated with IFNs including antiviral, anti-proliferative and immunoregulatory activities. Therapeutic uses include the treatment of Hairy Cell leukemia, Chronic myelogenous leukemia, low grade non-Hodgkin lymphoma, cutaneous T cell lymphoma carcinoid tumors, renal cell carcinoma, squamous epithelial tumors of the head and neck, multiple myeloma, and malignant melanoma. With regards to viral disease, IFN-α has been found to aid the treatment of chronic active hepatitis, caused by either Hepatitis B or C viruses.

In 1993 the Food and Drug Administration (FDA) approved beta interferon (IFN-β) as a therapy for multiple sclerosis (MS). The administration of β-interferon slows the progression of this chronic and often disabling neurologic disease, which affects about 350,000 people in the United States. The availability of the drug is a milestone for patients with MS, who often derive scant benefit from corticosteroids and other therapies.

MS is an autoimmune disease, in which the body's defense system attacks the myelin sheath, the fatty substance that protects nerve fibers of the brain and spinal cord much as insulation covers electrical wire. The transmission of electrical impulses to and from the brain is disrupted as MS lesions create breaks in the myelin sheath. As a result, people with MS experience symptoms including weakness, fatigue, incontinence, visual impairment, slurred speech, or sometimes paralysis. Beta interferon has been shown in the prior art to positively effect the treatment of multiple sclerosis. Ambulatory patients with relapsing-remitting MS who took high doses of beta interferon had about 30% fewer attacks, and half as many severe ones, as people who took a placebo. Therefore, a molecule of interest made through the methods of the current invention is an AFP-IFN-β bi-functional fusion protein, with beneficial synergistic effects when used therapeutically against MS. That is, the therapeutic effect of β-IFN is synergistically heightened by the presence of a functional alpha-fetoprotein moiety—itself having beneficial effectiveness against MS.

Suitable host organisms for possible prokaryotic or eukaryotic in vitro production include: *E. coli., Pseudomonas, Bacillus subtilis, Bacillus thuringiensis*, various strains of yeast, *Bacillus thermophilus*, animal cells such as mice, rat or Chinese hamster ovary (CHO) cells, plant cells, animal and plant hosts and the like. It must be recognized that when a host of choice is transformed with the vector, appropriate promoter-operator sequences are also introduced in order for a protein sequence to be expressed. Hosts may be prokaryotic or eukaryotic, *E. coli.* and CHO cells are the preferred hosts for in vitro systems. The fusion proteins expressed in accordance with the present invention may be glycosylated or unglycosylated depending on the glycosylation occurring in the host organism used to produce the protein and the DNA sequence of the genetically engineered sequences according to the current invention. If desired, unglycosylated the expressed protein obtained when *E. coli.* or a *Bacillus* is the host organism may be optionally glycosylated in vitro by chemical, enzymatic and other types of modifications known in the art.

In accordance with the methods of the current invention for transgenic animals a transgenic primary cell line (from either caprine, bovine, ovine, porcine or any other non-human vertebrate origin) suitable for somatic cell nuclear transfer is created by transfection of the fusion protein nucleic acid construct of interest (for example, a mammary gland-specific transgene(s) targeting expression of a human alpha-fetoprotein—β-interferon fusion protein to the mammary gland). The transgene construct can either contain a selection marker (such as neomycin, kanamycin, tetracycline, puromycin, zeocin, hygromycin or any other selectable marker) or be co-transfected with a cassette able to express the selection marker in cell culture.

The invention provides expression vectors containing a nucleic acid sequence described herein, operably linked to at least one regulatory sequence. Many such vectors are commercially available, and other suitable vectors can be readily prepared by the skilled artisan. "Operably linked" or "operatively linked" is intended to mean that the nucleic acid molecule is linked to a regulatory sequence in a manner which allows expression of the nucleic acid sequence by a host organism. Regulatory sequences are art recognized and are selected to produce the encoded polypeptide or protein. Accordingly, the term "regulatory sequence" includes promoters, enhancers, and other expression control elements which are described in Goeddel, GENE EXPRESSION TECHNOLOGY: METHODS IN ENZYMOLOGY 185, (Academic Press, San Diego, Calif. (1990)). For example, the native regulatory sequences or regulatory sequences native to the transformed host cell can be employed.

It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both. (A LABORATORY MANUAL, 2nd Ed., ed. Sambrook et al. (Cold Spring Harbor Laboratory Press, 1989) Chapters 16 and 17)).

Following selection of colonies recombinant for the desired nucleic acid construct, cells are isolated and expanded, with aliquots frozen for long-term preservation according to procedures known in the field. The selected transgenic cell-lines can be characterized using standard molecular biology methods (PCR, Southern blotting, FISH). Cell lines carrying nucleic acid constructs of the bi-functional fusion protein of interest, of the appropriate copy number, generally with a single integration site (although the same technique could be used with multiple integration sites) can then be used as karyoplast donors in a somatic cell nuclear transfer protocol known in the art. Following nuclear transfer, and embryo transfer to a recipient animal, and gestation, live transgenic offspring are obtained. Typically this transgenic offspring carries only one transgene integration on a specific chromosome, the other homologous chromosome not carrying an integration in the same site. Hence the transgenic offspring is heterozygous for the transgene, maintaining the current need for at least two successive breeding cycles to generate a homozygous transgenic animal.

EXAMPLE 1

AFP—β Interferon

Another feature of the invention is a method of treating a patient in need of the bi-functional fusion protein of the invention by administering to the patient a therapeutically-effective amount of a biological fluid (e.g., milk, urine, saliva, seminal or vaginal fluid, synovial fluid, lymph fluid, amniotic fluid, the fluid within the yolk sac, the chorion, or the allantois of an egg, blood, sweat, and tears; or an aqueous solution produced by a plant, including, for example, exudates or guttation fluid, xylem, phloem, resin, and nectar), or extract thereof, that includes the bi-functional fusion protein of the invention that is obtained from a transgenic non-human organism (e.g., a mammal (e.g., a mouse, goat, sheep, camel, cow, pig, rabbit, horse, ox, or llama), a bird, a reptile, an amphibian, or a plant). In a desired embodiment, the bi-functional protein of the invention has the sequence set forth in the combination of SEQ ID NOS: 4, 10 and 24. In another embodiment, the biological fluid is milk. In yet another embodiment, the bi-functional fusion protein of the invention is purified from the transgenic non-human organism's biological fluid (e.g., the bi-functional fusion protein of the invention purified from the milk, urine, blood, or lymph of a mammal). In various desired embodiments, the method may be used to inhibit or treat an immunologic disorder, e.g., infection with the human immunodeficiency virus (HIV), cancer cell growth, to induce bone marrow cell proliferation (for example, after a bone marrow transplant or after administration of a myelotoxic treatment such as chemotherapy or radiation treatment), or as an immunosuppressive agent (for example, to inhibit autoreactive immune cell proliferation, to inhibit rejection of a transplanted organ (e.g., graft-versus-host disease), or to inhibit or treat an autoimmune disorder, e.g., rheumatoid arthritis, muscular dystrophy, systemic lupus erythematosus, myasthenia gravis, multiple sclerosis, insulin-dependent diabetes mellitus, or psoriasis). human AFP gene (GenBank Accession #M16110).

EXAMPLE 2

Fusion Protein Sequences of Interest

A. Alpha Feto Protein

Seq. Id.: 1    The entire cDNA sequence set forth in Genbank Accession No. V01514.
Seq. Id.: 2    Genbank Accession No. V01514 (amino acids 1-609).
Seq. Id.: 3    Genbank Accession No. V01514 (nucleic acids 99-1874) from the cDNA of Seq. Id. 1.
Seq. Id.: 4    Genbank Accession No. V01514 (amino acids 19-609).
Seq. Id.: 5    Genbank Accession No. V01514 (nucleic acid sequence of the precursor non-glycosylated human alpha-fetoprotein for the nucleic acids 45-1874).
Seq. Id.: 6    Genbank Accession No. V01514 (amino acids 19-609) except including a mutation at amino acid position 233 of SEQ ID NO: 4 from an asparagine residue to a glutamine residue to remove the single glycosylation site in AFP.
Seq. Id.: 7    Genbank Accession No. V01514 (amino acids 1-18) the AFP secretory signal.
Seq. Id.: 8    Genbank Accession No. V01514 (nucleotides 45-98 of the AFP secretory signal, DNA sequence).
Seq. Id.: 9    human AFP gene (GenBank Accession #M16110)

B. Partner Protein Sequences of Interest

Seq. Id.: 10    Genbank/EMBL/DDBJ Accession No. AAC41702, from the National Center for Biotechnology Information - human β-interferon variant 1 (1-187 amino acid residues)
Seq. Id.: 11    Genbank/EMBL/DDBJ Accession No. CAA00839, from the National Center for Biotechnology Information - human α-interferon variant 2A (1-212 amino acid residues)
Seq. Id.: 12    Genbank/EMBL/DDBJ Accession No. AAP20099, from the National Center for Biotechnology Information - human α-interferon variant 2B (1-166 amino acid residues)
Seq. Id.: 13    Protein Sequence Record Genbank Accession No. NP_795372, from the National Center for Biotechnology Information - human τ-interferon (1-189 amino acid residues)

-continued

Seq. Id.: 14    Protein Sequence Record Genbank Accession No. NP_76918 from the National Center for Biotechnology Information - human α-interferon variant 1 (1-189 amino acid residues)
Seq. Id.: 15    Protein Sequence Record Genbank Accession No. NP_000610 from the National Center for Biotechnology Information - human γ-interferon (1-166 amino acid residues)
Seq. Id.: 16    Genbank/EMBL/DDBJ Accession No. AAH18990, from the National Center for Biotechnology Information - light chain human ferritin (1-175 amino acid residues)
Seq. Id.: 17    Genbank/EMBL/DDBJ Accession No. AAH16857, from the National Center for Biotechnology Information - heavy chain human ferritin (1-183 amino acid residues)
Seq. Id.: 18    Genbank/EMBL/DDBJ Accession No. AAH05322, from the National Center for Biotechnology Information - human Decorin (1-359 amino acid residues)
Seq. Id.: 19    Genbank Accession No. 113936 - human antithrombin (1-464 amino acid residues)
Seq. Id.: 20    Genbank Accession No. 113936 - "cleaved" human antithrombin (1-464 amino acid residues) generated by enzyme cleavage of antithrombin between Arginine residue 393 and Serine residue 394.
Seq. Id.: 21    Protein Sequence Record Genbank Accession No. NP_002611, from the National Center for Biotechnology Information - human Platelet Factor 4 (1-104 amino acid residues)
Seq. Id.: 22    Protein Sequence Record Genbank Accession No. NP_000939 from the National Center for Biotechnology Information - human prolactin (1-227 amino acid residues)
Seq. Id.: 23    Genbank/EMBL DDBJ Accession No. CAA26189, from the National Center for Biotechnology Information - human calcitonin (1-93 amino acid residues)
Seq. Id.: 24    Genbank/EMBL DDBJ Accession No. AAE57231, from the National Center for Biotechnology Information - IRES linker sequence variant 1 (1-236 amino acid residues)
Seq. Id.: 25    Genbank/EMBL DDBJ Accession No. AAH08915, from the National Center for Biotechnology Information - Alpha-1-Antitrypsin (1-406 amino acid residues)

C. Optimized Codons

Expression of protein in a host organism, and most particularly in a transgenic organism, can in part depend on how well the start codon of the DNA construct matches the host organism's optimum (or consensus) start site, how well the mRNA's codon usage matches the "codon bias" of the host organism, the presence of cryptic intron splice sites (potentially resulting in truncated or nonsense proteins), and presence of stabilizing or destabilizing signals (i.e. PEST degradation signals) in the protein of interest.

Proteins of interest derived from organisms that have a nucleic acid profile highly divergent from that of the host organism may benefit from re-engineering the cDNA sequence so as to optimize codons of key amino acids so that they more closely match the "preferred" or common nucleic acid codons for given amino acids. For example, a protein of interest from a high A-T content organism (*Dictyostelium discoideum* or *Plasmodium falciparum* for example) could more easily be expressed by optimizing the codons towards G-C heavy codons, while leaving the amino acid sequence unchanged.

In transgenic animal production systems the use of optimized expression systems for the production of large quantities of proteins of interest may be necessary to make enough of a compound available to make it therapeutically feasible. To this end it is possible to re-engineer synthetic genes utilizing optimized codons for all of the bi-functional fusion proteins under provided according to the current invention.

Materials And Methods

Transgenic Goats & Cattle.

The herds of pure- and mixed-breed scrapie-free Alpine, Saanen and Toggenburg dairy goats used as cell and cell line donors for this study were maintained under Good Agricultural Practice (GAP) guidelines. Similarly, cattle used should be maintained under Good Agricultural Practice (GAP) guidelines and be certified to originate from a scrapie and bovine encephalitis free herd.

Isolation of Caprine Fetal Somatic Cell Lines.

Primary caprine fetal fibroblast cell lines to be used as karyoplast donors were derived from 35- and 40-day fetuses. Fetuses were surgically removed and placed in equilibrated phosphate-buffered saline (PBS, $Ca^{++}/Mg^{++}$-free). Single cell suspensions were prepared by mincing fetal tissue exposed to 0.025% trypsin, 0.5 mM EDTA at 38° C. for 10 minutes. Cells were washed with fetal cell medium [equilibrated Medium-199 (M199, Gibco) with 10% fetal bovine serum (FBS) supplemented with nucleosides, 0.1 mM 2-mercaptoethanol, 2 mM L-glutamine and 1% penicillin/streptomycin (10,000 I.U. each/ml)], and were cultured in 25 $cm^2$ flasks. A confluent monolayer of primary fetal cells was harvested by trypsinization after 4 days of incubation and then maintained in culture or cryopreserved.

Homogenous Fusion Proteins

As used herein, the terms substantially pure and homogenous describe a protein or polypeptide which has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially pure protein will typically comprise over about 85 to 90% of a protein sample, more usually will comprise at least about 95%, and preferably will be over about 99% pure. Normally, purity is measured on a polyacrylamide gel, with homogeneity determined by staining. For certain purposes high resolution will be used and HPLC or a similar means for purification utilized. For most purposes, a simple chromatography column or polyacrylamide gel will be used to determine purity.

A protein is substantially free of naturally associated components when it is separated from the native contaminants which accompany it in its natural state. Thus, a protein which is chemically synthesized or synthesized in a cellular system different from the cell from which it naturally originates will be substantially free from its naturally associated components. The term is used to describe polypeptides and nucleic acids which have been synthesized in heterologous mammalian cells or plant cells, *E. coli.* and other prokaryotes. The present invention provides for substantially pure preparations for therapeutic use. Various methods for their isolation from biological material may be devised, based in part upon the structural and functional descriptions contained herein.

Construction of the "AFP—Partner Polypeptide" Fusion Protein

According to the current invention, the term "fusion protein" is intended to describe a fused protein comprising two polypeptides of interest fused by a linker sequence amino acid sequence. According to the current invention, the generation of bi-functional fusion proteins is a useful tool in providing enhanced therapeutic options for specific disease conditions. Therefore the development of needed fusion techniques have become an increasingly important. In structural biology, the construction of recombinant fusion proteins has often been used as a means to increase the expression of soluble proteins and to facilitate protein purification. The technique has been used to study the functional activity of proteins in in vitro assays and for in vivo production. In recent years, a wide range of applications of the gene fusion technique have been reported in the field of biotechnology. These applications include the selection and production of antibodies and the engineering of bifunctional enzymes.

The construction of a fusion protein involves the linking of two macromolecules by a linker sequence. According to the current invention the macromolecules of interest include proteins or the globular domains of proteins. The selection of the linker sequence is particularly important in the construction of functional fusion proteins. In addition to the necessity of an appropriate amino acid composition, the overall folding of the linker sequence must be taken into consideration. In practice, it is often unfavorable to have a linker sequence with high propensity for forming helix or strand structures, because these would limit the flexibility of the fusion protein and consequently affect its functional activity. Therefore, the design of a linker sequence often requires careful consideration in order to avoid such secondary structural elements. A set of sample linker sequences that are known to adopt extended conformations as determined by X-ray crystallography and NMR is provided below:

Sample Linker Sequences:

| SEQ. No. | Residues | | | | | | | | | | | |
|---|---|---|---|---|---|---|---|---|---|---|---|---|
| 1 | ALA  | GLU   | ASP   | GLY   | GLU   | ARG   | VAL  | LEU  | PRO   | GLY   | SER   | GLY   |
|   | 0.25 | -0.62 | -0.72 | -0.18 | -0.62 | -1.80 | 0.54 | 0.53 | -0.07 | -0.18 | -0.26 | -0.18 |
| 2 | ALA  | PRO   | GLU   | LYS   | GLY   | LYS   | ASN   | THR  | LEU  | GLY   | SER   | GLY   |
|   | 0.25 | -0.07 | -0.62 | -1.10 | -0.18 | -1.10 | -0.64 | 0.16 | 0.53 | -0.18 | -0.26 | -0.18 |
| 3 | ALA  | PRO   | SER   | SER   | LYS   | SER   | THR  | SER   | GLY   | GLY   | SER   | GLY   |
|   | 0.25 | -0.07 | -0.26 | -0.26 | -1.10 | -0.26 | 0.16 | -0.26 | -0.18 | -0.18 | -0.26 | -0.18 |
| 4 | ALA  | LYS   | PRO   | GLY   | LEU  | VAL  | ASP   | ASN   | GLN   | GLY   | SER   | GLY   |
|   | 0.25 | -1.10 | -0.07 | -0.18 | 0.53 | 0.54 | -0.72 | -0.64 | -0.69 | -0.18 | -0.26 | -0.18 |
| 5 | ALA  | PHE  | GLY   | ASN   | ALA  | ASN   | SER   | ALA  | ARG   | GLY   | SER   | GLY   |
|   | 0.25 | 0.61 | -0.18 | -0.64 | 0.25 | -0.64 | -0.26 | 0.25 | -1.80 | -0.18 | -0.26 | -0.18 |

-continued

Sample Linker Sequences:

| SEQ. No. | Residues | | | | | | | | | | | |
|---|---|---|---|---|---|---|---|---|---|---|---|---|
| 6 | ALA 0.25 | PRO -0.07 | SER -0.26 | ASP -0.72 | LYS -1.10 | GLU -0.62 | GLY -0.18 | TYR 0.02 | SER -0.26 | GLY -0.18 | SER -0.26 | GLY -0.18 |
| 7 | ALA 0.25 | LYS -1.10 | PRO -0.07 | ASN -0.64 | PRO -0.07 | THR 0.16 | GLY -0.18 | THR 0.16 | VAL 0.54 | GLY -0.18 | SER -0.26 | GLY -0.18 |
| 8 | ALA 0.25 | ILE 0.73 | HIS -0.46 | GLU -0.62 | TYR 0.02 | PHE 0.61 | ARG -1.80 | GLY -0.18 | GLY -0.18 | GLY -0.18 | SER -0.26 | GLY -0.18 |
| 9 | ALA 0.25 | LEU 0.53 | HIS -0.46 | GLY -0.18 | ARG -1.80 | GLY -0.18 | GLY -0.18 | GLU -0.62 | ASP -0.72 | GLY -0.18 | SER -0.26 | GLY -0.18 |
| 10 | ALA 0.25 | SER -0.26 | SER -0.26 | PRO -0.07 | ASP -0.72 | VAL 0.54 | ALA 0.25 | LYS -1.10 | GLY -0.18 | GLY -0.18 | SER -0.26 | GLY -0.18 |

These are the amino acid sequences and the hydrophobicities of the residues.

The linker sequence useful for the current invention comprise at least one amino acid residue or more, those provided above are 12 amino acid residues long. The orientation of the first and second polypeptides of interest (ex: AFP and β-interferon fragments respectively), can be altered according to convenience with the N-terminal sequence of AFP being fused to a linker and the C-terminal end of a second polypeptide of interest or vice versa. Two biologically active molecules are fused to provide heightened therapeutic function as well as to enhance molecular half-life. The choice of carrier protein is frequently ruled by the application of the fusion protein constructed. In the current invention AFP functions as a carrier protein polypeptide, while retaining its own therapeutic effects and offering synergistic improvements in activity.

The joining of the various genomic or cDNA fragments encoding the transgene, is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct may optionally encode a leader sequence to allow efficient expression of the fusion protein.

The DNA construct of human AFP is fused to a linker sequence and a second polynucleotide sequence of interest. The overall nucleotide sequence may have its codons optimized to enhance expression and/or to be more compatible with the chosen expression platform (ex: transgenic mammal, prokaryote cell culture, mammalian cell culture etc.). Since glycosylation of the fusion protein of interest is a characteristic of the eukaryotic system, a bi-functional recombinant protein sequence useful for therapeutic applications is preferably produced in eukaryotic cells or transgenic mammals. In these production platforms a plasmid selected for amplification of the fusion protein of interest and made transgenic for the cDNA construct of the bi-functional protein of interest may be subcloned into a gene-amplification system of choice. Thereafter the DNA construct it is cut out and transfected into the genome of a target nucleus.

Expression of a desired fusion protein in mammalian cells is preferred according to the current invention in order to ensure the production of biologically functional protein because of factors such as the presence of native leader sequences that ensure successful secretion of the protein, the presence of appropriate folding factors and the capacity for posttranslational modifications. In addition, the expression of a bi-functional fusion protein in mammalian cells is essential for use in the production of biopharmaceuticals.

The invention relates to a method of production of peptides having a specifically desired sequence and to the protein and nucleic acid intermediates necessary for the practice of the method. The bi-functional fusion protein sequence to be produced can be identical to the desired end product (the peptide of interest) or it can contain one or more tandem copies of the peptide of interest and/or it can contain sequences associated with a selectively cleavable bond. Most preferably, the method of the invention comprises the steps of:

a) providing a cDNA or genomic DNA construct which encodes a fusion protein having a first polypeptide of interest, a peptide linker sequence and a second polypeptide of interest, which gene is operably connected to a first locus control region and a first promoter;

b) making a transgenic animal having the operably connected fusion gene integrated into its genome, whereby the fusion protein is expressed and incorporated into the milk of the transgenic animal upon lactation or hormonal induction of lactation; and c) isolating the fusion protein from the milk of the transgenic animal.

In cell culture production of the transgene vectors containing replicon and control sequences derived from species compatible with a host cell are used in connection with the host. The vector ordinarily carries a replicon site, as well as specific genes which are capable of providing phenotypic selection in transformed cells. The expression of the fusion protein can also be placed under control with other regulatory sequences which may be homologous to the organism in its untransformed state. For example, in transgenic goats a goat β-casein promoter can be used which will activate expression of the transgene of interest upon the initiation of lactation. Other promoters/operator systems or portions thereof can be employed as well. For example, whey acid promoters, beta-lactoglobin, alkaline phosphatase, and the like can be used.

For mammalian hosts, several possible vector systems are available for initial expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, antibiotic resistance, or resistance to heavy metals such as copper or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Preparation of Donor Cells for Embryo Reconstruction.

Transfected fetal somatic cells were seeded in 4-well plates with fetal cell medium and maintained in culture (5% $CO_2$, 39° C.). After 48 hours, the medium was replaced with fresh low serum (0.5% FBS) fetal cell medium. The culture medium was replaced with low serum fetal cell medium every 48 to 72 hours over the next 2-7 days following low serum medium, somatic cells (to be used as karyoplast donors) were harvested by trypsinization. The cells were re-suspended in equilibrated M199 with 10% FBS supplemented with 2 mM L-glutamine, 1% penicillin/streptomycin (10,000 I. U. each/ml) for at least 6 hours prior to fusion to the enucleated oocytes. The current experiments for the generation of desirable transgenic animals are preferably carried out with goat cells or mouse cells for the generation or goats or mice respectively but, according to the current invention, could be carried out with any mammalian cell line desired.

Oocyte Collection.

Oocyte donor does were synchronized and super ovulated as previously described (Ongeri, et al., 2001), and were mated to vasectomized males over a 48-hour interval. After collection, oocytes were cultured in equilibrated M199 with 10% FBS supplemented with 2 mM L-glutamine and 1% penicillin/streptomycin (10,000 I.U. each/ml).

Cytoplast Preparation and Enucleation.

All oocytes were treated with cytochalasin-B (Sigma, 5 μg/ml in SOF with 10% FBS) 15 to 30 minutes prior to enucleation. Metaphase-II stage oocytes were enucleated with a 25 to 30 μm glass pipette by aspirating the first polar body and adjacent cytoplasm surrounding the polar body (~30 % of the cytoplasm) to remove the metaphase plate. After enucleation, all oocytes were immediately reconstructed.

Nuclear Transfer and Reconstruction

Donor cell injection was conducted in the same medium used for oocyte enucleation. One donor cell was placed between the *zona pellucida* and the ooplasmic membrane using a glass pipet. The cell-oocyte couplets were incubated in SOF for 30 to 60 minutes before electrofusion and activation procedures. Reconstructed oocytes were equilibrated in fusion buffer (300 mM mannitol, 0.05 mM $CaCl_2$, 0.1 mM $MgSO_4$, 1 mM $K_2HPO_4$, 0.1 mM glutathione, 0.1 mg/ml BSA) for 2 minutes. Electrofusion and activation were conducted at room temperature, in a fusion chamber with 2 stainless steel electrodes fashioned into a "fusion slide" (500 μm gap; BTX-Genetronics, San Diego, Calif.) filled with fusion medium.

Fusion was performed using a fusion slide. The fusion slide was placed inside a fusion dish, and the dish was flooded with a sufficient amount of fusion buffer to cover the electrodes of the fusion slide. Couplets were removed from the culture incubator and washed through fusion buffer. Using a stereomicroscope, couplets were placed equidistant between the electrodes, with the karyoplast/cytoplast junction parallel to the electrodes. It should be noted that the voltage range applied to the couplets to promote activation and fusion can be from 1.0 kV/cm to 10.0 kV/cm. Preferably however, the initial single simultaneous fusion and activation electrical pulse has a voltage range of 2.0 to 3.0 kV/cm, most preferably at 2.5 kV/cm, preferably for at least 20 μsec duration. This is applied to the cell couplet using a BTX ECM 2001 Electrocell Manipulator. The duration of the micropulse can vary from 10 to 80 μsec. After the process the treated couplet is typically transferred to a drop of fresh fusion buffer. Fusion treated couplets were washed through equilibrated SOF/FBS, then transferred to equilibrated SOF/ FBS with or without cytochalasin-B. If cytocholasin-B is used its concentration can vary from 1 to 15 μg/ml, most preferably at 5 μg/ml. The couplets were incubated at 37-39° C. in a humidified gas chamber containing approximately 5% $CO_2$ in air. It should be noted that mannitol may be used in the place of cytocholasin-B throughout any of the protocols provided in the current disclosure (HEPES-buffered mannitol (0.3 mm) based medium with $Ca^{+2}$ and BSA).

Nuclear Transfer Embryo Culture and Transfer to Recipients.

Significant advances in nuclear transfer have occurred since the initial report of success in the sheep utilizing somatic cells (Wilmut et al., 1997). Many other species have since been cloned from somatic cells (Baguisi et al., 1999 and Cibelli et al., 1998) with varying degrees of success. Numerous other fetal and adult somatic tissue types (Zou et al., 2001 and Wells et al., 1999), as well as embryonic (Meng et al., 1997), have also been reported. The stage of cell cycle that the karyoplast is in at time of reconstruction has also been documented as critical in different laboratories methodologies (Kasinathan et al., BIOL. REPROD. 2001; Yong et al., 1998; and Kasinathan et al., NATURE BIOTECH. 2001).

All nuclear transfer embryos of the current invention were cultured in 50 μl droplets of SOF with 10% FBS overlaid with mineral oil. Embryo cultures were maintained in a humidified 39° C. incubator with 5% $CO_2$ for 48 hours before transfer of the embryos to recipient does. Recipient embryo transfer was performed as previously described (Baguisi et al., 1999).

Paramount to the success of any nuclear transfer program is having adequate fusion of the karyoplast with the enucleated cytoplast. Equally important however is for that reconstructed embryo (karyoplast and cytoplast) to behave as a normal embryo and cleave and develop into a viable fetus and ultimately a live offspring. Results from this lab detailed above show that both fusion and cleavage either separately or in combination have the ability to predict in a statistically significant fashion which cell lines are favorable to nuclear transfer procedures. While alone each parameter can aid in pre-selecting which cell line to utilize, in combination the outcome for selection of a cell line is strengthened.

Pregnancy and Perinatal Care.

For goats, pregnancy was determined by ultrasonography starting on day 25 after the first day of standing estrus. Does were evaluated weekly until day 75 of gestation, and once a month thereafter to assess fetal viability. For the pregnancy that continued beyond 152 days, parturition was induced with 5 mg of PGF2μ (Lutalyse, Upjohn). Parturition occurred within 24 hours after treatment. Kids were removed from the dam immediately after birth, and received heat-treated colostrum within 1 hour after delivery. Time frames appropriate for other ungulates with regard to pregnancy and perinatal care (e.g., bovines) are known in the art.

Genotyping of Cloned Animals.

Shortly after birth, blood samples and ear skin biopsies are obtained from cloned animals (e.g., goats or cattle) and the surrogate dams for genomic DNA isolation. According to the current invention each sample may be first analyzed by PCR using primers for a specific transgenic target protein, and then subjected to Southern blot analysis using the cDNA for that specific target protein. For each sample, 5 µg of genomic DNA was digested with EcoRI (New England Biolabs, Beverly, Mass.), electrophoreses in 0.7% agarose gels (SeaKem®, Me.) and immobilized on nylon membranes (MagnaGraph, MSI, Westboro, Mass.) by capillary transfer following standard procedures known in the art. Membranes were probed with the 1.5 kb Xho I to Sal I hAT cDNA fragment labeled with $^{32}$P dCTP using the Prime-It® kit (Stratagene, La Jolla, Calif.). Hybridization was executed at 65° C. overnight. The blot is washed with 0.2×SSC, 0.1% SDS and exposed to X-OMAT™ AR film for 48 hours.

The present invention also includes a method of cloning a genetically engineered or transgenic mammal, by which a desired gene is inserted, removed or modified in the differentiated mammalian cell or cell nucleus prior to insertion of the differentiated mammalian cell or cell nucleus into the enucleated oocyte.

Also provided by the present invention are mammals obtained according to the above method, and the offspring of those mammals. The present invention is preferably used for cloning caprines or bovines but could be used with any mammalian species. The present invention further provides for the use of nuclear transfer fetuses and nuclear transfer and chimeric offspring in the area of cell, tissue and organ transplantation.

Suitable mammalian sources for oocytes include goats, sheep, cows, pigs, rabbits, guinea pigs, mice, hamsters, rats, primates, etc. Preferably, the oocytes will be obtained from ungulates, and most preferably goats or cattle. Methods for isolation of oocytes are well known in the art. Essentially, this will comprise isolating oocytes from the ovaries or reproductive tract of a mammal, e.g., a goat. A readily available source of ungulate oocytes is from hormonally induced female animals.

For the successful use of techniques such as genetic engineering, nuclear transfer and cloning, oocytes may preferably be matured in vivo before these cells may be used as recipient cells for nuclear transfer, and before they can be fertilized by the sperm cell to develop into an embryo. Metaphase II stage oocytes, which have been matured in vivo, have been successfully used in nuclear transfer techniques. Essentially, mature metaphase II oocytes are collected surgically from either non-super ovulated or super ovulated animals several hours past the onset of estrus or past the injection of human chorionic gonadotropin (hCG) or similar hormone.

Moreover, it should be noted that the ability to modify animal genomes through transgenic technology offers new alternatives for the manufacture of recombinant proteins. The production of human recombinant pharmaceuticals in the milk of transgenic farm animals solves many of the problems associated with microbial bioreactors (e.g., lack of post-translational modifications, improper protein folding, high purification costs) or animal cell bioreactors (e.g., high capital costs, expensive culture media, low yields). The current invention enables the use of transgenic production of biopharmaceuticals, fusion proteins, plasma proteins, and other molecules of interest in the milk or other bodily fluid (i.e., urine or blood) of transgenic animals homozygous for a desired gene. Fusion proteins capable of being produced in through the method of the invention include those containing an alpha-fetoprotein polypeptide and a fusion protein partner including: antithrombin III, truncated ATIII, lactoferrin, urokinase, Platelet Factor 4 ("PF4"), alpha-fetoprotein, alpha-1-antitrypsin, C-1 esterase inhibitor, decorin, alpha interferon, beta interferon, ferritin, prolactin, CFTR, blood Factor X, blood Factor VIII, as well as erythropoietin.

According to an embodiment of the current invention when multiple or successive rounds of transgenic selection are utilized to generate a cell or cell line homozygous for more than one trait such a cell or cell line can be treated with compositions to lengthen the number of passes a given cell line can withstand in in vitro culture. Telomerase would be among such compounds that could be so utilized.

The use of living organisms as the production process means that all of the material produced will be chemically identical to the natural product. In terms of basic amino acid structures this means that only L-optical isomers, having the natural configuration, will be present in the product. Also the number of wrong sequences will be negligible because of the high fidelity of biological synthesis compared to chemical routes, in which the relative inefficiency of coupling reactions will always produce failed sequences. The absence of side reactions is also an important consideration with further modification reactions such as carboxy-terminal amidation. Again, the enzymes operating in vivo give a high degree of fidelity and stereospecificity which cannot be matched by chemical methods. Finally the production of a fusion protein of interest in a biological fluid means that low-level contaminants remaining in the final product are likely to be far less toxic than those originating from a chemical reactor.

One of the most important considerations in the practice of the invention is the choice of fusion partner with which to make the fusion protein. The fusion partner may be, and for preference usually will be, a natural protein or physiologically active fragment thereof, but it does not have to be. Proteins which themselves can be produced in high yields in milk, such as alpha-1-antitrypsin, are likely to be useful fusion partners in the invention. A list of desirable of proteins includes: antithrombin III, truncated ATIII, lactoferrin, urokinase, Platelet Factor 4 ("PF4"), alpha-fetoprotein, alpha-1-antitrypsin, C-1 esterase inhibitor, decorin, alpha interferon, beta interferon, ferritin, prolactin, CFTR, blood Factor X, blood Factor VIII, as well as erythropoietin. For preference, though, the fusion partner may additionally be a protein which is naturally produced in milk, as it is reasonable to assume that a protein which is normally secreted into milk, and which can be produced at high levels, will continue to be so secreted and produced after another functional polypeptide has been fused to its carboxy terminus. A particularly preferred fusion partner for the production of a fusion protein of interest in milk is human alpha-fetoprotein.

According to the instant invention there may be some variation in the sequence of a fusion partner protein from a natural sequence. Although natural, wild-type sequences (and consensus sequences in the case of allelic variants) of human alpha-fetoprotein or other fusion partners are usually preferred, some variation from the natural sequence may be accommodated or, in some cases at least, desired, provided that the properties of the fusion partner are not compromised to an unacceptable degree. Amino acid homology of at least 90 or 95% will usually be appropriate, and generally not more than one or two amino acid changes will be preferred.

As previously mentioned, expression levels of three grams per liter of ovine milk are well within the reach of existing transgenic animal technology. Such levels should also be achievable for a human alpha-fetoprotein fusion protein, which is a non-toxic endogenous protein. In addition there is no reason to believe that such a level should not be feasible in the milk of other species. Required linker sequences may contain more than the absolute minimum sequence necessary to allow separation of the two functional moieties:

1). For example, IRES linker sequence variant 1, SEQ. ID. 24.
2). Any C-terminal extension to the first fusion partner, such as the human alpha-fetoprotein extension discussed above, may also be regarded as part of the linker.

In the practice of the present invention, bi-functional fusion proteins are produced in the milk of transgenic animals. The human alpha-fetoprotein coding sequences can be obtained by screening libraries of genomic material or reverse-translated messenger RNA derived from the animal of choice (such as cattle or mice). These sequences along with the desired polypeptide sequence of the fusion partner protein are then cloned into an appropriate plasmid vector and amplified in a suitable host organism, usually *E. coli*. The DNA sequence encoding the peptide of choice can then be constructed, for example, by polymerase chain reaction amplification of a mixture of overlapping annealed oligonucleotides.

After amplification of the vector, the DNA construct would be excised with the appropriate 5' and 3' control sequences, purified away from the remains of the vector and used to produce transgenic animals that have integrated into their genome the desired bi-functional fusion protein. Conversely, with some vectors, such as yeast artificial chromosomes (YACs), it is not necessary to remove the assembled construct from the vector; in such cases the amplified vector may be used directly to make transgenic animals. In this case bi-functional refers to the presence of a first polypeptide encoded by enough of a protein sequence nucleic acid sequence to retain its biological activity, this first polypeptide is then joined to a the coding sequence for a second polypeptide also containing enough of a polypeptide sequence of a protein to retain its physiological activity. The coding sequence being operatively linked to a control sequence which enables the coding sequence to be expressed in the milk of a transgenic non-human placental mammal.

A DNA sequence which is suitable for directing production to the milk of transgenic animals carries a 5'-promoter region derived from a naturally-derived milk protein and is consequently under the control of hormonal and tissue-specific factors. Such a promoter should therefore be most active in lactating mammary tissue. According to the current invention the promoter so utilized can be followed by a DNA sequence directing the production of a protein leader sequence which would direct the secretion of the fusion protein across the mammary epithelium into the milk. At the other end of the fusion protein construct a suitable 3'-sequence, preferably also derived from a naturally secreted milk protein, and may be added to improve stability of mRNA. An example of suitable control sequences for the production of proteins in the milk of transgenic animals are those from the caprine beta casein promoter.

The production of transgenic animals can now be performed using a variety of methods. The method preferred by the current invention is nuclear transfer.

Fusion Protein Sequences.

Preferred fusion proteins of the invention will be illustrated by the following examples. The preferred embodiment of this invention is a fusion protein made from a human alpha-fetoprotein polypeptide joined via a single methionine residue at its carboxy terminus to an β interferon polypeptide (IFN-β). In an alternate embodiment of this fusion protein of the invention the IFN-β polypeptide would carry an extra glycine at the carboxy terminus to act as a substrate for the alpha-amidating enzyme. The sequence of this preferred embodiment of the invention is provided below:

In a preferred embodiment of the current invention the DNA sequence encoding this construct would carry the 5'-beta-casein promoter region, the entire human alpha-fetoprotein coding sequence with all of the coding exons, a linker and then the human IFN-β coding sequence. A fusion protein has the same fusion partners as that provided above but uses a different linker sequence. This requires the fusion protein to carry the amino acid linker sequence between the carboxy terminus of the human alpha-fetoprotein and the IFN-β.

This would have to be produced by making appropriate changes in the DNA coding region. A fusion protein may be prepared as described above but under the control of the human or bovine 5'- and 3'-control sequences either from beta-lactoglobulin or from any other suitable promoter involved in controlling the expression of milk proteins.

A large number of DNA sequences corresponding to the various fusion proteins of interest are presented and identified. The fusion proteins of the invention provide for use of a physiologically active alpha-fetoprotein polypeptide as a first domain linked to various second polypeptide fusion partners. This invention contemplates and includes all interferon's native, natural, modified, or recombinant DNA interferon-like proteins as the potential fusion partner of the alpha-fetoprotein domain. All of these interferon's and others known proteins are in the art or to be known are within the contemplation of the invention. The present invention is principally concerned with various modified fusion proteins or polypeptides of alpha and beta interferon's fused to an alpha-fetoprotein domain. Glycosylated interferon's have been reported to be obtained by expressing the proteins in animal cells or in yeast.

The selection of the position of the molecule best suited for a modification depends on the particular protein. Thus, in accordance with the invention, recognition of desirable sequences that retain their native physiological activity can be introduced at any point in a naturally occurring protein sequence providing such introduced sequences do not adversely affect biological activity where such activity is desired. It is only necessary in accordance with the invention that there be incorporated that much of the amino acid consensus sequence that will contain or be the site for the desired biological activity.

The following describes illustrative, but not limiting, specific embodiments.

Preferred Human Bi-Functional AFP Fusion Proteins
 AFP—β Interferon
 AFP—α Interferon
 AFP—tau Interferon
 AFP—antithrombin III
 AFP—Decorin
 AFP—Prolactin
 AFP—γ Interferon
 AFP—PF4
 AFP—Calcitonin
 AFP—Alpha-1-Antitrypsin Construction of the Antithrombin III—Alpha-fetoprotein Fusion Protein Antithrombin or Antithrombin III (ATIII) is a single chain glycoprotein involved in the coagulation process. It is synthesized primarily in the liver with a signal peptide of 32 amino acids necessary for its intracellular transport through the endoplasmic reticulum; the peptide is then cleaved prior to secretion. Mourey et al., BIOCHIMIE 72:599-608 (1990).

ATIII is a member of the serpin family of proteins and functions as an inhibitor of thrombin and other enzymes involved in the clotting cascade. As used herein, the active native intact form of ATIII is designated the S (stressed) form (S-ATIII). S-ATIII forms a tight binding complex with thrombin (markedly enhanced by the presence of heparin) and other enzymes (not all serpins have heparin affinity).

S-ATIII can be cleaved to the relaxed (R)-conformation (R-ATIII) by a variety of enzymes, including thrombin. ATIII can be derived from any organism which produces the protein in nature. In a particular embodiment the organism is bovine or human. The amino acid sequence of bovine ATIII is available under GenBank Accession No. 1168462, and the amino acid sequence of human ATIII is available under GenBank Accession No. 113936.

The particular portions and conformations of ATIII or its biological equivalents, which are the subject of this invention, may also be produced by the use of an enzyme (e.g. elastase) in vivo. For example, an enzyme may be used in vivo, with or without plasma or native ATIII to serve as an additional substrate, to produce a fragment, conformation, biological equivalent, or derivative of ATIII that inhibits endothelial cell proliferation, angiogenesis and/or tumor growth. It has been determined that certain conformations of ATIII reduce angiogenesis, endothelial cell proliferation, and tumor growth. (As used herein, endothelial cell proliferation also includes endothelial cell migration and tube formation.) As described herein, ATIII and/or a fragment, conformation, biological equivalent, or derivative can be made or isolated by numerous methods known in the art, including, but not limited to, purification, transgenic and recombinant methods.

However, the insertion of the nucleotide sequence is preferably made at a site in the nucleotide sequence encoding EFN-β so as to minimize an undesirable effect on the biological activity of the resultant recombinant protein, when such biological activity is critical.

Milk Specific Promoters.

The transcriptional promoters useful in practicing the present invention are those promoters that are preferentially activated in mammary epithelial cells, including promoters that control the genes encoding milk proteins such as caseins, beta-lacto globulin (Clark et al., (1989) BIO/TECHNOLOGY 7: 487-492), whey acid protein (Gorton et al. (1987) BIO/TECHNOLOGY 5: 1183-1187), and lactalbumin (Soulier et al., (1992) FEBS LETTS. 297: 13). Casein promoters may be derived from the alpha, beta, gamma or kappa casein genes of any mammalian species; a preferred promoter is derived from the goat beta casein gene (DiTullio, (1992) BIO/TECHNOLOGY 10:74-77). The milk-specific protein promoter or the promoters that are specifically activated in mammary tissue may be derived from either cDNA or genomic sequences. Preferably, they are genomic in origin.

DNA sequence information is available for all of the mammary gland specific genes listed above, in at least one, and often several organisms. See, e.g., Richards et al., J. BIOL. CHEM. 256, 526-532 (1981) (α-lactalbumin rat); Campbell et al., NUCLEIC ACIDS RES. 12, 8685-8697 (1984) (rat WAP); Jones et al., J. BIOL. CHEM. 260, 7042-7050 (1985) (rat β-casein); Yu-Lee & Rosen, J. BIOL. CHEM. 258, 10794-10804 (1983) (rat γ-casein); Hall, BIOCHEM. J. 242, 735-742 (1987) (α-lactalbumin human); Stewart, NUCLEIC ACIDS RES. 12, 389 (1984) (bovine αs1 and κ casein cDNAs); Gorodetsky et al., GENE 66, 87-96 (1988) (bovine β casein); Alexander et al., EUR. J. BIOCHEM. 178, 395-401 (1988) (bovine κ casein); Brignon et al., FEBS LETT. 188, 48-55 (1977) (bovine αS2 casein); Jamieson et al., GENE 61, 85-90 (1987), Ivanov et al., Biol. Chem. Hoppe-Seyler 369, 425-429 (1988), Alexander et al., NUCLEIC ACIDS RES. 17, 6739 (1989) (bovine β lactoglobulin); Vilotte et al., BIOCHIMIE 69, 609-620 (1987) (bovine α-lactalbumin). The structure and function of the various milk protein genes are reviewed by Mercier & Vilotte, J. DAIRY SCI. 76, 3079-3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

Signal Sequences.

Among the signal sequences that are useful in accordance with this invention are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the expression system of this invention. The size of the signal sequence is not critical for this invention. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin are useful in the present invention. The preferred signal sequence is the goat β-casein signal sequence.

Signal sequences from other secreted proteins, e.g., proteins secreted by liver cells, kidney cell, or pancreatic cells can also be used.

Amino-Terminal Regions of Secreted Proteins.

The efficacy with which a non-secreted protein is secreted can be enhanced by inclusion in the protein to be secreted all or part of the coding sequence of a protein which is normally secreted. Preferably the entire sequence of the protein which is normally secreted is not included in the sequence of the protein but rather only a portion of the amino terminal end of the protein which is normally secreted. For example, a protein which is not normally secreted is fused (usually at its amino terminal end) to an amino terminal portion of a protein which is normally secreted.

Preferably, the protein which is normally secreted is a protein which is normally secreted in milk. Such proteins include proteins secreted by mammary epithelial cells, milk proteins such as caseins, beta lacto globulin, whey acid protein, and lactalbumin. Casein proteins include alpha, beta, gamma or kappa casein genes of any mammalian species. A preferred protein is beta casein, e.g., a goat beta casein. The sequences which encode the secreted protein can be derived from either cDNA or genomic sequences. Preferably, they are genomic in origin, and include one or more introns.

DNA Constructs.

The expression system or construct, described herein, can also include a 3' untranslated region downstream of the DNA sequence coding for the non-secreted protein. This region apparently stabilizes the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the casein 3' untranslated region or other 3' untranslated sequences well known in the art. Preferably, the 3' untranslated region is derived from a milk specific protein. The length of the 3' untranslated region is not critical but the stabilizing effect of its poly A transcript appears important in stabilizing the RNA of the expression sequence.

Optionally, the expression system or construct includes a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

The construct can also include about 10%, 20%, 30%, or more of the N-terminal coding region of the gene preferentially expressed in mammary epithelial cells. For example, the N-terminal coding region can correspond to the promoter used, e.g., a goat β-casein N-terminal coding region.

The above-described expression systems may be prepared using methods well known in the art. For example, various ligation techniques employing conventional linkers, restriction sites etc. may be used to good effect. Preferably, the expression systems of this invention are prepared as part of larger plasmids. Such preparation allows the cloning and selection of the correct constructions in an efficient manner as is well known in the art. Most preferably, the expression systems of this invention are located between convenient restriction sites on the plasmid so that they can be easily isolated from the remaining plasmid sequences for incorporation into the desired mammal.

Prior art methods often include making a construct and testing it for the ability to produce a product in cultured cells prior to placing the construct in a transgenic animal. Surprisingly, the inventors have found that such a protocol may not be of predictive value in determining if a normally non-secreted protein can be secreted, e.g., in the milk of a transgenic animal. Therefore, it may be desirable to test constructs directly in transgenic animals, e.g., transgenic mice, as some constructs which fail to be secreted in CHO cells are secreted into the milk of transgenic animals.

Transgenic Mammals.

Preferably, the DNA constructs of the invention are introduced into the germ line of a mammal. For example, one or several copies of the construct may be incorporated into the genome of a mammalian embryo by standard transgenic techniques known in the art.

Any non-human mammal can be usefully employed in this invention. Mammals are defined herein as all animals, excluding humans, which have mammary glands and produce milk. Preferably, mammals that produce large volumes of milk and have long lactating periods are preferred. Preferred mammals are cows, sheep, goats, mice, oxen, camels and pigs. Of course, each of these mammals may not be as effective as the others with respect to any given expression sequence of this invention. For example, a particular milk-specific promoter or signal sequence may be more effective in one mammal than in others. However, one of skill in the art may easily make such choices by following the teachings of this invention.

The litters of transgenic mammals may be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity. The female species of these progeny will produce the desired protein in or along with their milk. Alternatively, the transgenic mammals may be bred to produce other transgenic progeny useful in producing the desired proteins in their milk.

Transgenic females may be tested for protein secretion into milk, using any of the assay techniques that are standard in the art (e.g., Western blots or enzymatic assays).

Other Expression Systems

While presently preferred procedures to express the modified interferon—alpha-fetoprotein combination, to make various nucleotide sequences, and to transform specific hosts have been illustrated, it is evident that the invention is not in any way limited by these illustrations. Both eukaryotic and prokaryotic host cells may be used. Several procedures for the isolation of genes and expression of interferon's in bacterial cells and heterologous cells are quite well-suited for production of modified interferons of the invention.

Likewise, the modified interferon's can be produced from vertebrate cell cultures, for instance, a COS-7 line of monkey kidney fibroblasts can be used as the host for the production of the modified interferon's with appropriate expression vectors. Many other examples of eukaryotic expression vectors have been described and are known in the art.

Vectors useful in the invention to replicate in a transformed host cell have a DNA segment containing a functional origin of replication (replicon). Plasmids and phage DNA by their very nature contain replicons facilitating replication in a host cell. The vector will have a DNA segment which conveys to a transformable host cell a property useful for selection of transformed cells from non-transformed cells. Any of a wide range of properties can be used for selection purposes. One of the most commonly used properties is antibiotic resistance, e.g., neomycin resistance or tetracycline resistance.

Purification of AFP-Fusion Protein from a Biological Fluid

The AFP fusion protein of the invention may be purified from the biological fluid of a transgenic organism using standard protein purification techniques, such as affinity chromatography (see, e.g., Ausubel et al., CURRENT PROTOCOLS IN MOLECULAR BIOLOGY, John Wiley & Sons, New York, N.Y., 1998; see also Lubon et al., U.S. Pat. No. 5,831,141) or other methods known to those skilled in the art of protein purification. Once isolated, the AFP-fusion protein can, if desired, be further purified by e.g., by high performance liquid chromatography (HPLC; e.g., see Fisher, LABORATORY TECHNIQUES IN BIOCHEMISTRY AND MOLECULAR BIOLOGY, eds. Work and Burdon, Elsevier, 1980), and/or tangential flow filtration. Following purification, the AFP fusion protein is at least 80% pure, preferably 90% pure, more preferably 95% pure, and most preferably 99% pure.

Animal Promoters

Useful promoters for the expression of AFP in mammary tissue include promoters that naturally drive the expression of mammary-specific polypeptides, such as milk proteins, although any promoter that permits secretion of AFP into milk can be used. These include, e.g., promoters that naturally direct expression of whey acidic protein (WAP), alpha S1-casein, alpha S2-casein, beta-casein, kappa-casein, beta-lactoglobulin, alpha-lactalbumin (see, e.g., Drohan et al., U.S. Pat. No. 5,589,604; Meade et al., U.S. Pat. No. 4, 873,316; and Karatzas et al., U.S. Pat. No. 5,780,009), and others described in U.S. Pat. No. 5,750,172. Whey acidic protein (WAP; Genbank Accession No. X01153), the major whey protein in rodents, is expressed at high levels exclusively in the mammary gland during late pregnancy and lactation (Hobbs et al., J. BIOL. CHEM. 257:3598-3605, 1982). For additional information on desired mammary gland-specific promoters, see, e.g., Richards et al., J. BIOL. CHEM. 256:526-532, 1981 (α-lactalbumin rat); Campbell et al., NUCLEIC ACIDS RES. 12:8685-8697, 1984 (rat WAP); Jones et al., J. BIOL. CHEM. 260:7042-7050, 1985 (rat β-casein); Yu-Lee & Rosen, J. BIOL. CHEM. 258:10794-10804, 1983 (rat γ-casein); Hall, BIOCHEM. J. 242:735-742, 1987 (human α-lactalbumin); Stewart, NUCLEIC ACIDS RES. 12:3895-3907, 1984 (bovine α-s1 and κ-casein cDNAs); Gorodetsky et al., GENE 66:87-96, 1988 (bovine β-casein); Alexander et al., EUR. J. BIOCHEM. 178:395-401, 1988 (bovine κ-casein); Brignon et al., FEBS LETT. 188:48-55, 1977 (bovine α-S2 casein); Jamieson et al., GENE 61:85-90, 1987, Ivanov et al., BIOL. CHEM. Hoppe-Seyler 369: 425-429, 1988, and Alexander et al., NUCLEIC ACIDS RES. 17:6739, 1989 (bovine β-lactoglobulin); and Vilotte et al., BIOCHIMIE 69:609-620, 1987 (bovine α-lactalbumin). The structure and function of the various milk protein genes are reviewed by Mercier & Vilotte, J. DAIRY SCI. 76:3079-3098, 1993. If additional flanking sequences are useful in optimizing expression, such sequences can be cloned using the existing sequences as probes. Mammary-gland specific regulatory sequences from different organisms can be obtained by screening libraries from such organisms using known cognate nucleotide sequences, or antibodies to cognate proteins as probes.

Useful signal sequences for expression and secretion of AFP into milk are milk-specific signal sequences. Desirably, the signal sequence is selected from milk-specific signal sequences, i.e., from a gene which encodes a product secreted into milk. Most desirably, the milk-specific signal sequence is related to a milk-specific promoter described above. The size of the signal sequence is not critical for this invention. All that is required is that the sequence be of a sufficient size to effect secretion of AFP, e.g., in the mammary tissue. For example, signal sequences from genes coding for caseins, e.g., alpha, beta, gamma, or kappa caseins, beta lactoglobulin, whey acidic protein, and lactalbumin are useful in the present invention. Signal sequences from other secreted proteins, e.g., proteins secreted by liver cells, kidney cell, or pancreatic cells can also be used.

Useful promoters for the expression of a recombinant polypeptide transgene in urinary tissue are the uroplakin and uromodulin promoters (Kerr et al., NAT. BIOTECHNOL. 16:75-79, 1998; Zbikowska, et al., BIOCHEM. J. 365:7-11, 2002; and Zbikowski et al., TRANSGENIC RES. 11:425-435, 2002), although any promoter that permits secretion of the transgene product into urine may be used.

A useful promoter for the expression and secretion of AFP into blood by blood-producing or serum-producing cells (e.g., liver epithelial cells) is the albumin promoter (see, e.g., Shen et al., DNA 8:101-108, 1989; Tan et al., DEV. BIOL. 146:24-37, 1991; McGrane et al., TIBS 17:40-44, 1992; Jones et al., J. BIOL. CHEM. 265:14684-14690, 1990; and Shimada et al., FEBS LETTERS 279:198-200, 1991), although any promoter that permits secretion of the transgene product into blood may be used. The native alpha-fetoprotein promoter can also be used (see, e.g., Genbank Accession Nos.: AB053574; AB053573; AB053572; AB053571; AB053570; and AB053569). Useful promoters for the expression of AFP in semen are described in U.S. Pat. No. 6,201,167. Useful avian-specific promoters are the ovalbumin promoter and the apo-B promoter. Other avian-specific promoters are known in the art. The ovalbumin promoter can be used to direct expression of AFP that is then deposited in the egg white of the egg. The apo-B promoter can also be used to direct expression of a recombinant polypeptide in the liver, where it will eventually be deposited into the egg yolk. Avian eggs are an optimal vehicle for expressing large quantities of recombinant polypeptides for the following reasons: (1) a large amount of protein is packed into each egg, (2) eggs are easy to collect non-invasively and can be stored for extended periods of time, and (3) eggs are sterile and, unlike milk, do not contain bacterial contaminants. Specifically, for each egg, a bird can produce three grams of albumin in the oviduct, of which greater than 50% is ovalbumin. Another three grams is produced in the liver (serum lipoproteins) and deposited in the egg yolk. In addition, since birds do not typically recognize mammalian proteins immunologically because of their evolutionary distance from mammals, the expression of AFP in birds is less likely to have any deleterious effect on the viability and health of the bird.

Other promoters that are useful in the methods of the invention include inducible promoters. Generally, recombinant proteins are expressed in a constitutive manner in most eukaryotic expression systems. The addition of inducible promoters or enhancer elements provides temporal or spatial control over expression of AFP, and provides an alternative mechanism of expression. Inducible promoters include heat shock protein, metallothionien, and MMTV-LTR, while inducible enhancer elements include those for ecdysone, muristerone A, and tetracycline/doxycycline.

The Tet-On and Tet-Off Gene Expression Systems (Clontech) is one example of an inducible system that is useful in the methods of the invention. This system uses a tetracycline (Tc) responsive element to maintain AFP expression in either an on (constitutively off, induced with Tc) or off (constitutively on, repressed with Tc or doxycycline) mode. Selectable markers can also be incorporated into the AFP transgene for easy identification of cells that have been transformed. Selectable markers generally fall into two functional categories: recessive and dominant. The recessive markers are usually genes that encode products that are not produced in the host cells (cells that lack the "marker" product or function). Marker genes for thymidine kinase (TK), dihydrofolate reductase (DHFR), adenine phosphoribosyl transferase (APRT), and hypoxanthine-guanine phosphoribosyl transferase (HGPRT) are in this category. Dominant markers include genes that encode products that confer resistance to growth-suppressing compounds (antibiotics, drugs) and/or permit growth of the host cells in metabolically restrictive environments. Commonly used markers within this category include a mutant DHFR gene that confers resistance to methotrexate; the gpt gene for xanthine-guanine phosphoribosyl transferase, which permits host cell growth in mycophenolic acid/xanthine containing media; and the neo gene for aminoglycoside 3'-phosphotransferase, which can confer resistance to G418, gentamycin, kanamycin, and neomycin.

Nucleic Acid Vectors

In certain embodiments the invention concerns vectors, or recombinant expression vectors, comprising any of the nucleic acid molecules described herein. Vectors are used herein either to amplify DNA or RNA encoding fusion proteins and/or to express DNA which encodes SSTR-fusion proteins. Vectors include, but are not limited to, plasmids, phages, cosmids, episomes, viral particles or viruses, and integratable DNA fragments (i.e., fragments integratable into the host genome by homologous recombination). Viral particles include, but are not limited to, adenoviruses, baculoviruses, parvoviruses, herpesviruses, poxviruses, adeno-associated viruses, Semliki Forest viruses, vaccinia viruses, retroviruses, microparticles and naked DNA. In various embodiments, expression may be targeted to a particular cell type or cell population by a targeting ligand. Expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE.™ vectors (Qiagen), pSE420™ (Invitrogen), and pYES2™ (Invitrogen). Expression constructs may comprise a fusion protein encoding polynucleotides operatively linked to an endogenous or exogenous expression control DNA sequence and a transcription terminator. Because of limited space for nucleic acid insertion in many vectors it may be desirable to insert smaller reporters or reporter fusion constructs. For example, deletion of all or part of the somatosatin receptor carboxy terminus may be used. Expression control DNA sequences include promoters, enhancers, operators, and regulatory element binding sites generally, and are typically selected based on the expression systems in which the expression construct is to be utilized.

Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate homologous recombination in a host cell. In various embodiments constructs may also include sequences necessary for replication in a host cell.

Various exemplary tissue-specific promoters are listed herein (Pearse and Takor, 1979; Nylen and Becker, 1995). Although not a complete list, these promoters are exemplary of the types of promoters and enhancers that may be used in certain embodiments of the invention. Additional promoters, useful in the present invention, will be readily known to those of skill in the art.

Inducible promoters include but are not limited to MT II, MMTV (mouse mammary tumor virus), c-jun, Collagenase, Stromelysin, Murine MX Gene, GRP78 Gene, α-2-Macroglobulin, Vimentin, MHC Class I Gene H-2 kB, HSP70, Proliferin, Tumor Necrosis Factor and Thyroid Stimulating Hormone-α. Cell or tissue specific expression can be achieved by using cell-specific enhancers and/or promoters. (See generally, Huber et al., ADV. DRUG DELIVERY REVIEWS 17:279-292, 1995).

Expression constructs may be utilized for production of an encoded protein, but may also be utilized simply to amplify an SSTR-fusion protein encoding polynucleotide sequence. In some embodiments, the vector is an expression vector wherein the polynucleotide is operatively linked to a polynucleotide comprising an expression control sequence. In certain embodiments autonomously replicating recombinant expression constructs such as plasmid and viral DNA vectors incorporating polynucleotides. Expression vectors may be replicable DNA constructs in which a DNA sequence encoding SSTR-fusion protein is operably linked or connected to suitable control sequences capable of effecting the expression of an SSTR-fusion protein in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences that controls the termination of transcription and translation.

In various embodiments vectors may contain a promoter that is recognized by the host organism. The promoter sequences may be prokaryotic, eukaryotic, synthetic or viral. Examples of suitable prokaryotic sequences include the promoters of bacteriophage lambda (THE BACTERIOPHAGE LAMBDA, Hershey, A. D., Ed., Cold Spring Harbor Press, Cold Spring Harbor, N.Y. (1973); LAMBDA II, Hendrix, R. W., Ed., Cold Spring Harbor Press, Cold Spring Harbor, N.Y. (1980); and, Benoist et al., *The trp, recA, heat shock, and lacZ promoters of E. coli and the SV40 early promote*, NATURE, 290:304-310, (1981). Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metalothionein.

Additional regulatory sequences may also be included in vectors. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding SSTR-fusion protein and result in the expression of the mature SSTR-fusion protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication may also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and SSTR-fusion protein encoding DNA. An example of a suitable marker is dihydrofolate reductase or thymidine kinase (see, U.S. Pat. No. 4,399,216).

Nucleotide sequences encoding reporter protein fusions, such as SSTR2-fusion proteins, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., MOL. CELL. BIOL., 3:280, (1983); Cosman et al., MOL. IMMUNOL., 23:935, (1986); and, Cosman et al., NATURE, 312: 768, (1984).

The transgene construct preferably includes a leader sequence downstream from the promoter. The leader sequence is a nucleic acid sequence that encodes a protein secretory signal, and, when operably linked to a downstream nucleic acid molecule encoding the AFP-fusion protein of the invention, and directs AFP-fusion secretion. The leader sequence may be obtained from the same gene as the promoter used to direct transcription of the nucleic acid molecule encoding AFP (for example, a gene that encodes a milk-specific protein). Alternatively, a leader sequence encoding the native human AFP protein secretory signal (amino acids 1-19 of Genbank Accession No. V01514) may be employed.

Therapeutic Uses.

The combination herein is preferably employed for in vitro use in treating these tissue cultures. The combination, however, is also be effective for in vivo applications. Depending on the intended mode of administration in vivo the compositions used may be in the dosage form of solid, semi-solid or liquid such as, e.g., tablets, pills, powders, capsules, gels, ointments, liquids, suspensions, or the like. Preferably the compositions are administered in unit dosage forms suitable for single administration of precise dosage amounts. The compositions may also include, depending on the formulation desired, pharmaceutically acceptable carriers or diluents, which are defined as aqueous-based vehicles commonly used to formulate pharmaceutical compositions for animal or human administration. The diluent is selected so as not to affect the biological activity of the human alpha-fetoprotein. Examples of such diluents are distilled water, physiological saline, Ringer's solution, dextrose solution, and Hank's solution. The same diluents may be used to reconstitute lyophilized human alpha-fetoprotein. In addition, the pharmaceutical composition may also include other medicinal agents, pharmaceutical agents, carriers, adjuvants, nontoxic, non-therapeutic, non-immunogenic stabilizers, etc. Effective amounts of such diluent or carrier will be amounts which are effective to obtain a pharmaceutically acceptable formulation in terms of solubility of components, biological activity, etc.

The compositions herein may be administered to human patients via oral, parenteral or topical administrations and otherwise systemic forms for anti-melanoma and anti-breast cancer treatment.

Fusion Protein: Multiple Functional Domains.

In accordance with the invention, bi-functional fusion proteins are contemplated that have unique dual therapeutic effects on Myasthenia Gravis, Rheumatoid Arthritis, Osteoporosis, Cancer, topical applications, and Multiple Sclerosis. Other areas of effectiveness include antiviral activity, immunoregulatory activity and anti-angiogenic activity (cleaved ATIII fusion-AFP protein).

Conservative variants according to the invention generally conserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt .alpha.-helices. Similarly, certain amino acids, such as alanine, cysteine, leucine, methionine, glutamic acid, glutamine, histidine and lysine are more commonly found in a-helices, while valine, isoleucine, phenylalanine, tyrosine, tryptophan and threonine are more commonly found in .beta.-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Preparing Bi-Functional Molecules.

A bi-functional protein contemplated by this invention is one that contains each of the previously mentioned domains, wherein upon such fusing, both domains substantially retain their associated characteristics and may have a synergistic effect on certain therapeutic applications such as myasthenia gravis or rheumatoid arthritis. Although typically produced as fusion proteins, the domains also may be fused by conventional chemical means, using multifunctional cross-linkers, for example. When fusion proteins are made, either domain may be placed C-terminal or N-terminal to the other. Suitable methods for creating the fusion protein should be ones that do not substantially change the biological activity of either of the two polypeptides of the desired fusion protein.

The present invention is not limited to any particular method of producing the desired fusion protein contemplated herein. According to the contemplated recombinant methods of production, however, the invention provides recombinant DNA constructs comprising one or more of the nucleotide sequences of the domains described in the present invention. The recombinant constructs of the present invention comprise a vector, such as a plasmid or viral vector, into which a DNA or DNA fragment, typically bearing an open reading frame, is inserted, in either orientation. The invention further contemplates cells containing these vectors.

Bacterial Expression.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli.*, *Bacillus subtilis*, *Salmonella typhimurium* and various species within the genera *Pseudomonas*, *Streptomyces*, and *Staphylococcus*, although others may, also be employed as a matter of choice. In a preferred embodiment, the prokaryotic host is *E. coli.*

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotec, Madison, Wis., USA), pBs, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRITS (Pharmacia). A preferred vector according to the invention is THE Pt7I expression vector.

These "backbone" sections are combined with an appropriate promoter and the structural sequence to be expressed. Bacterial promoters include lac, T3, T7, lambda PR or PL, trp, and ara. T7 is a preferred bacterial promoter.

Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems can also be employed to express recombinant protein. Examples of mammalian expression systems include selected mouse L cells, such as thymidine kinase-negative (TK) and adenine phosphoribosyl transferase-negative (APRT) cells. Other examples include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. In particular, as regards yeasts, there may be mentioned yeasts of the genus *Saccharomyces, Kluyveromyces, Pichia, Schwanniomyces,* or *Hansenula*. Among the fungi capable of being used in the present invention, there may be mentioned more particularly *Aspergillus* ssp, or *Trichoderma* ssp.

Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include beta-casein, beta-lactoglobulin, whey acid promoter others include: HSV thymidine kinase, early and late SV40, LTRs from retrovirus, and mouse metallothionein-1. Exemplary mammalian vectors include pWLneo, pSV2cat, pOG44, pXT1, pSG (Stratagene) pSVK3, pBPV, pMSG, and pSVL (Pharmacia). In a preferred embodiment, the mammalian expression vector is pUCIG-MET. Selectable markers include CAT (chloramphenicol transferase).

The nucleotide sequences which can be used within the framework of the present invention can be prepared in various ways. Generally, they are obtained by assembling, in reading phase, the sequences encoding each of the functional parts of the polypeptide. The latter may be isolated by the techniques of persons skilled in the art, and for example directly from cellular messenger RNAs (mRNAs), or by recloning from a complementary DNA (cDNA) library, or alternatively they may be completely synthetic nucleotide sequences. It is understood, furthermore, that the nucleotide sequences may also be subsequently modified, for example by the techniques of genetic engineering, in order to obtain derivatives or variants of the said sequences.

Fluorescence In Situ Hybridization (FISH) Analysis.

Standard culture and preparation procedures are used to obtain metaphase and interphase nuclei from cultured cells derived from animals carrying the desirable transgene. Nuclei are deposited onto slides and were hybridized with a digoxigenin-labeled probe derived from a construct containing 8 kb of the genomic sequence for the bi-functional protein of interest. Bound probe was amplified using a horseradish peroxidase-conjugated antibody and detected with tyramide-conjugated fluorescein isothiocyanate (FITC, green fluorochrome). Nuclei were counterstained with 4',6-diamidino-2-phenylindole (DAPI, blue dye). FISH images were obtained using MetaMorph software.

Therapeutic Compositions.

The proteins of the present invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in order to form a pharmaceutically acceptable composition suitable for effective administration, such compositions will contain an effective amount of one or more of the proteins of the present invention, together with a suitable amount of carrier vehicle.

Pharmaceutical compositions for use in accordance with the present invention may be formulated in conventional manner using one or more physiologically acceptable carriers or excipients. Thus, the bi-functional molecules and their physiologically acceptable salts and solvate may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the composition may take the form of tablets or lozenges formulated in conventional manner.

For administration by inhalation, the bi-functional molecules for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethan- e, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The bi-functional fusion proteins of the invention may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain 1 formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the bi-functional molecules may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Some fusion protein compositions of the current invention may be therapeutically useful in cancer treatment. Therefore they may be formulated in conjunction with conventional chemotherapeutic agents. Conventional chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubicin, daunorubicin, mitomycin, cisplatin, hydroxyurea, prednisone, hydroxyprogesterone caproate, medroxyprogesterone, megestrol acetate, diethyl stilbestrol, ethinyl estradiol, tamoxifen, testosterone propionate and fluoxymesterone. In treating breast cancer, for example, tamoxifen is preferred.

Treatment Methods.

The inventive therapeutic methods according to the invention generally utilize the bi-functional proteins identified above. The domains of the fusion proteins share the ability to specifically target a specific tissue and/or augment an immune response to targeted tissue. A typical method, accordingly, involves binding a receptor of a targeted cell to the receptor-antagonizing domain of the fusion protein and/or stimulating a T-cell dependent immune response.

Therapeutic methods involve administering to a subject in need of treatment a therapeutically effective amount of a fusion protein. "Therapeutically effective" is employed here to denote the amount of fusion proteins that are of sufficient quantity to inhibit or reverse a disease condition (e.g., reduce or inhibit cancer growth). Some methods contemplate combination therapy with known cancer medicaments or therapies, for example, chemotherapy (preferably using compounds of the sort listed above) or radiation. The patient may be a human or non-human animal. A patient typically will be in need of treatment when suffering from a cancer characterized by increased levels of receptors that promote cancer maintenance or proliferation.

Administration during in vivotreatment may be by any number of routes, including parenteral and oral, but preferably parenteral. Intracapsular, intravenous, intrathecal, and intraperitoneal routes of administration may be employed, generally intravenous is preferred. The skilled artisan will recognize that the route of administration will vary depending on the disorder to be treated.

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the induction or substantial induction of T lymphocyte cytotoxicity at the targeted tissue or a decrease in mass of the targeted tissue. Suitable dosages can be from about 1 mg/kg to 10 mg/kg.

Screening Assays to Determine the Biological Activities of Fusion Proteins.

The present invention also provides cell-based assay systems that can be used to compare the biological activities of each of the polypeptide domains of a given fusion protein of the invention. To this end, a cell proliferation assay is used to ensure that the fused domains of the fusion protein each retain a biological function similar to the native protein when it is not fused (i.e. not part of a fusion protein).

In one embodiment, the biological activity of the fusion protein will be determined by introducing the protein to two separate types of cell lines in vitro: each cell line determining the activity of a specific domain. For example, a cell line that is a reliable indicator of the biological activities of a first polypeptide domain should be used to test the effects of that domain, while a cell line capable of indicating the biological effect of a second polypeptide domain should be used to monitor the activity of the other domain. This will also help determine synergistic effects and additive effects of the two functional fusion protein domains. The following examples are illustrative and should not be considered limiting The AFP-fusion transgene construct may be carried within a circular plasmid, a cosmid vector, or other vector, such as a vector derived from a virus. The vector may contain additional sequences that facilitate its propagation in prokaryotic and eukaryotic cells, for example, drug-selectable markers (e.g., for ampicillin resistance in *E. coli*, or G-418 resistance in mammalian cells) and origins of replication (e.g., colE1 for replication in prokaryotic cells, and oriP for replication in mammalian cells).

EXAMPLE 3

Purifying the Fusion Protein

To obtain an increased yield of fusion proteins, it is desired to first purify them, according to procedures that are well known in the art. These steps include: collecting the milk from a transgenic animal or removing the cells from culture via centrifugation, followed by precipitation, tangential flow filtration, and chromatography methodologies, such as low pressure SEC and preparative RP-HPLC chromatography. These steps are followed by: buffer exchange, depyrogenation, and lyophilization.

The foregoing is not intended to have identified all of the aspects or embodiments of the invention nor in any way to limit the invention. The accompanying drawings, which are incorporated and constitute part of the specification, illustrate embodiments of the invention, and together with the description, serve to explain the principles of the invention.

All publications and patent applications mentioned in this specification are herein incorporated by reference to the same extent as if each independent publication or patent application is specifically indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

LITERATURE CITED AND INCORPORATED BY REFERENCE

1. Baguisi A, (1999) et al., *Production of Goats by Somatic Cell Nuclear Transfer,* NATURE BIOTECH; 17: 456-461.
2. Cibelli J B, (1998) et al., *Cloned Transgenic Calves Produced From Nonquiescent Fetal Fibroblasts.* SCIENCE; 280: 1256-1258.
3. Eipper B A, et al., *Peptidylglycine alpha-Amidating Monooxygenase: A Multifunctional Protein with Catalytic, Processing and Routing Domains,* (1993) PROTEIN SCIENCE 2, 489-497).
4. Eppstein et al., BIOCHEMICAL AND BIOPHYSICAL RESEARCH COMMUNICATIONS, 120:66-73 (1984).
5. Hwang, H.-Y, et al., (1996). *Creation of Homozygous Mutants of Leishmania Donovani With Single Targeting Constructs.* J. BIOL. CHEM. 271: 30840-30846.
6. Jain, M, et al., (2001). *Targeted Inactivation of Gal Does Not Alter Cardiac Function or β-Adrenergic Sensitivity.* AM. J. PHYSIOL. 280: 569H-575.
7. Kanehisa (1984) NUC. ACIDS RES. 12:203-213.
8. Kasinathan P, (2001) et al., *Effect of Fibroblast Donor Cell Age and Cell Cycle on Development of Bovine Nuclear Transfer Embryos In Vitro,* BIOL REPROD.; 64(5): 1487-1493.
9. Kasinathan P, (2001) et al., *Production of Calves from G1 Fibroblasts,* NATURE BIOTECH; 19: 1176-1178.
10. Kerr et al., NAT. BIOTECHNOL. 16:75-79, 1998.
11. Lim, S, et al., (1997). *A Shortened Life Span of EKLF-/- Adult Erythrocytes, Due to a Deficiency of Beta-Globin Chains, is Ameliorated by Human Gamma-Globin Chains.* BLOOD 90: 1291-1299.
12. Meng L, et al., (1997) *Rhesus Monkeys Produced by Nuclear Transfer,* BIOL REPROD. August; 57(2):454-9.
13. Mortensen, R, et al., (1992) *Production of Homozygous Mutant ES Cells with a Single Targeting Construct.* MOL. CELL. BIOL. 12, 2391-2395.
14. Nagy, A, et al., (1996) *Targeted Mutagenesis: Analysis of Phenotype Without Germ-Line Transmission.* J. CLIN. INVEST. 97: 1360-1365.
15. Ongeri E M, et al., (2001) *Development of Goat Embryos After In Vitro Fertilization and Parthenogenetic Activation by Different Methods,* THERIOGENOLOGY June 1;55(9):1933-45.
16. Paris et al., BIOTECHNOL. APPL. BIOCHEM. 12:436-449 (1990).
17. REMINGTON'S PHARMACEUTICAL SCIENCES (16$^{th}$ ed., Osol, A., editor., Mack, Easton Press. (1980)).
18. Sakai, E, et al., (1999). *Recombination And Transcription of The Endogenous Ig Heavy Chain Locus Is Effected by the Ig Heavy Chain Intronic Enhancer Core Region In the Absence of the Matrix Attachment Regions.* PROC. NATL. ACAD. SCI. U.S.A. 96: 1526-1531.
19. Sambrook et al., MOLECULAR CLONING—A LABORATORY MANUAL, Cold Spring Harbor Laboratory Press, (2nd Edition) 1989).
20. Watson et al. (1987) in THE MOLECULAR BIOLOGY OF THE GENE (4th ed.) vols. 1&2, Benjamin, Menlo Park, Calif
21. Wilmut I, et al., (2002) *Somatic Cell Nuclear Transfer,* NATURE October 10;419(6907):583-6.
22. Wilmut I, et al., (1997) *Viable Offspring Derived From Fetal and Adult Mammalian Cells,* NATURE February 27;385(6619):810-3.
23. Wold F., et al., *In vivo Chemical Modification of Proteins,* ANN. REV. BIOCHEM. 50 783-814 (1981).
24. Wright et al., *High Level Expression of Active Human alpha-1-Antitrypsin in the Milk of Transgenic Sheep,* (1991) BIO/TECHNOLOGY, 9 77-84.
25. Yong Z and L Yuqiang, (1998) *Nuclear-Cytoplasmic Interaction and Development of Goat Embryos Reconstructed by Nuclear Transplantation: Production of Goats by Serially Cloning Embryos,* BIOL REPROD.; 58: 266-269.
26. Zou X, et al.,(2002) *Generation of Cloned Goats (Capra Hircus) From Transfected Foetal Fibroblast Cells, The Effect of Donor Cell Cycle,* MOL REPROD DEV.; 61: 164-172.

PATENTS CITED AND INCORPORATED BY REFERENCE

1. Meade et al., TRANSGENIC NONHUMAN MAMMAL MILK, U.S. Pat. No. 5,750,172; Issued: May 12, 1998.
2. Meade et al., ISOLATION OF EXOGENOUS RECOMBINANT PROTEINS FROM THE MILK OF TRANSGENIC MAMMALS, U.S. Pat. No. 4,873,316; Issued: Oct. 10, 1989.
3. Stice et al., CLONING USING DONOR NUCLEI FROM PROLIFERA TING SOMATIC CELLS; U.S. Pat. No. 5,945,577; Issued: Aug. 31, 1999.
4. Hurwitz et al., U.S. Pat. No. 5,648,243
5. Meade, et al., U.S. Pat. No. 5,827,690
6. DiTullio et al., U.S. Pat. No. 5,843,705
7. Clark et al., U.S. Pat. No. 5,322,775
8. Garner et al., U.S. Pat. No. 5,639,940
9. Deboer et al., U.S. Pat. No. 5,633,076
10. Drohan et al., U.S. Pat. No. 5,589,604

What is claimed is:

1. A bifunctional fusion protein, encoded by a transgene DNA construct, comprising a human alpha-fetoprotein and human interferon-beta (IFN-β).

2. The fusion protein of claim 1, wherein said fusion protein is the product of a contiguous coding sequence of DNA.

3. The fusion protein of claim 1, further comprising a glutathione S-transferase polypeptide sequence.

4. An isolated polynucleotide encoding a bifunctional fusion protein with the amino acid sequence shown in SEQ ID NO: 4 linked to SEQ ID NO: 10.

5. A recombinant DNA vector comprising the nucleic acid sequence of the fusion protein of claim 1.

6. A host cell transformed with said recombinant DNA vector of claim 5.

7. A recombinant DNA vector comprising the nucleic acid sequence of the fusion protein of claim 1, wherein said vector is an expression vector comprising a promoter operably linked to the nucleic acid sequence.

8. The fusion protein of claim 1, wherein said DNA construct encoding said fusion protein is actuated by at least one beta-casein promoter.

9. A fusion protein produced by a method comprising:
   (a) expressing the fusion protein of claim 1 by a cell; and
   (b) recovering the protein.

10. The fusion protein of claim 9, wherein said fusion protein further comprises an N-terminal methionine.

11. The fusion protein of claim 9, wherein said fusion protein is expressed by a prokaryotic cell.

12. The fusion protein of claim 9, wherein said fusion protein is expressed by a bacteria.

13. The fusion protein of claim 9, wherein said fusion protein is expressed by a eukaryotic cell.

14. The fusion protein of claim 9, wherein said fusion protein is expressed by an animal cell.

15. The fusion protein of claim 14, wherein said animal cell is a CHO cell.

16. The fusion protein of claim 14, wherein said animal cell is a COS cell.

17. The fusion protein of claim 9, wherein said fusion protein is expressed by a yeast.

18. The fusion protein of claim 17, wherein said yeast is *Saccharomyces*.

19. The fusion protein of claim 1, wherein said fusion protein further comprises a peptide linker.

20. The fusion protein of claim 1, wherein said fusion protein comprises a secretion signal sequence.

21. The fusion protein of claim 1, wherein said human IFN-β is fused to the N-terminal end of said human alpha-fetoprotein.

22. The fusion protein of claim 1, wherein said human IFN-β is fused to the C-terminal end of said human alpha-fetoprotein.

23. The fusion protein of claim 1, wherein said fusion protein further comprises an amino acid linking sequence.

* * * * *

UNITED STATES PATENT AND TRADEMARK OFFICE
CERTIFICATE OF CORRECTION

| | | |
|---|---|---|
| PATENT NO. | : 7,550,263 B2 | Page 1 of 1 |
| APPLICATION NO. | : 10/933854 | |
| DATED | : June 23, 2009 | |
| INVENTOR(S) | : Meade et al. | |

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 451 days Delete the phrase "by 451 days" and insert -- by 887 days --

Signed and Sealed this

Thirteenth Day of April, 2010

David J. Kappos
*Director of the United States Patent and Trademark Office*

SEQUENCE LISTING

```
<160> NUMBER OF SEQ ID NOS: 35

<210> SEQ ID NO 1
<211> LENGTH: 2029
<212> TYPE: DNA
<213> ORGANISM: Homo sapiens
<220> FEATURE:
```

<221> NAME/KEY: misc_feature
<223> OTHER INFORMATION: Human Alpha Fetoprotein cDNA
<300> PUBLICATION INFORMATION:
<308> DATABASE ACCESSION NUMBER: Genbank/Accession No. V01514
<309> DATABASE ENTRY DATE: 2002-01-11
<313> RELEVANT RESIDUES: (1)..(2029)

<400> SEQUENCE: 1

```
atattgtgct tccaccactg ccaataacaa ataactagc aaccatgaag tgggtggaat      60
caatttttt aatttttccta ctaaatttta ctgaatccag aacactgcat agaaatgaat     120
atggaatagc ttccatattg gattcttacc aatgtactgc agagataagt ttagctgacc    180
tggctaccat atttttttgcc cagtttgttc aagaagccac ttacaaggaa gtaagcaaaa   240
tggtgaaaga tgcattgact gcaattgaga acccactgg agatgaacag tcttcagggt    300
gtttagaaaa ccagctacct gcctttctgg aagaactttg ccatgagaaa gaaattttgg   360
agaagtacgg acattcagac tgctgcagcc aaagtgaaga gggaagacat aactgttttc   420
ttgcacacaa aaagcccact ccagcatcga tcccactttt ccaagttcca gaacctgtca   480
caagctgtga agcatatgaa gaagacaggg agacattcat gaacaaattc atttatgaga   540
tagcaagaag gcatcccttc ctgtatgcac ctacaattct tctttgggct gctcgctatg   600
acaaaataat tccatcttgc tgcaaagctg aaaatgcagt tgaatgcttc caaacaaagg   660
cagcaacagt tacaaaagaa ttaagagaaa gcagcttgtt aaatcaacat gcatgtgcag   720
taatgaaaaa ttttgggacc cgaactttcc aagccataac tgttactaaa ctgagtcaga   780
agtttaccaa agttaatttt actgaaatcc agaaactagt cctggatgtg gcccatgtac   840
atgagcactg ttgcagagga gatgtgctgg attgtctgca ggatggggaa aaaatcatgt   900
cctacatatg ttctcaacaa gacactctgt caaacaaaat aacagaatgc tgcaaactga   960
ccacgctgga acgtggtcaa tgtataattc atgcagaaaa tgatgaaaaa cctgaaggtc   1020
tatctccaaa tctaaacagg ttttaggag atagagattt taaccaattt tcttcagggg   1080
aaaaaaatat cttcttggca agttttgttc atgaatattc aagaagacat cctcagcttg   1140
ctgtctcagt aattctaaga gttgctaaag gataccagga gttattggag aagtgttttcc  1200
agactgaaaa ccctcttgaa tgccaagata aggagaaga gaattacag aaatacatcc     1260
aggagagcca agcattggca aagcgaagct gcggcctctt ccagaaacta ggagaatatt   1320
acttacaaaa tgcgtttctc gttgcttaca caaagaaagc cccccagctg acctcgtcgg   1380
agctgatggc catcaccaga aaaatggcag ccacagcagc cacttgttgc caactcagtg   1440
aggacaaaact attggcctgt ggcgagggag cggctgacat tattatcgga cacttatgta  1500
tcagacatga aatgactcca gtaaaccctg tgttggcca gtgctgcact tcttcatatg   1560
ccaacaggag gccatgcttc agcagcttgg tggtggatga acatatgtc cctcctgcat    1620
tctctgatga caagttcatt ttccataagg atctgtgcca agctcagggt gtagcgctgc   1680
aaacgatgaa gcaagagttt ctcattaacc ttgtgaagca aaagccacaa ataacagagg   1740
aacaacttga ggctgtcatt gcagatttct caggcctgtt ggagaaatgc tgccaaggcc   1800
aggaacagga agtctgcttt gctgaagagg acaaaaact gatttcaaaa actcgtgctg    1860
ctttgggagt ttaaaattact tcaggggaag agaagacaaa acgagtcttt cattcggtgt    1920
gaacttttct ctttaatttt aactgattta acacttttg tgaattaatg aaatgataaa   1980
gactttatg tgagatttcc ttatcacaga aataaaatat ctccaaatg               2029
```

<210> SEQ ID NO 2

<211> LENGTH: 609
<212> TYPE: PRT
<213> ORGANISM: Homo sapiens
<220> FEATURE:
<221> NAME/KEY: misc_feature
<223> OTHER INFORMATION: Human Alpha Fetoprotein
<300> PUBLICATION INFORMATION:
<308> DATABASE ACCESSION NUMBER: Genbank/Accession No. V01514
<309> DATABASE ENTRY DATE: 1995-03-30
<313> RELEVANT RESIDUES: (1)..(609)

<400> SEQUENCE: 2

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350
```

-continued

```
Ser Phe Val His Glu Tyr Ser Arg Arg His Pro Gln Leu Ala Val Ser
            355                 360                 365
Val Ile Leu Arg Val Ala Lys Gly Tyr Gln Glu Leu Leu Glu Lys Cys
        370                 375                 380
Phe Gln Thr Glu Asn Pro Leu Glu Cys Gln Asp Lys Gly Glu Glu Glu
385                 390                 395                 400
Leu Gln Lys Tyr Ile Gln Glu Ser Gln Ala Leu Ala Lys Arg Ser Cys
                405                 410                 415
Gly Leu Phe Gln Lys Leu Gly Glu Tyr Tyr Leu Gln Asn Ala Phe Leu
            420                 425                 430
Val Ala Tyr Thr Lys Lys Ala Pro Gln Leu Thr Ser Ser Glu Leu Met
        435                 440                 445
Ala Ile Thr Arg Lys Met Ala Ala Thr Ala Thr Cys Cys Gln Leu
    450                 455                 460
Ser Glu Asp Lys Leu Leu Ala Cys Gly Glu Gly Ala Ala Asp Ile Ile
465                 470                 475                 480
Ile Gly His Leu Cys Ile Arg His Glu Met Thr Pro Val Asn Pro Gly
                485                 490                 495
Val Gly Gln Cys Cys Thr Ser Ser Tyr Ala Asn Arg Arg Pro Cys Phe
            500                 505                 510
Ser Ser Leu Val Val Asp Glu Thr Tyr Val Pro Pro Ala Phe Ser Asp
        515                 520                 525
Asp Lys Phe Ile Phe His Lys Asp Leu Cys Gln Ala Gln Gly Val Ala
    530                 535                 540
Leu Gln Thr Met Lys Gln Glu Phe Leu Ile Asn Leu Val Lys Gln Lys
545                 550                 555                 560
Pro Gln Ile Thr Glu Glu Gln Leu Glu Ala Val Ile Ala Asp Phe Ser
                565                 570                 575
Gly Leu Leu Glu Lys Cys Cys Gln Gly Gln Glu Gln Glu Val Cys Phe
            580                 585                 590
Ala Glu Glu Gly Gln Lys Leu Ile Ser Lys Thr Arg Ala Ala Leu Gly
        595                 600                 605
Val
```

<210> SEQ ID NO 3
<211> LENGTH: 1776
<212> TYPE: PRT
<213> ORGANISM: Homo sapiens
<300> PUBLICATION INFORMATION:
<308> DATABASE ACCESSION NUMBER: Genbank Accession No. V01514
<309> DATABASE ENTRY DATE: 2002-01-11
<313> RELEVANT RESIDUES: (99)..(1874)

<400> SEQUENCE: 3

```
Ala Gly Ala Ala Cys Ala Cys Thr Gly Cys Ala Thr Ala Gly Ala Ala
1               5                   10                  15
Ala Thr Gly Ala Ala Thr Ala Thr Gly Gly Ala Ala Thr Ala Gly Cys
                20                  25                  30
Thr Thr Cys Cys Ala Thr Ala Thr Gly Gly Ala Thr Thr Cys Thr Thr
        35                  40                  45
Thr Ala Cys Cys Ala Ala Thr Gly Thr Ala Cys Thr Gly Cys Ala Gly
    50                  55                  60
Ala Gly Ala Thr Ala Ala Gly Thr Thr Thr Ala Gly Cys Thr Gly Ala
65                  70                  75                  80
Cys Cys Thr Gly Gly Cys Thr Ala Cys Cys Ala Thr Ala Thr Thr Thr
                85                  90                  95
```

-continued

```
Thr Thr Thr Gly Cys Cys Cys Ala Gly Thr Thr Gly Thr Thr Cys
            100                 105                 110
Ala Ala Gly Ala Ala Gly Cys Cys Ala Cys Thr Thr Ala Cys Ala Ala
            115                 120                 125
Gly Gly Ala Ala Gly Thr Ala Ala Gly Cys Ala Ala Ala Ala Thr Gly
            130                 135                 140
Gly Thr Gly Ala Ala Ala Gly Ala Thr Gly Cys Ala Thr Thr Gly Ala
145                 150                 155                 160
Cys Thr Gly Cys Ala Ala Thr Gly Ala Gly Ala Ala Ala Cys Cys
                165                 170                 175
Cys Ala Cys Thr Gly Gly Ala Gly Ala Thr Gly Ala Ala Cys Ala Gly
                180                 185                 190
Thr Cys Thr Thr Cys Ala Gly Gly Thr Gly Thr Thr Thr Ala Gly
            195                 200                 205
Ala Ala Ala Ala Cys Cys Ala Gly Cys Thr Ala Cys Cys Thr Gly Cys
            210                 215                 220
Cys Thr Thr Thr Cys Thr Gly Gly Ala Ala Gly Ala Ala Cys Thr Thr
225                 230                 235                 240
Thr Gly Cys Cys Ala Thr Gly Ala Gly Ala Ala Ala Gly Ala Ala Ala
                245                 250                 255
Thr Thr Thr Thr Gly Gly Ala Gly Ala Ala Gly Thr Ala Cys Gly Gly
            260                 265                 270
Ala Cys Ala Thr Thr Cys Ala Gly Ala Cys Thr Gly Cys Thr Gly Cys
            275                 280                 285
Ala Gly Cys Cys Ala Ala Ala Gly Thr Gly Ala Ala Gly Ala Gly Gly
            290                 295                 300
Gly Ala Ala Gly Ala Cys Ala Thr Ala Ala Cys Thr Gly Thr Thr Thr
305                 310                 315                 320
Thr Cys Thr Thr Gly Cys Ala Cys Ala Cys Ala Ala Ala Ala Ala Gly
                325                 330                 335
Cys Cys Cys Ala Cys Thr Cys Ala Gly Cys Ala Thr Cys Gly Ala
            340                 345                 350
Thr Cys Cys Cys Ala Cys Thr Thr Thr Cys Cys Ala Ala Gly Thr
            355                 360                 365
Thr Cys Cys Ala Gly Ala Cys Cys Thr Gly Thr Cys Ala Cys Ala
            370                 375                 380
Ala Gly Cys Thr Gly Thr Gly Ala Ala Gly Cys Ala Thr Ala Thr Gly
385                 390                 395                 400
Ala Ala Gly Ala Ala Gly Ala Cys Ala Gly Gly Ala Gly Ala Cys
            405                 410                 415
Ala Thr Thr Cys Ala Thr Gly Ala Ala Cys Ala Ala Thr Thr Cys
            420                 425                 430
Ala Thr Thr Thr Ala Thr Gly Ala Gly Ala Thr Ala Gly Cys Ala Ala
                435                 440                 445
Gly Ala Ala Gly Gly Cys Ala Thr Cys Cys Thr Thr Cys Cys Thr
450                 455                 460
Gly Thr Ala Thr Gly Cys Ala Cys Cys Thr Ala Cys Ala Ala Thr Thr
465                 470                 475                 480
Cys Thr Thr Cys Thr Thr Thr Gly Gly Gly Cys Thr Gly Cys Thr Cys
                485                 490                 495
Gly Cys Thr Ala Thr Gly Ala Cys Ala Ala Ala Ala Thr Ala Ala Thr
                500                 505                 510
```

```
Thr Cys Cys Ala Thr Cys Thr Gly Cys Thr Gly Cys Ala Ala Ala
        515                 520                 525

Gly Cys Thr Gly Ala Ala Ala Ala Thr Gly Cys Ala Gly Thr Thr Gly
        530                 535                 540

Ala Ala Thr Gly Cys Thr Thr Cys Cys Ala Ala Cys Ala Ala Ala
545                 550                 555                 560

Gly Gly Cys Ala Gly Cys Ala Ala Cys Ala Gly Thr Thr Ala Cys Ala
                565                 570                 575

Ala Ala Ala Gly Ala Ala Thr Thr Ala Ala Gly Ala Gly Ala Ala Ala
                580                 585                 590

Gly Cys Ala Gly Cys Thr Thr Gly Thr Thr Ala Ala Thr Cys Ala
        595                 600                 605

Ala Cys Ala Thr Gly Cys Ala Thr Gly Thr Gly Cys Ala Gly Thr Ala
        610                 615                 620

Ala Thr Gly Ala Ala Ala Ala Thr Thr Thr Gly Gly Gly Ala
625                 630                 635                 640

Cys Cys Cys Gly Ala Ala Cys Thr Thr Thr Cys Cys Ala Ala Gly Cys
                645                 650                 655

Cys Ala Thr Ala Ala Cys Thr Gly Thr Thr Ala Cys Thr Ala Ala Ala
                660                 665                 670

Cys Thr Gly Ala Gly Thr Cys Ala Gly Ala Ala Gly Thr Thr Thr Ala
                675                 680                 685

Cys Cys Ala Ala Ala Gly Thr Thr Ala Ala Thr Thr Thr Thr Ala Cys
                690                 695                 700

Thr Gly Ala Ala Ala Thr Cys Cys Ala Gly Ala Ala Ala Cys Thr Ala
705                 710                 715                 720

Gly Thr Cys Cys Thr Gly Gly Ala Thr Gly Thr Gly Gly Cys Cys Cys
                725                 730                 735

Ala Thr Gly Thr Ala Cys Ala Thr Gly Ala Gly Cys Ala Cys Thr Gly
                740                 745                 750

Thr Thr Gly Cys Ala Gly Ala Gly Gly Ala Gly Ala Thr Gly Thr Gly
                755                 760                 765

Cys Thr Gly Gly Ala Thr Thr Gly Thr Cys Thr Gly Cys Ala Gly Gly
        770                 775                 780

Ala Thr Gly Gly Gly Gly Ala Ala Ala Ala Ala Thr Cys Ala Thr
785                 790                 795                 800

Gly Thr Cys Cys Thr Ala Cys Ala Thr Ala Thr Gly Thr Thr Cys Thr
                805                 810                 815

Cys Ala Ala Cys Ala Ala Gly Ala Cys Ala Cys Thr Cys Thr Gly Thr
                820                 825                 830

Cys Ala Ala Ala Cys Ala Ala Ala Thr Ala Cys Ala Gly Ala
                835                 840                 845

Ala Thr Gly Cys Thr Gly Cys Ala Ala Ala Cys Thr Gly Ala Cys Cys
        850                 855                 860

Ala Cys Gly Cys Thr Gly Gly Ala Ala Cys Gly Thr Gly Gly Thr Cys
865                 870                 875                 880

Ala Ala Thr Gly Thr Ala Thr Ala Ala Thr Thr Cys Ala Thr Gly Cys
                885                 890                 895

Ala Gly Ala Ala Ala Thr Gly Ala Thr Gly Ala Ala Ala Ala
                900                 905                 910

Cys Cys Thr Gly Ala Ala Gly Gly Thr Cys Thr Ala Thr Cys Thr Cys
                915                 920                 925

Cys Ala Ala Ala Thr Cys Thr Ala Ala Ala Cys Ala Gly Gly Thr Thr
```

-continued

|  | 930 |  |  | 935 |  |  | 940 |  |  |  |  |
|---|---|---|---|---|---|---|---|---|---|---|---|
| Thr | Thr | Thr | Ala | Gly | Gly | Ala | Gly | Ala | Thr | Ala | Gly | Ala | Gly | Ala | Thr |
| 945 | | | | 950 | | | | 955 | | | | 960 |

Thr Thr Thr Ala Ala Cys Cys Ala Ala Thr Thr Thr Cys Thr Thr
                965              970              975

Cys Ala Gly Gly Gly Gly Ala Ala Ala Ala Ala Ala Thr Ala Thr
        980              985              990

Cys Thr Thr Cys Thr Thr Gly Gly Cys Ala Ala Gly Thr Thr Thr Thr
        995            1000           1005

Gly Thr Thr Cys Ala Thr Gly Ala Ala Thr Ala Thr Thr Cys Ala
    1010              1015           1020

Ala Gly Ala Ala Gly Ala Cys Ala Thr Cys Cys Thr Cys Ala Gly
    1025              1030           1035

Cys Thr Thr Gly Cys Thr Gly Thr Cys Thr Cys Ala Gly Thr Ala
    1040              1045           1050

Ala Thr Thr Cys Thr Ala Ala Gly Ala Gly Thr Thr Gly Cys Thr
    1055              1060           1065

Ala Ala Ala Gly Gly Ala Thr Ala Cys Cys Ala Gly Gly Ala Gly
    1070              1075           1080

Thr Thr Ala Thr Thr Gly Gly Ala Gly Ala Ala Gly Thr Gly Thr
    1085              1090           1095

Thr Thr Cys Cys Ala Gly Ala Cys Thr Gly Ala Ala Ala Ala Cys
    1100              1105           1110

Cys Cys Thr Cys Thr Thr Gly Ala Ala Thr Gly Cys Cys Ala Ala
    1115              1120           1125

Gly Ala Thr Ala Ala Ala Gly Ala Gly Ala Ala Gly Ala Ala
    1130              1135           1140

Gly Ala Ala Thr Thr Ala Cys Ala Gly Ala Ala Ala Thr Ala Cys
    1145              1150           1155

Ala Thr Cys Cys Ala Gly Gly Ala Gly Ala Gly Cys Cys Ala Ala
    1160              1165           1170

Gly Cys Ala Thr Thr Gly Gly Cys Ala Ala Ala Gly Cys Gly Ala
    1175              1180           1185

Ala Gly Cys Thr Gly Cys Gly Gly Cys Cys Thr Cys Thr Thr Cys
    1190              1195           1200

Cys Ala Gly Ala Ala Ala Cys Thr Ala Gly Gly Ala Gly Ala Ala
    1205              1210           1215

Thr Ala Thr Thr Ala Cys Thr Thr Ala Cys Ala Ala Ala Ala Thr
    1220              1225           1230

Gly Cys Gly Thr Thr Thr Cys Thr Cys Gly Thr Thr Gly Cys Thr
    1235              1240           1245

Thr Ala Cys Ala Cys Ala Ala Ala Gly Ala Ala Ala Gly Cys Cys
    1250              1255           1260

Cys Cys Cys Cys Ala Gly Cys Thr Gly Ala Cys Cys Thr Cys Gly
    1265              1270           1275

Thr Cys Gly Gly Ala Gly Cys Thr Gly Ala Thr Gly Gly Cys Cys
    1280              1285           1290

Ala Thr Cys Ala Cys Ala Gly Ala Ala Ala Ala Thr Gly
    1295              1300           1305

Gly Cys Ala Gly Cys Cys Ala Cys Ala Gly Cys Ala Gly Cys Cys
    1310              1315           1320

Ala Cys Thr Thr Gly Thr Thr Gly Cys Cys Ala Ala Cys Thr Cys
    1325              1330           1335

-continued

```
Ala Gly Thr Gly Ala Gly Gly Ala Cys Ala Ala Cys Thr Ala
    1340                1345                1350

Thr Thr Gly Gly Cys Cys Thr Gly Thr Gly Cys Gly Ala Gly
    1355                1360                1365

Gly Gly Ala Gly Cys Gly Gly Cys Thr Gly Ala Cys Ala Thr Thr
    1370                1375                1380

Ala Thr Thr Ala Thr Cys Gly Gly Ala Cys Ala Cys Thr Thr Ala
    1385                1390                1395

Thr Gly Thr Ala Thr Cys Ala Gly Ala Cys Ala Thr Gly Ala Ala
    1400                1405                1410

Ala Thr Gly Ala Cys Thr Cys Cys Ala Gly Thr Ala Ala Ala Cys
    1415                1420                1425

Cys Cys Thr Gly Gly Thr Gly Thr Thr Gly Gly Cys Cys Ala Gly
    1430                1435                1440

Thr Gly Cys Thr Gly Cys Ala Cys Thr Thr Cys Thr Thr Cys Ala
    1445                1450                1455

Thr Ala Thr Gly Cys Cys Ala Ala Cys Ala Gly Gly Ala Gly Gly
    1460                1465                1470

Cys Cys Ala Thr Gly Cys Thr Thr Cys Ala Gly Cys Ala Gly Cys
    1475                1480                1485

Thr Thr Gly Gly Thr Gly Gly Thr Gly Gly Ala Thr Gly Ala Ala
    1490                1495                1500

Ala Cys Ala Thr Ala Thr Gly Thr Cys Cys Cys Thr Cys Cys Thr
    1505                1510                1515

Gly Cys Ala Thr Cys Thr Cys Thr Gly Ala Thr Gly Ala Cys
    1520                1525                1530

Ala Ala Gly Thr Thr Cys Ala Thr Thr Thr Thr Cys Cys Ala Thr
    1535                1540                1545

Ala Ala Gly Gly Ala Thr Cys Thr Gly Thr Gly Cys Cys Ala Ala
    1550                1555                1560

Gly Cys Thr Cys Ala Gly Gly Gly Thr Gly Thr Ala Gly Cys Gly
    1565                1570                1575

Cys Thr Gly Cys Ala Ala Ala Cys Gly Ala Thr Gly Ala Ala Gly
    1580                1585                1590

Cys Ala Ala Gly Ala Gly Thr Thr Thr Cys Thr Cys Ala Thr Thr
    1595                1600                1605

Ala Ala Cys Cys Thr Thr Gly Thr Gly Ala Ala Gly Cys Ala Ala
    1610                1615                1620

Ala Ala Gly Cys Cys Ala Cys Ala Ala Ala Thr Ala Ala Cys Ala
    1625                1630                1635

Gly Ala Gly Gly Ala Ala Cys Ala Ala Cys Thr Ala Gly Ala Gly
    1640                1645                1650

Gly Cys Thr Gly Thr Cys Ala Thr Thr Gly Cys Ala Gly Ala Thr
    1655                1660                1665

Thr Thr Cys Thr Cys Ala Gly Gly Cys Cys Thr Gly Thr Thr Gly
    1670                1675                1680

Gly Ala Gly Ala Ala Ala Thr Gly Cys Thr Gly Cys Cys Ala Ala
    1685                1690                1695

Gly Gly Cys Cys Ala Gly Gly Ala Ala Cys Ala Gly Gly Ala Ala
    1700                1705                1710

Gly Thr Cys Thr Gly Cys Thr Thr Thr Gly Cys Thr Gly Ala Ala
    1715                1720                1725
```

-continued

```
Gly Ala Gly Gly Gly Ala Cys Ala Ala Ala Ala Cys Thr Gly
    1730                1735                1740

Ala Thr Thr Thr Cys Ala Ala Ala Ala Cys Thr Cys Gly Thr
    1745                1750                1755

Gly Cys Thr Gly Cys Thr Thr Thr Gly Gly Gly Ala Gly Thr Thr
    1760                1765                1770

Thr Ala Ala
    1775

<210> SEQ ID NO 4
<211> LENGTH: 591
<212> TYPE: PRT
<213> ORGANISM: Homo sapiens
<220> FEATURE:
<221> NAME/KEY: misc_feature
<223> OTHER INFORMATION: Human Alpha Fetoprotein
<300> PUBLICATION INFORMATION:
<308> DATABASE ACCESSION NUMBER: Genbank/Accession No. V01514
<309> DATABASE ENTRY DATE: 1995-03-30
<313> RELEVANT RESIDUES: (19)..(609)

<400> SEQUENCE: 4

Arg Thr Leu His Arg Asn Glu Tyr Gly Ile Ala Ser Ile Leu Asp Ser
1               5                   10                  15

Tyr Gln Cys Thr Ala Glu Ile Ser Leu Ala Asp Leu Ala Thr Ile Phe
            20                  25                  30

Phe Ala Gln Phe Val Gln Glu Ala Thr Tyr Lys Glu Val Ser Lys Met
        35                  40                  45

Val Lys Asp Ala Leu Thr Ala Ile Glu Lys Pro Thr Gly Asp Glu Gln
    50                  55                  60

Ser Ser Gly Cys Leu Glu Asn Gln Leu Pro Ala Phe Leu Glu Glu Leu
65                  70                  75                  80

Cys His Glu Lys Glu Ile Leu Glu Lys Tyr Gly His Ser Asp Cys Cys
                85                  90                  95

Ser Gln Ser Glu Glu Gly Arg His Asn Cys Phe Leu Ala His Lys Lys
            100                 105                 110

Pro Thr Pro Ala Ser Ile Pro Leu Phe Gln Val Pro Glu Pro Val Thr
        115                 120                 125

Ser Cys Glu Ala Tyr Glu Glu Asp Arg Glu Thr Phe Met Asn Lys Phe
    130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
            180                 185                 190

Lys Glu Leu Arg Glu Ser Ser Leu Leu Asn Gln His Ala Cys Ala Val
        195                 200                 205

Met Lys Asn Phe Gly Thr Arg Thr Phe Gln Ala Ile Thr Val Thr Lys
    210                 215                 220

Leu Ser Gln Lys Phe Thr Lys Val Asn Phe Thr Glu Ile Gln Lys Leu
225                 230                 235                 240

Val Leu Asp Val Ala His Val His Glu His Cys Cys Arg Gly Asp Val
                245                 250                 255

Leu Asp Cys Leu Gln Asp Gly Glu Lys Ile Met Ser Tyr Ile Cys Ser
            260                 265                 270

Gln Gln Asp Thr Leu Ser Asn Lys Ile Thr Glu Cys Cys Lys Leu Thr
```

```
                275                 280                 285
Thr Leu Glu Arg Gly Gln Cys Ile Ile His Ala Glu Asn Asp Glu Lys
    290                 295                 300
Pro Glu Gly Leu Ser Pro Asn Leu Asn Arg Phe Leu Gly Asp Arg Asp
305                 310                 315                 320
Phe Asn Gln Phe Ser Ser Gly Glu Lys Asn Ile Phe Leu Ala Ser Phe
                325                 330                 335
Val His Glu Tyr Ser Arg Arg His Pro Gln Leu Ala Val Ser Val Ile
                340                 345                 350
Leu Arg Val Ala Lys Gly Tyr Gln Glu Leu Leu Glu Lys Cys Phe Gln
                355                 360                 365
Thr Glu Asn Pro Leu Glu Cys Gln Asp Lys Gly Glu Glu Glu Leu Gln
    370                 375                 380
Lys Tyr Ile Gln Glu Ser Gln Ala Leu Ala Lys Arg Ser Cys Gly Leu
385                 390                 395                 400
Phe Gln Lys Leu Gly Glu Tyr Tyr Leu Gln Asn Ala Phe Leu Val Ala
                405                 410                 415
Tyr Thr Lys Lys Ala Pro Gln Leu Thr Ser Ser Glu Leu Met Ala Ile
                420                 425                 430
Thr Arg Lys Met Ala Ala Thr Ala Ala Thr Cys Cys Gln Leu Ser Glu
                435                 440                 445
Asp Lys Leu Leu Ala Cys Gly Glu Gly Ala Ala Asp Ile Ile Ile Gly
    450                 455                 460
His Leu Cys Ile Arg His Glu Met Thr Pro Val Asn Pro Gly Val Gly
465                 470                 475                 480
Gln Cys Cys Thr Ser Ser Tyr Ala Asn Arg Arg Pro Cys Phe Ser Ser
                485                 490                 495
Leu Val Val Asp Glu Thr Tyr Val Pro Pro Ala Phe Ser Asp Asp Lys
                500                 505                 510
Phe Ile Phe His Lys Asp Leu Cys Gln Ala Gln Gly Val Ala Leu Gln
                515                 520                 525
Thr Met Lys Gln Glu Phe Leu Ile Asn Leu Val Lys Gln Lys Pro Gln
    530                 535                 540
Ile Thr Glu Glu Gln Leu Glu Ala Val Ile Ala Asp Phe Ser Gly Leu
545                 550                 555                 560
Leu Glu Lys Cys Cys Gln Gly Gln Glu Gln Glu Val Cys Phe Ala Glu
                565                 570                 575
Glu Gly Gln Lys Leu Ile Ser Lys Thr Arg Ala Ala Leu Gly Val
                580                 585                 590

<210> SEQ ID NO 5
<211> LENGTH: 1830
<212> TYPE: DNA
<213> ORGANISM: Homo sapiens
<220> FEATURE:
<221> NAME/KEY: misc_feature
<223> OTHER INFORMATION: Human Alpha Fetoprotein Fragment
<300> PUBLICATION INFORMATION:
<308> DATABASE ACCESSION NUMBER: Genbank/Accession No. V01514
<309> DATABASE ENTRY DATE: 2002-01-11
<313> RELEVANT RESIDUES: (45)..(1874)

<400> SEQUENCE: 5
atgaagtggg tggaatcaat ttttttaatt ttcctactaa attttactga atccagaaca      60
ctgcatagaa atgaatatgg aatagcttcc atattggatt cttaccaatg tactgcagag     120
ataagtttag ctgacctggc taccatattt tttgcccagt tgttcaaga agccacttac      180
```

-continued

```
aaggaagtaa gcaaaatggt gaaagatgca ttgactgcaa ttgagaaacc cactggagat    240
gaacagtctt cagggtgttt agaaaaccag ctacctgcct ttctggaaga actttgccat    300
gagaaagaaa ttttggagaa gtacggacat tcagactgct gcagccaaag tgaagaggga    360
agacataact gttttcttgc acacaaaaag cccactccag catcgatccc acttttccaa    420
gttccagaac ctgtcacaag ctgtgaagca tatgaagaag acaggagac attcatgaac     480 aaattcattt atgagatagc aagaaggcat cccttcctgt atgcacctac aattcttctt    540
tgggctgctc gctatgacaa ataattcca tcttgctgca aagctgaaaa tgcagttgaa     600
tgcttccaaa caaaggcagc aacagttaca aaagaattaa gagaaagcag cttgttaaat    660
caacatgcat gtgcagtaat gaaaaatttt gggacccgaa ctttccaagc cataactgtt    720
actaaactga gtcagaagtt taccaaagtt aattttactg aaatccagaa actagtcctg    780
gatgtggccc atgtacatga gcactgttgc agaggagatg tgctggattg tctgcaggat    840
ggggaaaaaa tcatgtccta catatgttct caacaagaca ctctgtcaaa caaaataaca    900
gaatgctgca aactgaccac gctggaacgt ggtcaatgta taattcatgc agaaaatgat    960
gaaaaacctg aaggtctatc tccaaatcta aacaggtttt taggagatag agattttaac   1020
caattttctt cagggaaaaa aaatatcttc ttggcaagtt ttgttcatga atattcaaga   1080
agacatcctc agcttgctgt ctcagtaatt ctaagagttg ctaaaggata ccaggagtta   1140
ttggagaagt gtttccagac tgaaaaccct cttgaatgcc aagataaagg agaagaagaa   1200
ttacagaaat acatccagga gagccaagca ttggcaaagc gaagctgcgg cctcttccag   1260
aaactaggag aatattactt acaaaatgcg tttctcgttg cttacacaaa gaaagccccc   1320
cagctgacct cgtcggagct gatggccatc accagaaaaa tggcagccac agcagccact   1380
tgttgccaac tcagtgagga caaactattg gcctgtggcg agggagcggc tgacattatt   1440
atcggacact tatgtatcag acatgaaatg actccagtaa accctggtgt tggccagtgc   1500
tgcacttctt catatgccaa caggaggcca tgcttcagca gcttggtggt ggatgaaaca   1560
tatgtccctc ctgcattctc tgatgacaag ttcattttcc ataaggatct gtgccaagct   1620
cagggtgtag cgctgcaaac gatgaagcaa gagtttctca ttaaccttgt gaagcaaaag   1680
ccacaaataa cagaggaaca acttgaggct gtcattgcag attttctcagg cctgttggag   1740 aaatgctgcc aaggccagga acaggaagtc tgctttgctg aagagggaca aaaactgatt   1800
tcaaaaactc gtgctgcttt gggagtttaa                                   1830
```

<210> SEQ ID NO 6
<211> LENGTH: 591
<212> TYPE: PRT
<213> ORGANISM: Homo sapiens
<220> FEATURE:
<221> NAME/KEY: misc_feature
<223> OTHER INFORMATION: Human Alpha Fetoprotein
<300> PUBLICATION INFORMATION:
<308> DATABASE ACCESSION NUMBER: Genbank/Accession No. V01514
<309> DATABASE ENTRY DATE: 1995-03-30
<313> RELEVANT RESIDUES: (19)..(609)

<400> SEQUENCE: 6

Arg Thr Leu His Arg Asn Glu Tyr Gly Ile Ala Ser Ile Leu Asp Ser
1               5                   10                  15

Tyr Gln Cys Thr Ala Glu Ile Ser Leu Ala Asp Leu Ala Thr Ile Phe
            20                  25                  30

Phe Ala Gln Phe Val Gln Glu Ala Thr Tyr Lys Glu Val Ser Lys Met

-continued

```
                35                  40                  45
Val Lys Asp Ala Leu Thr Ala Ile Glu Lys Pro Thr Gly Asp Glu Gln
 50                  55                  60

Ser Ser Gly Cys Leu Glu Asn Gln Leu Pro Ala Phe Leu Glu Glu Leu
 65                  70                  75                  80

Cys His Glu Lys Glu Ile Leu Glu Lys Tyr Gly His Ser Asp Cys Cys
                 85                  90                  95

Ser Gln Ser Glu Glu Gly Arg His Asn Cys Phe Leu Ala His Lys Lys
                100                 105                 110

Pro Thr Pro Ala Ser Ile Pro Leu Phe Gln Val Pro Glu Pro Val Thr
                115                 120                 125

Ser Cys Glu Ala Tyr Glu Glu Asp Arg Glu Thr Phe Met Asn Lys Phe
130                 135                 140

Ile Tyr Glu Ile Ala Arg Arg His Pro Phe Leu Tyr Ala Pro Thr Ile
145                 150                 155                 160

Leu Leu Trp Ala Ala Arg Tyr Asp Lys Ile Ile Pro Ser Cys Cys Lys
                165                 170                 175

Ala Glu Asn Ala Val Glu Cys Phe Gln Thr Lys Ala Ala Thr Val Thr
                180                 185                 190

Lys Glu Leu Arg Glu Ser Ser Leu Leu Asn Gln His Ala Cys Ala Val
                195                 200                 205

Met Lys Asn Phe Gly Thr Arg Thr Phe Gln Ala Ile Thr Val Thr Lys
                210                 215                 220

Leu Ser Gln Lys Phe Thr Lys Val Gln Phe Thr Glu Ile Gln Lys Leu
225                 230                 235                 240

Val Leu Asp Val Ala His Val His Glu His Cys Cys Arg Gly Asp Val
                245                 250                 255

Leu Asp Cys Leu Gln Asp Gly Glu Lys Ile Met Ser Tyr Ile Cys Ser
                260                 265                 270

Gln Gln Asp Thr Leu Ser Asn Lys Ile Thr Glu Cys Cys Lys Leu Thr
                275                 280                 285

Thr Leu Glu Arg Gly Gln Cys Ile Ile His Ala Glu Asn Asp Glu Lys
                290                 295                 300

Pro Glu Gly Leu Ser Pro Asn Leu Asn Arg Phe Leu Gly Asp Arg Asp
305                 310                 315                 320

Phe Asn Gln Phe Ser Ser Gly Glu Lys Asn Ile Phe Leu Ala Ser Phe
                325                 330                 335

Val His Glu Tyr Ser Arg Arg His Pro Gln Leu Ala Val Ser Val Ile
                340                 345                 350

Leu Arg Val Ala Lys Gly Tyr Gln Glu Leu Leu Glu Lys Cys Phe Gln
                355                 360                 365

Thr Glu Asn Pro Leu Glu Cys Gln Asp Lys Gly Glu Glu Glu Leu Gln
370                 375                 380

Lys Tyr Ile Gln Glu Ser Gln Ala Leu Ala Lys Arg Ser Cys Gly Leu
385                 390                 395                 400

Phe Gln Lys Leu Gly Glu Tyr Tyr Leu Gln Asn Ala Phe Leu Val Ala
                405                 410                 415

Tyr Thr Lys Lys Ala Pro Gln Leu Thr Ser Ser Glu Leu Met Ala Ile
                420                 425                 430

Thr Arg Lys Met Ala Ala Thr Ala Ala Thr Cys Cys Gln Leu Ser Glu
                435                 440                 445

Asp Lys Leu Leu Ala Cys Gly Glu Gly Ala Ala Asp Ile Ile Ile Gly
450                 455                 460
```

```
His Leu Cys Ile Arg His Glu Met Thr Pro Val Asn Pro Gly Val Gly
465                 470                 475                 480

Gln Cys Cys Thr Ser Ser Tyr Ala Asn Arg Arg Pro Cys Phe Ser Ser
            485                 490                 495

Leu Val Val Asp Glu Thr Tyr Val Pro Pro Ala Phe Ser Asp Asp Lys
            500                 505                 510

Phe Ile Phe His Lys Asp Leu Cys Gln Ala Gln Gly Val Ala Leu Gln
        515                 520                 525

Thr Met Lys Gln Glu Phe Leu Ile Asn Leu Val Lys Gln Lys Pro Gln
    530                 535                 540

Ile Thr Glu Glu Gln Leu Glu Ala Val Ile Ala Asp Phe Ser Gly Leu
545                 550                 555                 560

Leu Glu Lys Cys Cys Gln Gly Gln Glu Gln Glu Val Cys Phe Ala Glu
                565                 570                 575

Glu Gly Gln Lys Leu Ile Ser Lys Thr Arg Ala Ala Leu Gly Val
            580                 585                 590

<210> SEQ ID NO 7
<211> LENGTH: 18
<212> TYPE: PRT
<213> ORGANISM: Homo sapiens
<220> FEATURE:
<221> NAME/KEY: misc_feature
<223> OTHER INFORMATION: Human Alpha Fetoprotein
<300> PUBLICATION INFORMATION:
<308> DATABASE ACCESSION NUMBER: Genbank Accession No. V01514
<309> DATABASE ENTRY DATE: 1995-03-30
<313> RELEVANT RESIDUES: (1)..(18)

<400> SEQUENCE: 7

Met Lys Trp Val Glu Ser Ile Phe Leu Ile Phe Leu Leu Asn Phe Thr
1               5                   10                  15

Glu Ser

<210> SEQ ID NO 8
<211> LENGTH: 54
<212> TYPE: DNA
<213> ORGANISM: Homo sapiens
<220> FEATURE:
<221> NAME/KEY: misc_feature
<223> OTHER INFORMATION: Human Alpha Fetoprotein Fragment
<300> PUBLICATION INFORMATION:
<308> DATABASE ACCESSION NUMBER: Genbank/Accession No. V01514
<309> DATABASE ENTRY DATE: 2002-01-11
<313> RELEVANT RESIDUES: (45)..(98)

<400> SEQUENCE: 8
atgaagtggg tggaatcaat ttttttaatt ttcctactaa attttactga atcc            54

<210> SEQ ID NO 9
<211> LENGTH: 27553
<212> TYPE: DNA
<213> ORGANISM: Homo sapiens
<220> FEATURE:
<221> NAME/KEY: misc_feature
<223> OTHER INFORMATION: Human Alpha Fetoprotein Genomic DNA Sequence
<300> PUBLICATION INFORMATION:
<308> DATABASE ACCESSION NUMBER: Genbank/Accession No. M16110
<309> DATABASE ENTRY DATE: 1997-06-03
<313> RELEVANT RESIDUES: (1)..(27553)

<400> SEQUENCE: 9
gaattcccaa tatctagtat tttctactat taaactttgt gcctcttcaa aactgcattt      60
```

```
tctctcattc cctaagtgtg cattgttttc ccttaccggt tggttttcc accacctttt      120 acatttcct ggaacactat accctccctc ttcatttggc ccacctctaa ttttctttca      180
gatctccatg aagatgttac ttcctccagg aagccttatc tgacccctcc aaagatgtca    240
tgagttcctc ttttcattct actaatcaca gcatccatca caccatgttg tgattactga    300
tactattgtc tgtttctctg attaggcagt aagctcaaca agagctacat ggtgcctgtc    360
tcttgttgct gattattccc atccaaaaac agtgcctgga atgcagactt aacattttat    420
tgaatgaata ataaaaccc catctatcga gtgctacttt gtgcaagacc cggttctgag     480
gcatttatat ttattgattt atttaattct catttaacca tgaaggaggt actatcacta    540
tccttatttt atagttgata aagataaagc ccagagaaat gaattaactc acccaaagtc    600
atgtagctaa gtgacagggc aaaaattcaa accagttccc caactttacg tgattaatac    660
tgtgctatac tgcctctctg atcatatggc atggaatgca gacatctgct ccgtaaggca    720
gaatatggaa ggagattgga ggatgacaca aaaccagcat aatatcagag aaaagtcca    780 aacaggacct gaactgatag aaaagttgtt actcctggtg tagtcgcatc gacatcttga   840
tgaactggtg gctgacacaa catacattgg cttgatgtgt acatattatt gtagttgtg    900 tgtgtatttt tatatatata tttgtaatat tgaaatagtc ataatttact aaaggcctac   960
catttgccag gcattttac atttgtcccc tctaatcttt tgatgagatg atcagattgg   1020
attacttggc cttgaagatg atatatctac atctatatct atatctatat ctatatctat   1080
atctatatct atatctatat ctatatatgt atatcagaaa agctgaaata tgttttgtaa   1140
agttataaag atttcagact ttatagaatc tgggatttgc caaatgtaac ccctttctct   1200
acattaaacc catgttggaa caaatacatt tattattcat tcatcaaatg ttgctgagtc   1260
ctggctatga accagacact gtgaaagcct ttgggatatt tgcccatgc ttgggcaagc    1320 ttatatagtt tgcttcataa aactctattt cagttcttca taactaatac ttcatgacta   1380
ttgcttttca ggtattcctt cataacaaat actttggctt tcatatattt gagtaaagtc   1440
ccccttgagg aagagtagaa gaactgcact ttgtaaatac tatcctggaa tccaaacgga   1500
tagacaagga tggtgctacc tctttctgga gagtacgtga gcaaggcctg ttttgttaac   1560
atgttcctta ggagacaaaa cttaggagag acacgcatag cagaaaatgg acaaaaacta   1620
acaaatgaat gggaattgta cttgattagc attgaagacc ttgtttatac tatgataaat   1680
gtttgtattt gctggaagtg ctactgacgg taaaccctt ttgtttaaat gtgtgcccta    1740
gtagcttgca gtatgatcta ttttttaagt actgtactta gcttatttaa aaattttatg   1800
tttaaaattg catagtgctc tttcattgaa gaagttttga gagagagata gaattaaatt   1860
cacttatctt accatctaga gaaacccaat gttaaaactt tgttgtccat tatttctgtc   1920
ttttattcaa cattttttt agagggtggg aggaatacag aggaggtaca atgatacaca   1980
aatgagagca ctctccatgt attgttttgt cctgtttttc agttaacaat atattatgag   2040
catatttcca tttcattaaa tattcttcca caaagttatt tgatggctg tatatcaccc    2100 tactttatga atgtaccata ttaatttatt tcctggtgtg ggttatttga ttttataatc   2160 ttaccttag aataatgaaa cacctgtgaa gctttagaaa atactggtgc ctgggtctca    2220
actccacaga ttctgattta actggtctgg gttacagact aggcattggg aattcaaaaa   2280
gttcccccag tgattctaat gtgtagccaa gatcgggaac ccttgtagac agggatgata   2340
ggaggtgagc cactccttagc atccatcatt tagtattaac atcatcatct tgagttgcta   2400
agtgaatgat gcacctgacc cactttataa agacacatgt gcaaataaaa ttattatagg   2460
```

```
acttggttta ttagggcttg tgctctaagt tttctatgtt aagccataca tcgcatacta    2520
aatactttaa aatgtacctt attgacatac atattaagtg aaaagtgttt ctgagctaaa    2580
caatgacagc ataattatca agcaatgata atttgaaatg aatttattat tctgcaactt    2640
agggacaagt catctctctg aattttttgt actttgagag tatttgttat atttgcaaga    2700
tgaagagtct gaattggtca gacaatgtct tgtgtgcctg gcatatgata ggcatttaat    2760
agttttaaag aattaatgta tttagatgaa ttgcatacca aatctgctgt cttttcttta    2820
tggcttcatt aacttaattt gagagaaatt aattattctg caacttaggg acaagtcatg    2880
tctttgaata ttctgtagtt tgaggagaat atttgttata tttgcaaaat aaaataagtt    2940
tgcaagtttt ttttttctgc cccaaagagc tctgtgtcct tgaacataaa atacaaataa    3000
ccgctatgct gttaattatt ggcaaatgtc ccattttcaa cctaaggaaa taccataaag    3060
taacagatat accaacaaaa ggttactagt taacaggcat tgcctgaaaa gagtataaaa    3120
gaatttcagc atgattttcc atattgtgct tccaccactg ccaataacaa ataactagc    3180 aaccatgaag tgggtggaat caattttttt aattttccta ctaaatttta ctgaatccag    3240
aacactgcat agaaatgaat atggaatagg tgagatattt tgtgtttttc ttgtcttttc    3300
tctatatcaa aattttttaa attataaaat ttgcattaat ttgtcttgat ttattattca    3360
tatttattat tccacatgga gaaaaaatat ttaactgatg gatatattta aatgaaagaa    3420
aaacttgtaa ctttacaaga ggtttacaaa gtttatagcag tgtttaatgg atgaatggtt    3480
tgtatgtttc atgttgaatt aatttttaca cttcaatggt atgcatatta actttgaaaa    3540
attatatata tacacatata tgtacatata tatgaatata aataaaattt tatatgtgaa    3600
gaagccagaa ttatgctcct tcacataact ccctcagact agtaaaatag ataaaatctt    3660 tgttttaat acagaaaaat gggtcattat ttgatggtct gaagaagaaa tattgtgact    3720
gggatatgaa tggcaaaccg tagtacaact atgttcaaaa gaatgcctga aatatatttt    3780
taaccatttg actttcagga cagttacagc actacagtac agggaaaaac caaacaactg    3840
gaagacaaaa tctggatttt agtgataggt ctactataaa ttatgcttgt taacttcatt    3900
ccttagtttc ctagttttct tttcctcaag tataaaatta agatgcttag gttatcccta    3960
atgttctttt aattctgaaa ctgtacagtt ctaactgaaa cacaaacatt catatgtaac    4020
aatgattact ttcttggttg cagttgaaaa cacgtttcat gaagtttatt ttgccttcca    4080
gcttccatat tggattctta ccaatgtact gcagagataa gtttagctga cctgtaagtt    4140
ttgcttatat aaatgtactt taaatgtgta aagcaaggat aagtaaatac ttaaataaaa    4200
ttgggtaccc ctgtgagctc ttaaaagcac aaaagcaatt tggacaattt caagaaaagt    4260
tactcatact gaatatcaac ttgatgttga agaggttaaa ctgttgacta atgtcttcga    4320
cattgacctt ttgattcctt gaaatctcat gagtcaaacc aaatcagatt ttagaaactg    4380
aagattagtg tctgatcagt gacaaccata tactaattca ggaattttc tcatcagtac    4440 caacagggtg atattataat gttttctttt ctgtatacta tttaaatctt agcagcaaac    4500
cataggtgat aaaatattct atttgctgtt atttgtggag agtatgttag tctcttggat    4560
gtctttccat tccacatttt aaaaatttct aacaaagaat ttaaagtagt gtgttgctgt    4620
tactccttgc acatccaaac ctgcataagg attgctttga gtcaatccat gagcactgta    4680
gtcttgggtt ttagacccttg atcatactgg gaatagacac tgttagaggt ctgtctaatt    4740
accaattttt ttttgcttaa atttaaaagt aaccataaag aatatagata ccctcaatta    4800
```

```
tgggtacatt acagtagatg gatggtcaca gaaggagaaa ccactcttat gggaaatcca    4860 cttatttag cctttaacat ctatatgtat atttatggca aaagaaaaca agaaaaagac    4920
taaagtttct tctcagatga cctggaagct aattttacat aatttttcaa atcaaatgtc    4980
taaacagatt acaacataaa tagaaaacaa aacaaacaaa tgaaaaacta tacttgagaa    5040
aaataagctt gctgcaggtc tgttccttaa ggattcacac gtattttgt ttcagggcta    5100 ccatattttt tgcccagttt gttcaagaag ccacttacaa ggaagtaagc aaaatggtga    5160
aagatgcatt gactgcaatt gagaaaccca ctggagatga acagtcttca gggtgtttag    5220
aaaaccaggt gagtgaataa ttttaaaaaa gcattgtgat atttgacaaa aatttagcat    5280
gctgaagaga agatacaaaa atagcagtga aaaatgcatt taaatatttg aagagctatt    5340
gtatgaaaga gggattagat tcattctgaa ttgctaaaga gggcagaaga gaacaatagg    5400
tagttattat aaagagacca tataaatatg atgaactaag gttctgaaat aagattatct    5460
tgatgactat gggcatatta acttttttga gcttcagttt tcttatctgt aaaataaggg    5520
atgataatag ctcccatttc atagttagca tggaaattga taacagca atagtagcta    5580 acttttatta tacacacaat gtgactggca ttattctagg gagcataatg tgtatattga    5640
taataaaaat attttatgac atagggata gatagcactg atgaatcaga atggttgtcc    5700
agtgagtcaa gagatgctgg ctcgggcttc tgggcaggat atcagctttg cttacctata    5760
tttatttatt aaacatttaa ataatcctt gaagatagat gctaatcttc caactgagga    5820
agctgaggct cagagaattt aagtaacttt cttatgggaa ccaccaaatg gcagagccag    5880
gatttgaact agaccatctg gcttaaaatt gacagtctta gtagcttcat tacactataa    5940
ctatagtgaa tgtaagatgc atagcacatc gttagggttg ccaggtttag caaacaacaa    6000
caaaacataa tacccagttc aatctgaatt ttagataaac actaaatact tttcttagta    6060
taaggatatt tcattgtaga agctcaacaa ataatattta ttatttattt tatctcaaca    6120
tagaaacaaa cttgataatg attagaactc tccaattata aaacaacatg cccagagaat    6180
actctgttat ggtggggtta attaggtggc tgaaagacaa tgtacctgga atatcataga    6240
agagatgctc ctttaaggat atagtttaag ttctttccaa ctttgaaatt tatgaattga    6300
caaaaatttc tgttttgcat ctctatttt gtcttgttct gataatcttt tcaaaatgtg    6360
tataaaaaaa caagaataca ttatctattg caactttaca accaattaga ggttcaaggt    6420
aatgttacag atcgctgatt tattcttgta aattcaaagg tatgtctttt aaatgaggat    6480
tgggaattag aaatcttacg taagccttcc aggattctct aaatattact gtagcagcta    6540
taaaagctac ataaaagttc cctcagatac atgaaacaca tgtattcctc agatgctttc    6600
tgtggaatat tgatgctgtc atctgagttt ggtaagggta agtcacagag gaggaaacac    6660
atacatttta aaacattta gctaaatatg taattgtggc caagaaaagt gttttttaa    6720 aaaataatta tttcatttca aaatcatttt tatttataat tgaaataat atgcagtttt    6780 ttattgtctt gtaaggatgg catgtaaaat gagcatttat gtctgaaatg tggtatgtct    6840
gtgtgtgtgt gtgtatatgt atatatgtat gtatatacca taatatatac atatgtattt    6900
gcaattccaa aagttacatc tttaatgaga atcatgaaaa tattattttg ctcagtttct    6960 tttttattt aaatttaaat ttaaagttct ggtgtacacg ggcaggatga gcaggtctgt    7020
tacataggta aacacgtggc atggtggttt gctgcaccta ccaacctgtt gcctgggtat    7080
taagcccagc gtgcattacc tattttcct aatgctctcc ctccctgcac tccactccct    7140
gacaggcccc agtgtgtgct gtttccctcc ctgtgtccat gaaacatggt ttatatattt    7200
```

```
ataaaagttt atatatccta gtccaaattt ttgataacac aaaaaggaaa aataaaataa    7260
ttcaaaattg ggaaagagaa acaaaagatt gcatggcttt tttccttta ttgtttggac     7320 attaaagtct cattttccat aaggcagcaa agaaatctat ttcatcaggc tgaaacaaaa    7380
tacattagaa tttgtatgga aaattttca gaatctatag ttctgatttt agacattaga    7440
aaatgtttca tgtgtcttat agattttaa agcaaagtta gttgtctttc tccaaacata    7500
aaatatttct tatagctacc tgcctttctg gaagaacttt gccatgagaa agaaattttg    7560
gagaagtacg gacattcaga ctgctgcagc caaagtgaag agggaagaca taactgtttt    7620
cttgcacaca aaaagcccac tccagcatcg atcccacttt tccaagttcc agaacctgtc    7680
acaagctgtg aagcatatga agaagacagg gagacattca tgaacaagta aggatccagt    7740
ttaaaggtag atgcaaacct cagaaacaca gcaatggcaa gcctaattta gtatttttgc    7800
aatgtactca tgtactccca gtaagaggta taatgtttct ttggtgttgt gtctgctgag    7860
gtcccaggca aggtaattag gagagcaaca ttcaatgtaa cttggtttcc atagcacgct    7920
agatgtagta caaccacag dacaaaccta ccagaggttc cattagtccc ttgagagata    7980
tacacctttt ttttttcttt ttacccattc tactctcaat tttaccttgt tcaagaatat    8040
attagtattg caccaaattg atgctttcca gagccatata ttggtgtttt gtgttcacct    8100
aattgcctag aaataaaagt tagagatcca agcatggtca agcatggtca agatacacag    8160
acatggcaaa ggtttactga acacttagga tgttgtgggg ccgggcgcgg tggctcacgc    8220
ttgtaatccc agcactttgg gaggccgagg cgggcggatc acgaggtcag gagatcgaga    8280
ccatcctggc taacatggtg aaaccccgtc tctactaaaa atacaaaaaa aattagccgg    8340
gcgtgatggt gggcgcctgt agtcccagct actcgggagg ctgaggcagg agaatggcgt    8400
gaaccctgga ggcggagctt gcagtgagcc gagattgcgc cactgcactc ccgcctgggc    8460
cacagagcga gactccgtct caaaaaaaaa aaaaaaaaaa aaggatgttg tggaaacatg    8520
tctgcttgca cagaggatca gattaacact cacaaacaaa ctttgaagcc tccttctcct    8580
cttcctcttc attcttcttc tttccccat tttgttgata ggaaattgaa ggttggaagg     8640
ctaaaacaac tggctaaggg cacacagcta gtacatttga ccccaggttc ttctgttgga    8700
gaagcctgta cgtaactctt caatcacttc tgccttccat gttacttcct aaaccagata    8760
aatagagaga ttgcccttag aacatctctg ctatggcgac tatccaggtg cataacccca    8820
ttctgcactg acaagggata aaatgtccat cttttctgttg cacttagcag aagtctggct    8880
ttgctgatcc ctgaaacata tctgagtagg cttattgaaa aagacctttt aataagaatc    8940
atggttagca tgtctgccta ttttcttctc ataatagaat ctggtaccat ctgtcagata    9000
tttttccccc caggatcttt agtgaggaaa attttgacaa catgtggaaa aaatatgatg    9060
attttcccct taggaacaca gtaaagacaa agtcaaatgc atttgttgt tgttgttttt     9120 gaatctttaa ataaatccca gtgtccagtt ccaagcagta gtagtcctat ttttaggtgt    9180
ttataaatct tctagctcta tttatttca cagattcatt tatgagatag caagaaggca    9240
tcccttcctg tatgcaccta caattcttct ttgggctgct cgctatgaca aaataattcc    9300
atcttgctgc aaagctgaaa atgcagttga atgcttccaa acaaaggtat catatttgcg    9360
tggatatctg aaccagtact gtagtctatg actcattaaa acaaaacaaa gttaaaaatg    9420
aaaacgtgct taattgtgga gagtatcgtt tttggaatag agaaatagtt cagcagtctg    9480
atattcttcg agtgaacaaa actggatttg ctggtttta ttatctattc attaagtcaa     9540
```

```
caataattttt attattaagg aagtgagttt gatgggataa agaaggaaag acagacagac    9600
agaaagagag aaagagaggg tgctataaat gggaaggagt aagtgaaaga aaacggagaa    9660
aaggaggagc agaggagaga gaaaaaatga agaactatga taaatgcttt atacttactg    9720
ttttttttaaa ccttagaaca aatttgaggt gtaagtattt ttgtccttta acaaactagg    9780
aaagaggttt agagaagaaa attttttta ggtttagaga ggtagaataa tatccaccat    9840
taactacttg ctaccagcag tcctataaca aaaatttcct gagaactgac tactctcagt    9900
gtcaagccgt gatacaatcg tatttttgt aactgagaag acacttaaga aattagcagg    9960
cttcaatttg tctttaagct gtttaaaggt acagttgttc atttatgatc cccagtataa   10020
aagttatgtt tttgtttcaa ggtactttga gtaaatttgt ctggcacaga tgcatataaa   10080
ctaacccaaa agaataaatg agtcaataat attctgcgat aatgtatgac atttataatt   10140
tttagtaaaa aacatatttt atggaatttc attttaccta tacttgttgt ttttctaaat   10200
attagagctt gtaaagaaaa tgttagtata tgctttcatg acattttgtt tcctctacat   10260
ctaggcagca acagttacaa agaattaag agaaagcagc ttgttaaatc aacatgcatg   10320
tgcagtaatg aaaattttg ggacccgaac tttccaagcc atgtaagttc aagttctatc   10380
tagggaagag ggtgagagct acagaactac cattttgcaa tttgggttcg ttttttaat   10440
tgttgctgtt ttagagaatg aagaccccctt tgtgacctct ttgatgaggg ctaatgggat   10500
tagaaccatg aactcttagg atcagaagga agctaacgga taagtcagtt taacacttac   10560
taaagcctag ctgagataat acatagaaaa gacttttaaa gtttatgtta tttacctgtt   10620
ctttaagaca cttaagttct ggcctgccat caaattatac ctcatcacta gaccatatttt   10680
ttctagctct tctacaaaat aagtcagcct tcactgagtg tcatttaaaa cttttgcctt   10740
aacaagaaat tctttatatt aattgtgttt cttaatcttc tataaggctc tttatagcat   10800
ttattgcttc ccataaaaat attcctttga ggcaataata ttagaatcta gtgtcaggag   10860
aaaagaacat tttaaattat ataacttctt taaagtactc atcaactctt ttatgataaa   10920
acatttctag tatatgaaaa tatctgagct gctaatcgaa tagtagtaag tatatatatt   10980
cagagtttat ttgattgctg tttggttaaa taacacgtta aagcatattg tagacaatgg   11040
aaatctagaa tgaagttttt agtaatagaa ttagttctaa agactgaaat ttcttcttgt   11100
aagaagtcag atttatgcct taactaccct ccaactcaat tagaaattga aagattaatt   11160
tatgacctac tttaaaaaaa tttatcttag taataaaata gaattgaga tagtattata   11220
atacccttat catttgctat ccataagtga aagctaagtg gtctaaattt atagagaaga   11280
tccatcttta tcagaagcag gagtaacact attttctcta ggagcaatgg ttttacaaag   11340
acaactctta aaatttaatg aaatatgcag aggaaaccag aattttttatt tcttacttct   11400
tttttggcca cattactctc ttggcacact ggtatgcctg aaatgtttaa tctgctccac   11460
tttcttgtcc catttcattg atttgcacat acgcctcctt tcctggattc tcagaagtat   11520
tttttacccc agtaaaaaat ggttctcatt ttcatggaat tttccatttc ttaattgttt   11580
atccttttaa agttttatgt ccactcaata caaatgctca gcataagggt tgaatggcaa   11640
aaataattta ccttaattct taagacatgt tttaggaaaa gataaattat ttctaaacca   11700
tttgtggggc cagctcacag tttacagagt taccaccttg aaagatatgg ctggaatcaa   11760
gccttaaaac atgtttcctt ttctttttaa acaacaaggg aatttcagtc atttctcttt   11820
gaaacttcta ctgtagtaat actctataaa ttctatttta ttttgacaga taaccaagaa   11880
attaatttct aatttctttt ttttccctag aactgttact aaactgagtc agaagtttac   11940
```

```
caaagttaat tttactgaaa tccagaaact agtcctggat gtggcccatg tacatgagca   12000
ctgttgcaga ggagatgtgc tggattgtct gcaggatggg gtgaggagtc ttgcttctta   12060
aaatagaaga ttttcactcc cttttctttc tttttgtctc attctaaaag ggagaaggtt   12120
gtttgacttg aattggttac agagtatgta aactaggtga ctccttaaat ttgcagaatt   12180
ctcggtagta aaacttaaac catcttttgt tgatcctggc tttcacttta gctatacccc   12240
tttttgtgaa accaaggctc atctatttct tacttctaaa aaaaccgtgg gaacttctca   12300
gaaggcttct ccatagttac ttggaggacg ggaggaaact aaggtttaat gtatttattt   12360
tttcattcat ttattctttc atttgacaaa taaatatata ttaaatactt tctatctgct   12420
agccactatg acagacactt gttttaaaag cacaggctga cctcaaggaa ttcacagtct   12480
gataggagag ataagacagt gacctccttg gagttaggga ctgccttggt ttactgttat   12540
ctccatagca caatgcctgg cacatggaag gcattctata atagtttgtt aaatgaacga   12600
atgcaataaa aattgcacaa gtaactgtcc taccaggtaa aaagctagcc ttgccaaaga   12660
caagtgtgaa taaagtggtc tcggagaatt agaaaacaaa atttaaaaaa cccagcaaca   12720
gtttcttgag tgtgctctag tcagtggtgg tttaagcagt gtggcattgg cttatttttgg  12780 ctaaccctag acttcctaga ttttacaaga gaggactgtt gaccctcaga ttactctgtc   12840
tctgtgggct ccatgacaca ccaaagagat taaaatccaa ggagcttaaa aattactgct   12900
cttaggtact caaatggctt gataaccagc actggactat ggtttccaga aggctgaaag   12960
tgaagataaa atgctcattt cagcccatcc gatggcaatt cagtgagatg cttgaagtaa   13020
gcaagaagcc gaggctgcag aggaggcctg agagtgacag tccctgagga gctggggaag   13080 aagtggggagg aggcagcctg gcaggcgact gtactacttt acttgttttt cttctagaaa   13140
tatggcatac taggaaaacc aacaagaagt attttgtttt tctttgagct cagttttccc   13200
attttgaacg gacaatttta ctgtttctcg ttgtcattt taaaaagtta attttttcaa    13260
tttttggagc tcataaccac ccttttcctt taaagtggaa acattaattt cagcatgata   13320
tgtaagttgg attttgatag ctgaataatg ggttctaatt atctttgctg agaatgtaca   13380
gaattttcag tcccatgaca ggtatatatg taagctctgc ctctctctgg ccacttaggt   13440
gcattgccat tttattatct atagactgcc ctctgaaggt catagtcagt cactgcagta   13500
tgttctgata aagatgatta tcattcttac ggaatttctc gtggagcaga aagtttgctc   13560
tccatgttat gataccagtt gcaagtgttg tttaggggca aatttgaatg ctaatagaaa   13620
tacatatagc aacatgcatc ctattttatt tgagcacatt tccctcttat ttgtaaaggt   13680
tttcaattga aataacatag gatttagctt acaactatgg aaagaagaat tgaacaaaca   13740
ggtaagtgga aaggaatgag aaaaggcaaa agtgggggaga aagcactaaa acgggagaca  13800
agttaaaatt tctttttaat tgataggtca cgttctcact ctatttgcct ttaagggaag   13860
aaagcaatca agttaatatg ttttccttca ttgtatagta tgtaactacg gacactatta   13920
gaggagggat ttgtgtagca cttaggacat tatacttgat aatttccaag ggtctttcta   13980
gatttaaaag tctgattcta acgtagtaat aaaaataaag gcccaatttt ctctttaata   14040
ttgcctgaag atattactct attattgcat taaaattaaa cattcacaca ttgtttgcac   14100
tgctaaataa aattatgtaa tttcttcttc tttccttcct ccttccccca tccctctcta   14160
tttccctttc cccttccttc tttcctggcc ttttttcctt cttttctttgt tcccttctcc   14220 ctccctcccc tttcttcctt tttctaaagc tggctttgag atcctttatt aaagaataaa   14280
```

```
tctttaaaac ttatacttta ttttccctgt tgcaggaaaa aatcatgtcc tacatatgtt    14340
ctcaacaaga cactctgtca aacaaaataa cagaatgctg caaactgacc acgctggaac    14400
gtggtcaatg tataattcat gcagaaaatg atgaaaaacc tgaaggtcta tctccaaatc    14460
taaacaggtt tttaggagat agagatttta accaattttc ttcaggggaa aaaaatatct    14520
tcttggcaag gtaacacact ctgtaaatgc atgttcatgc aagtaaaaat gattatgtgg    14580
ctgacagatt tgcgttgttg aaatggagag tgatgattat ggttttgag ttcaatatgt    14640 gaggatattt ggctagaatg ttctgagcca aaatagattt cagtagataa ccagggaata    14700
agtaatggga tttggtgttt aacggtgaag cgttcaccac tgtgactcat taactgcttt    14760
gctatgaagc tgaatttat ttcacatcaa tttctctgga atcagaagca ttgtcatcct    14820
gtaaagatta ctcatatcaa ggccaccatt gaactctcaa ataggatatg gatatttttg    14880
taataagaag agttcatgat taagaatgaa ctcttgctac gcatgttaaa aaaaaaactt    14940
ttctccaaaa gataacacaa gagataatgc taggtagaag aactttttata ggaacagctt    15000 attggctatg tattaaatac atgttttgta tttttttaaga aaatcaaaac atgtttagag    15060
acatttgcag tacagtagtt tgttttaata caactgatag gtcacgttct cactctattt    15120
gcctttaagg gaagaaagca atcaagttaa tacgttttcc ttcattgtat agtatgtaac    15180
tatggacact attagaggag ggatttgtgt agcacttagg acattatact tgataatttc    15240
caagggtctt tctagatta aaagtctgat tctaacgtag taataaaaat aaaggcccaa    15300
ttttctcttt aatattgcct gaagatatta ctctattatt gcattaaaat taaacattca    15360
cacattgttt gcactgctaa ataaaattat gtaagctaga ataaagttca gatttaggag    15420
acacatagtg acaactgatt ggtgacagaa ctaatcctat aatctgggaa tacggttagt    15480
aaagtcaaga attacctta agtttacaca tccatgcaca tctaaatcta attgtttaat    15540
agaagcagtt cttcagttgc aaaggttctt tgcagtagaa ttttctcagc caggaatgat    15600
tttcccccag atatttgcat ggcttctttc acttagctga tctctgttct gatatcagct    15660
gcctagagag aattttcttg accacattca aagttagtgg cctctccacc ttgggtatca    15720
tccttttttc tcttttcat ctttatttat tttcattgat ttatcgctaa ctgaaatgag    15780
atggcctatt tcttgtttat tgttctgcc tccctataat gtgtgctttt cagagggcag    15840
gtatttatct tagacatcat tgagtccgtt ctgcttaaag caatgctagc aaagagtgga    15900
cactggaaaa atatttgttg aataaatgaa tataaagtcc gtaattgaaa agtcaaattg    15960
agagatgcag gagaaaacaa aaagccattt tacaggacaa tttgaaggat cacagtctgt    16020
attaacagtt ttgccattca tataattcaa atcatatttg attttcaggt ttatttattt    16080
gaatttaact tccacatgcc atattatata ggaataactg gagaagtgat ggctcctttt    16140
gtctcttagt tccaataact tgaaatattt ttctccacat atttcagttt tgttcatgaa    16200
tattcaagaa gacatcctca gcttgctgtc tcagtaattc taagagttgc taaaggatac    16260
caggagttat tggagaagtg tttccagact gaaacccctc ttgaatgcca agataaagga    16320
gtaagttgct ctagaatttt aggggagtat gaaaaactgg attgatatca tctgttaaaa    16380
atgctgtttg tttgaaagcc tctagttttc aactagttgt tagccagtta tatctatttg    16440
tctagatatt aagctgttat taactagcag tcagcagcta gtggcttgct ttagaaacaa    16500
aaatgttaat tgcttctcag ccttttggct aagatcaagt gtagaaataa aaatgttaac    16560
caaaagtcct tgatccaca aataaaggta gtattcatta ttcattttg gataacttca    16620 gaaaggcaag aatttggtac agaaagaact gtaaccattt atccaaagat tgagttttgc    16680
```

```
cattaaatga tttttgtgatt tataaaatgt taaacttaat ctccccaaaa tccatttct   16740 gtaattatca aaatttacac tttaccatat ttaatattta aacatctctg attggtttta   16800
taatagtata taatattgat caatttata tacaaagtta tgcatccaag aaagaaaaa    16860 tgtatatgta ataattcttc attttcagga agaagaatta cagaaataca tccaggagag   16920
ccaagcattg gcaaagcgaa gctgcggcct cttccagaaa ctaggagaat attacttaca   16980
aaatgcgtat gttttttgtaa acagtatttt tagtgaatta aaattattaa agagaatgta   17040
gccttcccca attctcctcc tttggaagca acaagaatga cctgtgaggt ctgatctgtg   17100
gtattgactt taagttcccc atactgtgca aatttttgca gtaaagatat ccattctgtc   17160
atagtctgtc cgagttaaag caccaaaaga tcacagttaa aatcaatgaa gctccgaggt   17220
tgagaataca agtcaggctt cctcctggag tttgctttt cattgtgata tgcttctata   17280
ataggagtac agggagtggt tgttagagta aatgcatctc aaaagttggt tcaaatacca   17340
tgtagatgaa acaaacgagc tgacctcatg tcttctggca tgagagtaga gagtctgtga   17400
gaagaagcaa ggcggctaaa aactcatgaa tgactcagca ggacttagtt aaaaatgct   17460 tctttcaggt ttctcgttgc ttacacaaag aaagccccc agctgacctc gtcggagctg    17520
atggccatca ccagaaaaat ggcagccaca gcagccactt gttgccaact cagtgaggac   17580
aaactattgg cctgtggcga gggagcggtg agtgtctgct tggtttggtc ccatctcatt   17640
tctgccctgt ttgacttgaa atagcctcat aattccctc tagggaagac ggtaaaaacc    17700
aatgtagaga tggccttagg aggcttgttt gattagtcac ggttggaggg gtgtgagaac   17760
ccagctctgg atggctggca tgtggccatg cttcctattc ctccagggtg gctggtggaa   17820
gttcagccag tttagtcaac aatatctgag ccaactttat atatcagaaa gacagaacga   17880
ccaacatgta actcataatt cataacaatt cataattcat aacttcaaat cataatttct   17940 gcttttttgtt catatactta ctttgatgtt ttaaaaaagc tttatctttg attgattaaa   18000
attagtcatg ctattttagc catatttata ttttcacctt ttgtaacatg atattattat   18060
tatgacatca ggaataattg gttcccttc gcagggtata gggtacagca caggataagt   18120
attatgttct gaatagtaaa atgactttcg agtcagtaat gccaatattc tttacttcct   18180
aatgtcacta gtatcataca taagattaca ggatgaatta aaatatttt tcctataaag   18240 tcataattgc aaacaaaatt gtctattta tccttttcc tcttttcat aatggggagt     18300 tatttgctgt tagtcttcat gtcatacatt tttcccccaa aggttaagag taaaaggaga   18360
gttcttgtga ttaaatgtca cctcaattgt ttgttgaatt tcccatgctg ggaggctgca   18420
gggatgcagg atggtgtaat ggttcaggag tgtatgttcc ggaggccacc agccaacaac   18480
cgcattctac tttcactatt ctttagttgt atcacagtgg gaaagcaact tatgtcatta   18540
agcttgagtt ttttcatctg acatttgaga atacaaatta taccaccctc atacgacagc   18600
tgttttaaac aagataatct gcataactca cacagcacta gtctgacaga taaagtgcac   18660
acaaaacata ttatttctta ttacaagtta ttactaggtg attaagaaat atctcctaag   18720
taggcaaggt agcaagattc tacattagga aagtcttaaa aacccacaaa attgctctta   18780
cttcttttca attaggatga tatattagct gcaagtgtat acatgtgtat atgtatgtga   18840
ataaaagggg taagtttgtg ctattcttac cttcagatag tgattatcaa aagaaaaatg   18900
gaaagttcaa ctaaatacac atgggaaaca taaaggcaga gacattttg tcctttagaa    18960 gtgtgtatgt aactggaagc atgttcaaa tagctgacac aaatagctaa atgactatcc   19020
```

-continued

```
tcaacatcac atatggacca tctgctacta cttgctaagg cttagcccaa acaaatgggt    19080
aaatcctgga atttacaata taatgtcaca tgatcctaca tagcaaattt tcctgtaata    19140
ttaattataa attgctgggc attagaaatt attgcagcag ttttctgaaa aactgaacca    19200
actttgtgac taatgcccaa tctccttact ttttttttctc attctcctaa ccaggctgac   19260
attattatcg gacacttatg tatcagacat gaaatgactc cagtaaaccc tggtgttggc    19320
cagtgctgca cttcttcata tgccaacagg aggccatgct tcagcagctt ggtggtggat    19380
gaaacatatg tccctcctgc attctctgat gacaagttca ttttccataa ggatctgtgc    19440
caagctcagg gtgtagcgct gcaaacgatg aagcaagagt aagaaactgt tacttgctag    19500
catggaaaag aatgacaacc ccaaagagta actgagactt ctacctcgct cacctaacac    19560
tattgggctc actaacagag cgttactccc aaaacactta aaatgccttt gaaaatagtt    19620
ttgtctcagt gtcttcacag tctcattggg gaagcaggtc tagaaaaatc gacgagggtg    19680
gacaatttcc tgtttgtaaa aataatctct gttgtaactg ttattgtgat atgtatttgg    19740
gggttgagga aaagtgggca atctattctg aggaattaga gtgtatcttt gcagcaaatt    19800
tgggtacttc cattccaagc acaggaaaca catcattgaa tctttttta cactatttac    19860 actttgaaga gaataaccat cttatttaat tcaaccatgc agtttgggtg ttaagaaatg    19920
acatgtacat ttcagttcat tgtgggagct cttttgtaat ggtgatggtc atgcaagtca    19980
atggagctta tgttcttcaa actcccatgc attttaatcc tcacttgttt tgtaaatagt    20040
cttccttcat tggaaaaccc attcttctct tttttcctct atcacagtct gaggtatgtt    20100
tcacagtatg ataagaatgt tgcctgttct ggcaagcttt ttctattgct ctggtctact    20160
ttctattgct ctggtctaag tccaacatga aaggcttgct aagtgagcag tgcaggcaat    20220
tagtgctgcc agtgcccaga taaggggtgt gataactgga tgggcaggat tcggagatct    20280
gggtctttga gtgtagataa gacacagtta agaagagcgg acaggaaagg atattcctgg    20340
gggatgaggg gagattgcct tccactacac ataagtatgg tcaagtatga aatagtgttt    20400
tatccacaac ctgcacaact ccaggctggt ggaaacttg gcatgttttc agcctcaatc     20460
tttctactga aagtactaga caaggtgtgt gtggtcagtc tggtgatagg ttgatggagt    20520
aagggtttag gctctgaaaa ttctctacta ggaaggctgt agaaaaatag cattgcataa    20580
cagacttctc ttgtattttg ttttgtttta aatcacaggt ttctcattaa ccttgtgaag    20640
caaaagccac aaataacaga ggaacaactt gaggctgtca ttgcagattt ctcaggcctg    20700
ttggagaaat gctgccaagg ccaggaacag gaagtctgct ttgctgaaga ggtacatgca    20760
gctcatttca tactcaaaat acttgctatg gaattttctg tagtggataa tgaaaggaag    20820
accctacaaa tttataactt taaaatattt tcagagagat ttaaatttca ttgagaagca    20880
gattgaggga ttctataaga tttaaaaaat aatcacattt tcttgcttaa tattaggaaa    20940
atttataata ttaaaatata ttaatagaat tagtaatttt aatttatttc ctagtagaga    21000
aacccataaa gtgaatgtgt aaataattga tggtaattta gatagtttct ggcctaaaat    21060
tgatcaattc agctaaatgg attaaaggat ttaatagcaa attaattgtg caaacagagt    21120
attaggagtc tatttgtaga aaatgttttt gaactcattt agaagcttgc ttttgtacat    21180
caacagagta gtatttagga gttatttta ttacatagta attttagctg gataattagc     21240 cagatttttct ttaaccaggg gattctacct aacatttaaa aaaattaccct tttttcagct   21300 ttattgaggc atgattgaca aatacaaatt atatatgttt agggtgaaca tgtgatgttt    21360
caatatattt atacattgtg aaatgattat cacaatcaag ataattggct aaattttaca    21420
```

```
aatctttagt tgtattgct acatatattt gaatatagca acactatact ttaaaaagat   21480
attctataac ttagcgtttt tgtcaatttt acctttctca ccatgtaaaa tccaaagaca   21540
gatatattta gaaatgtaga gtttttctat aaataatata attagatgca tttgagtgtg   21600
tgcacttacc agtatatgtg tgtgttttg gtgggatcag gtagggtggg acatagataa    21660
ccaaattaga taaaactggt gaaacagatt tgatgtgaag catttctgaa aaacatgaca   21720
caagaagatt aatgttctct aatctgagaa gacatttatt tagatataga gaacatgaac   21780
aaatagtagc agtgctttat ctgcaaacct tttaatttct aataacttgt aatttgtaga   21840
ggaaggggaa agattgagaa tacgcattga tttggagatt gttatagaag aaaactgttg   21900
atgtgaaaga atattgtttt ctccctggct tttactatcc caggttgttg gcatcagaga   21960
tgtgtttctt catttttaac ttagttaatc tacaaaccta tgaattcacc ccggattgta   22020
gagtgttaac tgtatgattg gtataataat ccatttcttt atctgattat gtttattctt   22080
aattttcagg gacaaaaact gatttcaaaa actcgtgctg ctttgggagt ttaaattact   22140
tcaggtaaca aaacattcag acaagcctga atacaatgtt gtttctccag aaatatcaat   22200
ccataatgag atagatcatg aggagtgcca ttaattctct taaaaataca tggaattcaa   22260
aaaaagtttt attttaaaaa cacttgaaca aaattacgca cacaatgtta aattagtggc   22320
tcaactatgc aaaatccttt ttggttattt aaaagacttc aacaaatgct atcagaagac   22380
tttcctacgt atccaatatt tctctgatat aaaataatag aaccagttac ttactgcacc   22440
tattagttta attagtattt aatatatttt tgctcatatt gcaggggaag agaagacaaa   22500
acgagtcttt cattcggtgt gaacttttct ctttaatttt aactgattta acacttttg    22560
tgaattaatg aaatgataaa gacttttatg tgagatttcc ttatcacaga aataaaatat   22620
ctccaaatgt ttcctttttcc aagtttgctt atttatgaaa agttatcgat aatttctttta 22680
gttttgtata ccattgtctg aagcagattc tgttaaaata gcattaagtg ttggttgtta   22740
taggagatta aagctatcca aggatggatt tacagcacta gatcacttgg tgaactgaaa   22800
aatgttccca agtaaacac tatttgatgc taccagggca ttttgtttat taaatgacca    22860
tcactgaagt attctaacag ataatctgga gatgagaaaa gaaattatta ttcttctatg   22920
ggatctaaga aaatttaaca tctactttt ttctcaatct tgttcagttc tctattcaca    22980
gacatttta aacataagaa tattacagtt ttgattgaat ataattaatg ttttcatcaa    23040
ttaaattttt attccacaaa tgtttattaa gccttcactg agttccaggc cttgggctgg   23100
gtacagtcac tgttctccag tcgcttcagt agagaaggaa gcaacacaat aatgatgcct   23160
cagattatga ccacaaggag ttgacaacaa attgttgagg gaacgaaagg gtgggtgaca   23220
tcagttctga ctggaaaagg tgccataaat gtttaagaag agtcttagaa aatgaatgag   23280
cattcatcag ttcaagtaaa agagaaggcc attttatgaa agaggaaaca tggtcagagg   23340
tactgggtat gacaaagtat gatgaatagt tttagaggag tacagggtag gtaggaaggg   23400
tagagatgta gaatgttagg caggatgtgg aagctatgaa gggctaatcc agactctcag   23460
ggctctattc taagagggtt ggacaatatc ttatgagtaa cagaggacca cagtgatagc   23520
taagcagagg tgtgctatta ataattagct ttgaggaaga taatctatga gatacgagc    23580
atgggcaatg gggcagggaa aagggtagag ggggcaaagt cagcaagagg tgacaaaaag   23640
accattcccc cagtagggaa gctgtttatc ttattagctt tgaatagaaa tctgaaaatt   23700
acatgcatac tttggcctgg gctctgggag aagacaatgg ctttagagca ataaaatgtg   23760
```

```
ctttcggttc ttcttctctt tttttttgaa ttggaatctg ctatgttgcc cagctggtct    23820
caaaatcctg ggctcaaaag atcctcctac cttggcctcc tgagtagctg ggactagagc    23880
catgaaccac tacacctagc ccttttagtt ctaactagat tgctttctac ttgacatttt    23940
tctttccatt gtactgcaac atctatgaac tttgtctgat tttggtgtaa ttctaaaagg    24000
tattaattta aagatcacaa taaaataaaa tcacgttcaa tataaaagca ttaagctgga    24060
aaatgcttta ttttttaag ggaaaagcac aatgaaggta aaactgttag ggaaatttgt     24120
gagtcaaata atattttgtt gaaatatata aagaaaaaat gattggaggc agaaggataa    24180
attgacgtaa gtacaattgt aaattgggga ttttaaaaa tttattttat ttatttattt     24240 attttttga dacagagtct cgctgtgtcg tcaggctgga gtgcagtggt acaatctcgg     24300
ctcactgcaa gctctgactc cctggttcaa gcgattctcc tacctcagcc tcctgagtag    24360
ctgggattac aggcacgcgc catgacaccc agctaatttt tgtattttta gtagagacgg    24420
ggtttcacca tgttggccag gctgacctcg aactcctggc tcatgatct gcctgtctcg     24480 gcctcccaaa gtgttgggat tataggcatg agccactgca cccagccaaa ttggagattt    24540
taaaacatct ctacctcatt aacagaacaa gttaggcaaa taacaaataa agactcaggg    24600
tattaaactg ctgtagtcag gattaccaac aactttcaca ctgcaaaatc caatagtgga    24660
ttcttagtct ttagcttatc tgagttctct cagcagcatt tgacacaatt gatcactctc    24720
ttttccttga aacgttttcc tcacttggtg ttcggacttt cttccaacct cattggctgt    24780
ttcacctcaa tcttctttgc tgtgtcctcc taactctttg acctctaaat gttggagtgt    24840
cccagaacag ttcttccttg accgaaattc actcatccag actcagtgca ttaaatgcca    24900
tctagatgtt gacaacacat gtttatagct ccagcctgga tttcttcctt gacttacagg    24960
ctcttacgtc agcttcctcc ttaacatctc catgctgata atgtatagac aacacaaact    25020
tagcacatta caaattgaat gtgaatctac tccttgtccc aaatttgtac ctccatcttg    25080
tctatctgtc tgtttttatg agtcagacat tttggattta ttgatgaccc ctctcttgca    25140
tatcacccac acattcaatc tatgagcaaa gcttgtcggc tctacctta aaaagtatcc     25200 agaatttgac tatttctcaa tactttggta ccagtcacaa tcatatgcct cactggggtt    25260
attgcaatag attcctaatt ggtcttttta caagtgacct tgctccaccc tcaaccctat    25320
tctcaaaagt gaacattatg tcacttttcc actcagaatc ctctagtggc ttcccacttc    25380
tctcagagta aaatgcaaag tctgtccaat gaccctacat gataatatct ttctgacctt    25440
ttttgttact cctctgatca ggtacagagg tctccctgct gctcttcaag ttaccaatca    25500
atgtcctgct cagggttttg ccctcatgac ccttctggct tagaagaccc tcagctatgt    25560
gtgaggctca cttcatcacc aacttcaagc ttctactcgt agttatctgc taaatgatga    25620
tgttttcctc aactacctta ttttaattca gaaatgccat tcccagtccc cacaacactt    25680
atcaccatct gacaaacact agattttact tgtttatttt ctgtctacct cactagagtg    25740
taagctccat gagaacagta acttttgtct cctttgttta cttcggctat cttcagcata    25800
tagaacagtg cctgaaacat aataggcatt ctagaaatat ttatttgagt atgtggagga    25860
atactacacg ccatgggcta tatatatttt cttataaggt ggtgaaacta gagggggttgt   25920 tagcttcctc taataaaatt ttttctaga gaaaaaaaaa aagcacaggc ctaagaaatt     25980
aacataaaaa ccataagata ccactgagga tgttaaagac gtgtgtgtgt gtgtgtgtgt    26040
gtgtgtgtgt atgcatgtgt gtgtgtgtgt gtatgcatgt gtatgtgtgt gtaggcatgt    26100
gtgtgtgtgt atcgtgtaga atgagaatta ggaagtggtg gcattctaga atagctggct    26160
```

-continued

```
tgaaagaggg tgggtaggtt tgggggatag attttaaact tgtgcttttg tctatacact    26220
aaattacaac gaagtctgcc acttgcttca ctgccactgt gaagcataaa tcagaaggag    26280
tagctcaaat tgcttggtga ccacaggata atattgggat aaggctaaac tccagctggg    26340
gcaaaagact ggtgaaaaca gctgggtgca gaacagctac tgttaaaaat taagtcttcc    26400
aatctcttta ttttatttta ttttatttat ttatttattt atttatttat ttttttgtat    26460
tatactttaa gttttagggt acctgtgccc agcaatccca ttactgggta tatacccaaa    26520
ggattataaa tcatgctgct ataaagacac atgcacatgt atgtttattg cggcactatt    26580
cacaatagca aagacttgga accaacccaa atgtccaaca atgatagact ggattaagaa    26640
aatgtggcac atatacacca tggaatacta ggcagccata aaaaaggatg agttcatgtc    26700
ctttgtaggt acatggatga agttggaaac catcattgca atctctttca tgcctacttt    26760
cccaggactt gtggattacc gtataaggaa tttgtctcct ccaatgatgc tgctttcaaa    26820
gagttaagga agggtccaga gaattgctcc atagcatgga attaaattaa taatcaataa    26880
cagtaagatc tctagaaagt ccccaaacat ccattaacta agtaacatgc ttgtaaacat    26940
tcatgaatca aaaagaaat cagaagcata tttaaaaaat attttttgcct gaatgaaaat    27000 gaaaatgtg tcagaattta tagaatgtca ctaaaacagt gacatttaaa ttaaaggaaa     27060
tttataacgc taaaggccta tgtgttatag aaaagaagga agatctcaaa tcaatgacat    27120
cagcttcttc cttaataatc tagagatgaa agagcaaatt aaaaaactag tcatgagaaa    27180
gaagataata aagatcaaag gagaatcaat aaaatagaaa acagaagaaa tcaatagata    27240
taatcactgc aaccaaatgc ggttcttaa gatcaatact attaataaac ctctaaccag     27300
atttctcact accaatgttt ggaatgagag aggtgatagt attacaagta ttaaaataat    27360
gagaagaaaa tgttgtgaaa aaaatatgtc agtaaattca atgacatatg aaaaggacag    27420
attccttgaa agacacactt acaaaagctc atgcaagaac aagtagttaa cgtggttatt    27480
tatgtattaa ggaaattgaa gttgtaatta agatcattcc cacaaagaaa actccaggct    27540
tcacgatgaa ttc                                                       27553
```

```
<210> SEQ ID NO 10
<211> LENGTH: 187
<212> TYPE: PRT
<213> ORGANISM: Homo sapiens
<220> FEATURE:
<221> NAME/KEY: misc_feature
<223> OTHER INFORMATION: Human B interferon
<300> PUBLICATION INFORMATION:
<308> DATABASE ACCESSION NUMBER: Genbank/EMBL/DDBJ Accession No.
      AAC41702
<309> DATABASE ENTRY DATE: 1995-01-01
<313> RELEVANT RESIDUES: (1)..(187)

<400> SEQUENCE: 10

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
        35                  40                  45

Leu Glu Tyr Cys Leu Lys Asp Arg Arg Asn Phe Asp Ile Pro Glu Glu
    50                  55                  60

Ile Lys Gln Leu Gln Gln Phe Gln Lys Glu Asp Ala Ala Val Thr Ile
65                  70                  75                  80
```

```
Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
    130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

<210> SEQ ID NO 11
<211> LENGTH: 212
<212> TYPE: PRT
<213> ORGANISM: Homo sapiens
<220> FEATURE:
<221> NAME/KEY: misc_feature
<223> OTHER INFORMATION: Human a Interferon Variant 2A
<300> PUBLICATION INFORMATION:
<308> DATABASE ACCESSION NUMBER: Genbank/EMBL/DDBJ Accession No.
      CAA00839
<309> DATABASE ENTRY DATE: 1993-12-03
<313> RELEVANT RESIDUES: (1)..(212)

<400> SEQUENCE: 11

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

-continued

```
<210> SEQ ID NO 12
<211> LENGTH: 166
<212> TYPE: PRT
<213> ORGANISM: Homo sapiens
<220> FEATURE:
<221> NAME/KEY: misc_feature
<223> OTHER INFORMATION: Human a Interferon Variant 2b
<300> PUBLICATION INFORMATION:
<308> DATABASE ACCESSION NUMBER: Genbank/EMBL/DDBJ Accession No.
      AAP20099
<309> DATABASE ENTRY DATE: 2003-04-30
<313> RELEVANT RESIDUES: (1)..(166)

<400> SEQUENCE: 12

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
                20                  25                  30

Asp Arg His Asp Phe Gly Phe Pro Gln Glu Glu Phe Gly Asn Gln Phe
            35                  40                  45

Gln Lys Ala Glu Thr Ile Pro Val Leu His Glu Met Ile Gln Gln Ile
        50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 13
<211> LENGTH: 208
<212> TYPE: PRT
<213> ORGANISM: Homo sapiens
<220> FEATURE:
<221> NAME/KEY: misc_feature
<223> OTHER INFORMATION: Human t Interferon
<300> PUBLICATION INFORMATION:
<308> DATABASE ACCESSION NUMBER: Protein Sequence Record Genbank
      Accession No. NP-795372
<309> DATABASE ENTRY DATE: 2004-07-02
<313> RELEVANT RESIDUES: (1)..(208)

<400> SEQUENCE: 13

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
                20                  25                  30

Gln Val Asn Gln Glu Ser Leu Lys Leu Leu Asn Lys Leu Gln Thr Leu
            35                  40                  45

Ser Ile Gln Gln Cys Leu Pro His Arg Lys Asn Phe Leu Leu Pro Gln
        50                  55                  60

Lys Ser Leu Ser Pro Gln Gln Tyr Gln Lys Gly His Thr Leu Ala Ile
```

```
                65                  70                  75                  80
Leu His Glu Met Leu Gln Gln Ile Phe Ser Leu Phe Arg Ala Asn Ile
                        85                  90                  95

Ser Leu Asp Gly Trp Glu Glu Asn His Thr Glu Lys Phe Leu Ile Gln
                100                 105                 110

Leu His Gln Gln Leu Glu Tyr Leu Glu Ala Leu Met Gly Leu Glu Ala
                115                 120                 125

Glu Lys Leu Ser Gly Thr Leu Gly Ser Asp Asn Leu Arg Leu Gln Val
            130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
                180                 185                 190

Leu Asn Asp Met Lys Gln Glu Leu Thr Thr Glu Phe Arg Ser Pro Arg
                195                 200                 205

<210> SEQ ID NO 14
<211> LENGTH: 189
<212> TYPE: PRT
<213> ORGANISM: Homo sapiens
<220> FEATURE:
<221> NAME/KEY: misc_feature
<223> OTHER INFORMATION: Human a-interferon variant 16
<300> PUBLICATION INFORMATION:
<308> DATABASE ACCESSION NUMBER: Protein Sequence Record Genbank
      Accession No. NP_002164
<309> DATABASE ENTRY DATE: 1993-06-11
<313> RELEVANT RESIDUES: (1)..(189)

<400> SEQUENCE: 14

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
                20                  25                  30

Gly Asn Arg Arg Ala Leu Ile Leu Leu Ala Gln Met Gly Arg Ile Ser
            35                  40                  45

His Phe Ser Cys Leu Lys Asp Arg Tyr Asp Phe Gly Phe Pro Gln Glu
        50                  55                  60

Val Phe Asp Gly Asn Gln Phe Gln Lys Ala Gln Ala Ile Ser Ala Phe
65                  70                  75                  80

His Glu Met Ile Gln Gln Thr Phe Asn Leu Phe Ser Thr Lys Asp Ser
                85                  90                  95

Ser Ala Ala Trp Asp Glu Thr Leu Leu Asp Lys Phe Tyr Ile Glu Leu
                100                 105                 110

Phe Gln Gln Leu Asn Asp Leu Glu Ala Cys Val Thr Gln Glu Val Gly
            115                 120                 125

Val Glu Glu Ile Ala Leu Met Asn Glu Asp Ser Ile Leu Ala Val Arg
        130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
                180                 185
```

```
<210> SEQ ID NO 15
<211> LENGTH: 166
<212> TYPE: PRT
<213> ORGANISM: Homo sapiens
<220> FEATURE:
<221> NAME/KEY: misc_feature
<223> OTHER INFORMATION: Human y-interferon
<300> PUBLICATION INFORMATION:
<308> DATABASE ACCESSION NUMBER: Protein Sequence Record Genbank
      Accession No. NP_000610
<309> DATABASE ENTRY DATE: 1994-11-15
<313> RELEVANT RESIDUES: (1)..(166)

<400> SEQUENCE: 15

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165

<210> SEQ ID NO 16
<211> LENGTH: 175
<212> TYPE: PRT
<213> ORGANISM: Homo sapiens
<220> FEATURE:
<221> NAME/KEY: misc_feature
<223> OTHER INFORMATION: Light Chain Human Ferritin
<300> PUBLICATION INFORMATION:
<308> DATABASE ACCESSION NUMBER: Genbank/EMBL/DDBJ Accession No.
      AAH18990
<309> DATABASE ENTRY DATE: 2001-12-07
<313> RELEVANT RESIDUES: (1)..(175)

<400> SEQUENCE: 16

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80
```

```
Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145             150                 155                 160

Gly Leu Gly Glu Tyr Leu Phe Glu Arg Leu Thr Leu Lys His Asp
                165                 170                 175

<210> SEQ ID NO 17
<211> LENGTH: 183
<212> TYPE: PRT
<213> ORGANISM: Homo sapiens
<220> FEATURE:
<221> NAME/KEY: misc_feature
<223> OTHER INFORMATION: Heavy Chain Human Ferritin
<300> PUBLICATION INFORMATION:
<308> DATABASE ACCESSION NUMBER: Genbank/EMBL/DDBJ Accession No.
      AAH16857
<309> DATABASE ENTRY DATE: 2001-11-05
<313> RELEVANT RESIDUES: (1)..(183)

<400> SEQUENCE: 17

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 18
<211> LENGTH: 359
<212> TYPE: PRT
<213> ORGANISM: Homo sapiens
<220> FEATURE:
<221> NAME/KEY: misc_feature
<223> OTHER INFORMATION: Human Decorin
<300> PUBLICATION INFORMATION:
```

<308> DATABASE ACCESSION NUMBER: Genbank/EMBL DDBJ Accession No. AAH05322
<309> DATABASE ENTRY DATE: 2001-03-27
<313> RELEVANT RESIDUES: (1)..(359)

<400> SEQUENCE: 18

```
Met Lys Ala Thr Ile Ile Leu Leu Leu Leu Ala Gln Val Ser Trp Ala
1               5                   10                  15
Gly Pro Phe Gln Gln Arg Gly Leu Phe Asp Phe Met Leu Glu Asp Glu
            20                  25                  30
Ala Ser Gly Ile Gly Pro Glu Val Pro Asp Asp Arg Asp Phe Glu Pro
        35                  40                  45
Ser Leu Gly Pro Val Cys Pro Phe Arg Cys Gln Cys His Leu Arg Val
    50                  55                  60
Val Gln Cys Ser Asp Leu Gly Leu Asp Lys Val Pro Lys Asp Leu Pro
65                  70                  75                  80
Pro Asp Thr Thr Leu Leu Asp Leu Gln Asn Asn Lys Ile Thr Glu Ile
                85                  90                  95
Lys Asp Gly Asp Phe Lys Asn Leu Lys Asn Leu His Ala Leu Ile Leu
            100                 105                 110
Val Asn Asn Lys Ile Ser Lys Val Ser Pro Gly Ala Phe Thr Pro Leu
        115                 120                 125
Val Lys Leu Glu Arg Leu Tyr Leu Ser Lys Asn Gln Leu Lys Glu Leu
    130                 135                 140
Pro Glu Lys Met Pro Lys Thr Leu Gln Glu Leu Arg Ala His Glu Asn
145                 150                 155                 160
Glu Ile Thr Lys Val Arg Lys Val Thr Phe Asn Gly Leu Asn Gln Met
                165                 170                 175
Ile Val Ile Glu Leu Gly Thr Asn Pro Leu Lys Ser Ser Gly Ile Glu
            180                 185                 190
Asn Gly Ala Phe Gln Gly Met Lys Lys Leu Ser Tyr Ile Arg Ile Ala
        195                 200                 205
Asp Thr Asn Ile Thr Ser Ile Pro Gln Gly Leu Pro Pro Ser Leu Thr
    210                 215                 220
Glu Leu His Leu Asp Gly Asn Lys Ile Ser Arg Val Asp Ala Ala Ser
225                 230                 235                 240
Leu Lys Gly Leu Asn Asn Leu Ala Lys Leu Gly Leu Ser Phe Asn Ser
                245                 250                 255
Ile Ser Ala Val Asp Asn Gly Ser Leu Ala Asn Thr Pro His Leu Arg
            260                 265                 270
Glu Leu His Leu Asp Asn Asn Lys Leu Thr Arg Val Pro Gly Gly Leu
        275                 280                 285
Ala Glu His Lys Tyr Ile Gln Val Val Tyr Leu His Asn Asn Asn Ile
    290                 295                 300
Ser Val Val Gly Ser Ser Asp Phe Cys Pro Pro Gly His Asn Thr Lys
305                 310                 315                 320
Lys Ala Ser Tyr Ser Gly Val Ser Leu Phe Ser Asn Pro Val Gln Tyr
                325                 330                 335
Trp Glu Ile Gln Pro Ser Thr Phe Arg Cys Val Tyr Val Arg Ser Ala
            340                 345                 350
Ile Gln Leu Gly Asn Tyr Lys
        355
```

<210> SEQ ID NO 19
<211> LENGTH: 464

```
<212> TYPE: PRT
<213> ORGANISM: Homo sapiens
<220> FEATURE:
<221> NAME/KEY: misc_feature
<223> OTHER INFORMATION: Human Antithrombin
<300> PUBLICATION INFORMATION:
<308> DATABASE ACCESSION NUMBER: genbank Accession No. 113936
<309> DATABASE ENTRY DATE: 1986-07-21
<313> RELEVANT RESIDUES: (1)..(464)

<400> SEQUENCE: 19

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
```

-continued

```
                355                 360                 365
Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
                420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 20
<211> LENGTH: 393
<212> TYPE: PRT
<213> ORGANISM: Homo sapiens
<220> FEATURE:
<221> NAME/KEY: misc_feature
<223> OTHER INFORMATION: Human Antithrombin Fragment
<300> PUBLICATION INFORMATION:
<308> DATABASE ACCESSION NUMBER: Genbank Accession No. 113936
<309> DATABASE ENTRY DATE: 1986-07-21
<313> RELEVANT RESIDUES: (1)..(393)

<400> SEQUENCE: 20

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
        50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240
```

```
Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp
385                 390

<210> SEQ ID NO 21
<211> LENGTH: 104
<212> TYPE: PRT
<213> ORGANISM: Homo sapiens
<220> FEATURE:
<221> NAME/KEY: misc_feature
<223> OTHER INFORMATION: Human Platelet Factor
<300> PUBLICATION INFORMATION:
<308> DATABASE ACCESSION NUMBER: Protein Sequence Record Genbank
      Accession No. NP_002611
<309> DATABASE ENTRY DATE: 1995-01-07
<313> RELEVANT RESIDUES: (1)..(104)

<400> SEQUENCE: 21

Met Ser Ser Ala Ala Arg Ser Arg Leu Thr Arg Ala Thr Arg Gln Glu
1               5                   10                  15

Met Leu Phe Leu Ala Leu Leu Leu Pro Val Val Ala Phe Ala
            20                  25                  30

Arg Ala Glu Ala Glu Glu Asp Gly Asp Leu Gln Cys Leu Cys Val Lys
        35                  40                  45

Thr Thr Ser Gln Val Arg Pro Arg His Ile Thr Ser Leu Glu Val Ile
    50                  55                  60

Lys Ala Gly Pro His Cys Pro Thr Ala Gln Leu Ile Ala Thr Leu Lys
65                  70                  75                  80

Asn Gly Arg Lys Ile Cys Leu Asp Leu Gln Ala Leu Leu Tyr Lys Lys
                85                  90                  95

Ile Ile Lys Glu His Leu Glu Ser
            100

<210> SEQ ID NO 22
<211> LENGTH: 227
<212> TYPE: PRT
<213> ORGANISM: Homo sapiens
<220> FEATURE:
<221> NAME/KEY: misc_feature
<223> OTHER INFORMATION: Human Prolactin
<300> PUBLICATION INFORMATION:
<308> DATABASE ACCESSION NUMBER: Protein Sequence Record Genbank
      Accession No. NP_000939
```

```
<309> DATABASE ENTRY DATE: 2001-10-15
<313> RELEVANT RESIDUES: (1)..(227)

<400> SEQUENCE: 22

Met Asn Ile Lys Gly Ser Pro Trp Lys Gly Ser Leu Leu Leu Leu Leu
1               5                   10                  15

Val Ser Asn Leu Leu Cys Gln Ser Val Ala Pro Leu Pro Ile Cys
            20                  25                  30

Pro Gly Gly Ala Ala Arg Cys Gln Val Thr Leu Arg Asp Leu Phe Asp
        35                  40                  45

Arg Ala Val Val Leu Ser His Tyr Ile His Asn Leu Ser Ser Glu Met
    50                  55                  60

Phe Ser Glu Phe Asp Lys Arg Tyr Thr His Gly Arg Gly Phe Ile Thr
65                  70                  75                  80

Lys Ala Ile Asn Ser Cys His Thr Ser Ser Leu Ala Thr Pro Glu Asp
                85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
        115                 120                 125

Glu Val Arg Gly Met Gln Glu Ala Pro Glu Ala Ile Leu Ser Lys Ala
130                 135                 140

Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
                165                 170                 175

Val Trp Ser Gly Leu Pro Ser Leu Gln Met Ala Asp Glu Glu Ser Arg
            180                 185                 190

Leu Ser Ala Tyr Tyr Asn Leu Leu His Cys Leu Arg Arg Asp Ser His
        195                 200                 205

Lys Ile Asp Asn Tyr Leu Lys Leu Leu Lys Cys Arg Ile Ile His Asn
    210                 215                 220

Asn Asn Cys
225

<210> SEQ ID NO 23
<211> LENGTH: 93
<212> TYPE: PRT
<213> ORGANISM: Homo sapiens
<220> FEATURE:
<221> NAME/KEY: misc_feature
<223> OTHER INFORMATION: Human Calcitonin
<300> PUBLICATION INFORMATION:
<308> DATABASE ACCESSION NUMBER: Genbank/EMBL DDBJ Accession No.
      CAA26189
<309> DATABASE ENTRY DATE: 1989-03-15
<313> RELEVANT RESIDUES: (1)..(93)

<400> SEQUENCE: 23

Val Leu Leu Ala Ala Leu Val Gln Asp Tyr Val Gln Met Lys Ala Ser
1               5                   10                  15

Glu Leu Glu Gln Glu Gln Glu Arg Glu Gly Ser Ser Leu Asp Ser Pro
            20                  25                  30

Arg Ser Lys Arg Cys Gly Asn Leu Ser Thr Cys Met Leu Gly Thr Tyr
        35                  40                  45

Thr Gln Asp Phe Asn Lys Phe His Thr Phe Pro Gln Thr Ala Ile Gly
    50                  55                  60

Val Gly Ala Pro Gly Lys Lys Arg Asp Met Ser Ser Asp Leu Glu Arg
```

```
                65                  70                  75                  80
Asp His Arg Pro His Val Ser Met Pro Gln Asn Ala Asn
                        85                  90

<210> SEQ ID NO 24
<211> LENGTH: 236
<212> TYPE: PRT
<213> ORGANISM: Homo sapiens
<300> PUBLICATION INFORMATION:
<308> DATABASE ACCESSION NUMBER: Genbank/EMBL DDBJ Accession No.
      AAE57231
<309> DATABASE ENTRY DATE: 2001-05-16
<313> RELEVANT RESIDUES: (1)..(236)

<400> SEQUENCE: 24

Met Thr Gly Tyr Glu Ala Arg Leu Ile Thr Phe Gly Thr Trp Met Tyr
1               5                   10                  15

Ser Val Asn Lys Glu Gln Leu Ala Arg Ala Gly Phe Tyr Ala Ile Gly
                20                  25                  30

Gln Glu Asp Lys Val Gln Cys Phe His Cys Gly Gly Gly Leu Ala Asn
            35                  40                  45

Trp Lys Pro Lys Glu Asp Pro Trp Glu Gln His Ala Lys Trp Tyr Pro
    50                  55                  60

Gly Cys Lys Tyr Leu Leu Glu Glu Lys Gly His Glu Tyr Ile Asn Asn
65                  70                  75                  80

Ile His Leu Thr Arg Ser Leu Glu Gly Ala Leu Val Gln Thr Thr Lys
                85                  90                  95

Lys Thr Pro Ser Leu Thr Lys Arg Ile Ser Asp Thr Ile Phe Pro Asn
            100                 105                 110

Pro Met Leu Gln Glu Ala Ile Arg Met Gly Phe Asp Phe Lys Asp Val
        115                 120                 125

Lys Lys Ile Met Glu Glu Arg Ile Gln Thr Ser Gly Ser Asn Tyr Lys
    130                 135                 140

Thr Leu Glu Val Leu Val Ala Asp Leu Val Ser Ala Gln Lys Asp Thr
145                 150                 155                 160

Thr Glu Asn Glu Leu Asn Gln Thr Ser Leu Gln Arg Glu Ile Ser Pro
                165                 170                 175

Glu Glu Pro Leu Arg Arg Leu Gln Glu Glu Lys Leu Cys Lys Ile Cys
            180                 185                 190

Met Asp Arg Tyr Ile Ala Val Val Phe Ile Pro Cys Gly His Leu Val
        195                 200                 205

Thr Cys Lys Gln Cys Ala Glu Ala Val Asp Arg Cys Pro Met Cys Ser
    210                 215                 220

Ala Val Ile Asp Phe Lys Gln Arg Val Phe Met Ser
225                 230                 235

<210> SEQ ID NO 25
<211> LENGTH: 406
<212> TYPE: PRT
<213> ORGANISM: Homo sapiens
<220> FEATURE:
<221> NAME/KEY: misc_feature
<223> OTHER INFORMATION: Human Alpha-1-Antitrypsin
<300> PUBLICATION INFORMATION:
<308> DATABASE ACCESSION NUMBER: Genbank/EMBL DDBJ Accession No.
      AAH08915
<309> DATABASE ENTRY DATE: 2001-05-29
<313> RELEVANT RESIDUES: (1)..(406)

<400> SEQUENCE: 25
```

```
Met Gln Leu Phe Leu Leu Leu Cys Leu Val Leu Leu Ser Pro Gln Gly
1               5                   10                  15

Ala Ser Leu His Arg His His Pro Arg Glu Met Lys Lys Arg Val Glu
                20                  25                  30

Asp Leu His Val Gly Ala Thr Val Ala Pro Ser Ser Arg Arg Asp Phe
            35                  40                  45

Thr Phe Asp Leu Tyr Arg Ala Leu Ala Ser Ala Ala Pro Ser Gln Asn
        50                  55                  60

Ile Phe Phe Ser Pro Val Ser Ile Ser Met Ser Leu Ala Met Leu Ser
65                  70                  75                  80

Leu Gly Ala Gly Ser Ser Thr Lys Met Gln Ile Leu Glu Gly Leu Gly
                85                  90                  95

Leu Asn Leu Gln Lys Ser Ser Glu Lys Glu Leu His Arg Gly Phe Gln
                100                 105                 110

Gln Leu Leu Gln Glu Leu Asn Gln Pro Arg Asp Gly Phe Gln Leu Ser
        115                 120                 125

Leu Gly Asn Ala Leu Phe Thr Asp Leu Val Val Asp Leu Gln Asp Thr
        130                 135                 140

Phe Val Ser Ala Met Lys Thr Leu Tyr Leu Ala Asp Thr Phe Pro Thr
145                 150                 155                 160

Asn Phe Arg Asp Ser Ala Gly Ala Met Lys Gln Ile Asn Asp Tyr Val
                165                 170                 175

Ala Lys Gln Thr Lys Gly Lys Ile Val Asp Leu Leu Lys Asn Leu Asp
                180                 185                 190

Ser Asn Ala Val Val Ile Met Val Asn Tyr Ile Phe Phe Lys Ala Lys
                195                 200                 205

Trp Glu Thr Ser Phe Asn His Lys Gly Thr Gln Glu Gln Asp Phe Tyr
210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
                245                 250                 255

Val Pro Tyr Gln Gly Asn Ala Thr Ala Leu Phe Ile Leu Pro Ser Glu
                260                 265                 270

Gly Lys Met Gln Gln Val Glu Asn Gly Leu Ser Glu Lys Thr Leu Arg
                275                 280                 285

Lys Trp Leu Lys Met Phe Lys Lys Arg Gln Leu Glu Leu Tyr Leu Pro
        290                 295                 300

Lys Phe Ser Ile Glu Gly Ser Tyr Gln Leu Glu Lys Val Leu Pro Ser
305                 310                 315                 320

Leu Gly Ile Ser Asn Val Phe Thr Ser His Ala Asp Leu Ser Gly Ile
                325                 330                 335

Ser Asn His Ser Asn Ile Gln Val Ser Glu Met Val His Lys Ala Val
                340                 345                 350

Val Glu Val Asp Glu Ser Gly Thr Arg Ala Ala Ala Thr Gly Thr
                355                 360                 365

Ile Phe Thr Phe Arg Ser Ala Arg Leu Asn Ser Gln Arg Leu Val Phe
        370                 375                 380

Asn Arg Pro Phe Leu Met Phe Ile Val Asp Asn Asn Ile Leu Phe Leu
385                 390                 395                 400

Gly Lys Val Asn Arg Pro
            405
```

<210> SEQ ID NO 26
<211> LENGTH: 32
<212> TYPE: PRT
<213> ORGANISM: synthetic

<400> SEQUENCE: 26

Ala Leu Ala Gly Leu Ala Ser Pro Gly Leu Tyr Gly Leu Ala Arg Gly
1               5                   10                  15

Val Ala Leu Leu Glu Pro Arg Gly Leu Tyr Ser Glu Arg Gly Leu Tyr
                20                  25                  30

<210> SEQ ID NO 27
<211> LENGTH: 33
<212> TYPE: PRT
<213> ORGANISM: synthetic

<400> SEQUENCE: 27

Ala Leu Ala Pro Arg Gly Leu Leu Tyr Ser Gly Leu Tyr Leu Tyr Ser
1               5                   10                  15

Ala Ser Asn Thr His Arg Leu Glu Gly Leu Tyr Ser Glu Arg Gly Leu
                20                  25                  30

Tyr

<210> SEQ ID NO 28
<211> LENGTH: 35
<212> TYPE: PRT
<213> ORGANISM: synthetic

<400> SEQUENCE: 28

Ala Leu Ala Pro Arg Ser Glu Arg Ser Glu Arg Leu Tyr Ser Ser Glu
1               5                   10                  15

Arg Thr His Arg Ser Glu Arg Gly Leu Tyr Gly Leu Tyr Ser Glu Arg
                20                  25                  30

Gly Leu Tyr
        35

<210> SEQ ID NO 29
<211> LENGTH: 34
<212> TYPE: PRT
<213> ORGANISM: synthetic

<400> SEQUENCE: 29

Ala Leu Ala Leu Tyr Ser Pro Arg Gly Leu Tyr Leu Glu Val Ala Leu
1               5                   10                  15

Ala Ser Pro Ala Ser Asn Gly Leu Asn Gly Leu Tyr Ser Glu Arg Gly
                20                  25                  30

Leu Tyr

<210> SEQ ID NO 30
<211> LENGTH: 36
<212> TYPE: PRT
<213> ORGANISM: synthetic

<400> SEQUENCE: 30

Ala Leu Ala Pro His Glu Gly Leu Tyr Ala Ser Asn Ala Leu Ala Ala
1               5                   10                  15

Ser Asn Ser Glu Arg Ala Leu Ala Ala Arg Gly Leu Tyr Ser Glu
                20                  25                  30

Arg Gly Leu Tyr
        35

```
<210> SEQ ID NO 31
<211> LENGTH: 34
<212> TYPE: PRT
<213> ORGANISM: synthetic

<400> SEQUENCE: 31

Ala Leu Ala Pro Arg Ser Glu Arg Ala Ser Pro Leu Tyr Ser Gly Leu
1               5                   10                  15

Gly Leu Tyr Thr Tyr Arg Ser Glu Arg Gly Leu Tyr Ser Glu Arg Gly
            20                  25                  30

Leu Tyr

<210> SEQ ID NO 32
<211> LENGTH: 34
<212> TYPE: PRT
<213> ORGANISM: synthetic

<400> SEQUENCE: 32

Ala Leu Ala Leu Tyr Ser Pro Arg Ala Ser Asn Pro Arg Thr His Arg
1               5                   10                  15

Gly Leu Tyr Thr His Arg Val Ala Leu Gly Leu Tyr Ser Glu Arg Gly
            20                  25                  30

Leu Tyr

<210> SEQ ID NO 33
<211> LENGTH: 35
<212> TYPE: PRT
<213> ORGANISM: synthetic

<400> SEQUENCE: 33

Ala Leu Ala Ile Leu Glu His Ile Ser Gly Leu Thr Tyr Arg Pro His
1               5                   10                  15

Glu Ala Arg Gly Gly Leu Tyr Gly Leu Tyr Gly Leu Tyr Ser Glu Arg
            20                  25                  30

Gly Leu Tyr
        35

<210> SEQ ID NO 34
<211> LENGTH: 34
<212> TYPE: PRT
<213> ORGANISM: synthetic

<400> SEQUENCE: 34

Ala Leu Ala Leu Glu His Ile Ser Gly Leu Tyr Ala Arg Gly Gly Leu
1               5                   10                  15

Tyr Gly Leu Tyr Gly Leu Ala Ser Pro Gly Leu Tyr Ser Glu Arg Gly
            20                  25                  30

Leu Tyr

<210> SEQ ID NO 35
<211> LENGTH: 35
<212> TYPE: PRT
<213> ORGANISM: synthetic

<400> SEQUENCE: 35

Ala Leu Ala Ser Glu Arg Ser Glu Arg Pro Arg Ala Ser Pro Val Ala
1               5                   10                  15

Leu Ala Leu Ala Leu Tyr Ser Gly Leu Tyr Gly Leu Tyr Ser Glu Arg
            20                  25                  30
```

```
Gly Leu Tyr
        35
```